(12) United States Patent
Tanaka

(10) Patent No.: US 11,103,217 B2
(45) Date of Patent: Aug. 31, 2021

(54) ULTRASOUND SIGNAL PROCESSING METHOD AND ULTRASOUND SIGNAL PROCESSING DEVICE

(71) Applicant: Konica Minolta, Inc., Tokyo (JP)

(72) Inventor: Ryuichiro Tanaka, Kyoto-fu (JP)

(73) Assignee: KONICA MINOLTA, INC., Tokyo (JP)

( * ) Notice: Subject to any disclaimer, the term of this patent is extended or adjusted under 35 U.S.C. 154(b) by 540 days.

(21) Appl. No.: 16/133,092

(22) Filed: Sep. 17, 2018

(65) Prior Publication Data

US 2019/0090854 A1    Mar. 28, 2019

(30) Foreign Application Priority Data

Sep. 28, 2017   (JP) .............................. JP2017-188491

(51) Int. Cl.
| | | |
|---|---|---|
| *G10K 11/34* | (2006.01) | |
| *A61B 8/08* | (2006.01) | |
| *A61B 8/00* | (2006.01) | |
| *G06T 7/00* | (2017.01) | |
| *G01S 7/52* | (2006.01) | |
| *G01S 15/89* | (2006.01) | |

(52) U.S. Cl.
CPC .......... *A61B 8/5207* (2013.01); *A61B 8/4461* (2013.01); *A61B 8/5223* (2013.01); *G01S 7/52047* (2013.01); *G01S 7/52085* (2013.01); *G01S 15/8915* (2013.01); *G01S 15/8927* (2013.01); *G01S 15/8997* (2013.01); *G06T 7/0014* (2013.01); *G10K 11/346* (2013.01); *G06T 2207/10132* (2013.01); *G06T 2207/30004* (2013.01)

(58) Field of Classification Search
None
See application file for complete search history.

(56) References Cited

U.S. PATENT DOCUMENTS

2004/0210137 A1    10/2004   Baba et al.

FOREIGN PATENT DOCUMENTS

| JP | 63-27783 A | 2/1988 |
|---|---|---|
| JP | 2003070786 A | 3/2003 |
| WO | 03/022153 A1 | 3/2003 |

OTHER PUBLICATIONS

M. Itou, et al; Ultrasound Diagnostic Equipment; Corona Publishing Co., Ltd, Aug. 26, 2002, pp. 42-45.

S.I. Nikolov, et al; Virtual ultrasound sources in high resolution ultrasound imaging; Proc, SPIE—Progress in biomedical optics and imaging, vol. 3, 2002, pp. 395-405.

*Primary Examiner* — Jason M Ip
(74) *Attorney, Agent, or Firm* — Lucas & Mercanti, LLP

(57) ABSTRACT

A reception beamformer 140 makes use of an ultrasound probe that includes N transducers in an azimuth direction, and includes: a partial frame memory 1432 partitioned into M0 azimuth direction×D depth direction addresses, where M0≤N; and a synthesizer 143 that makes a correlation between acoustic line signal line data corresponding to transmission events and addresses of the partial frame memory 1432, synthesizes acoustic line signal line data obtained from transmission events by summing acoustic line signals with data stored at correlation addresses S which have been correlated with the acoustic line signals, and generates acoustic line signal frame data having N lines in the azimuth direction.

14 Claims, 27 Drawing Sheets

Output synthesized acoustic line signal line data for which synthesis is complete

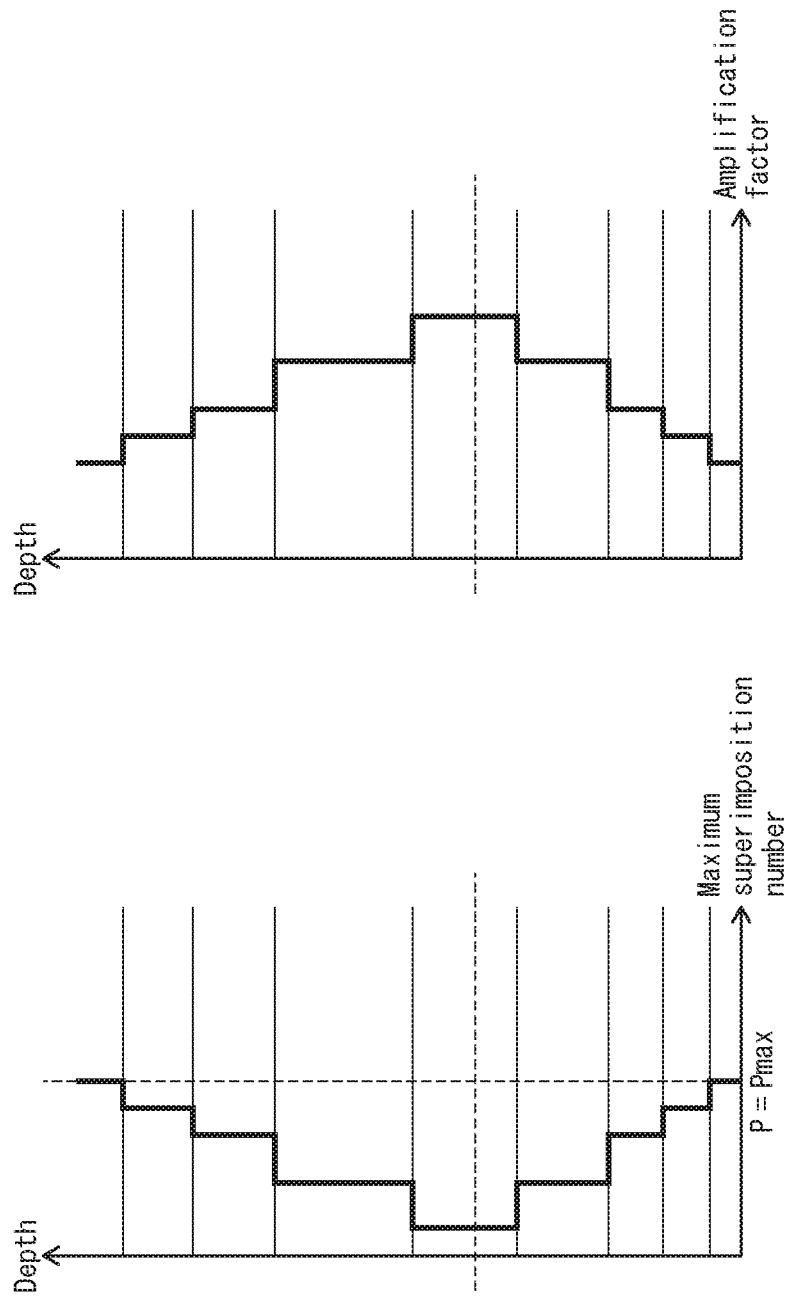

FIG. 12A1
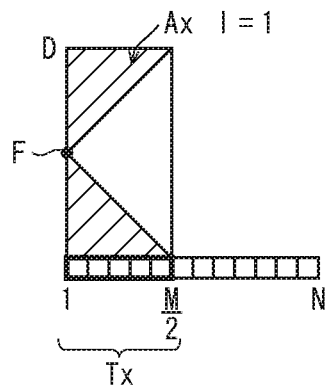
FIG. 12A2
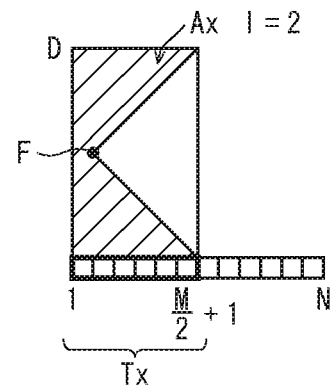
FIG. 12B1
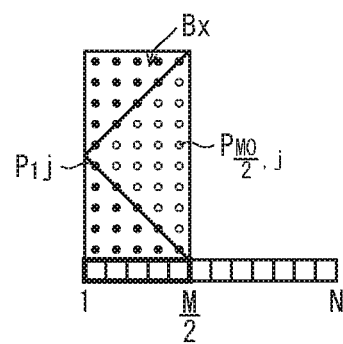
FIG. 12B2
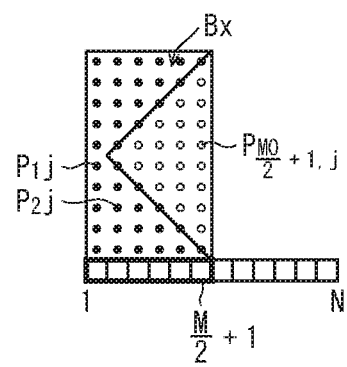
FIG. 12C1
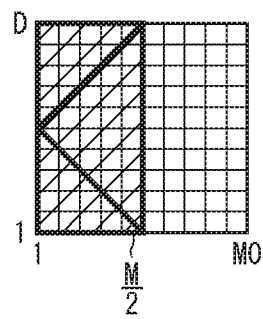
FIG. 12C2
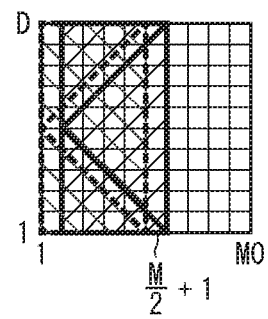

FIG. 13A1 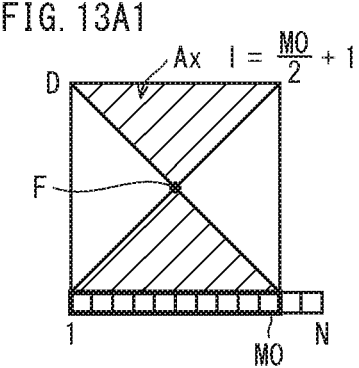
FIG. 13A2 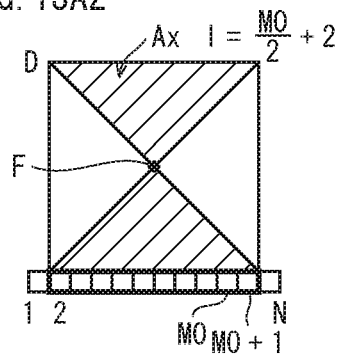
FIG. 13B1 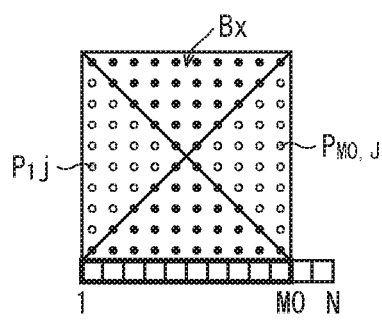
FIG. 13B2 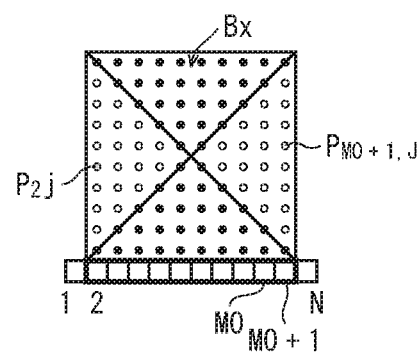
FIG. 13C1 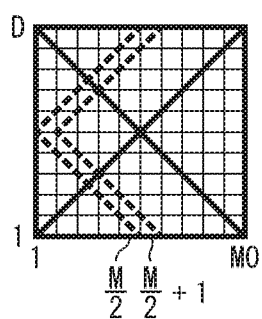
FIG. 13C2 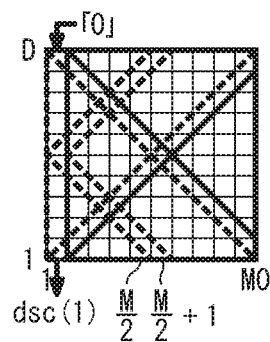
FIG. 13C3 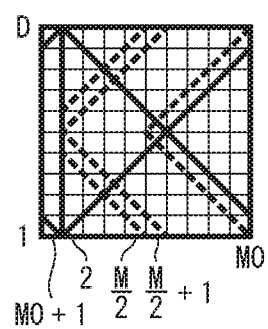

FIG. 14A1
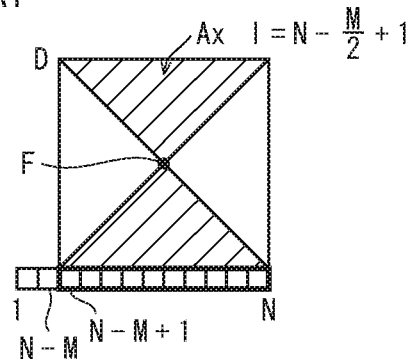
FIG. 14B1
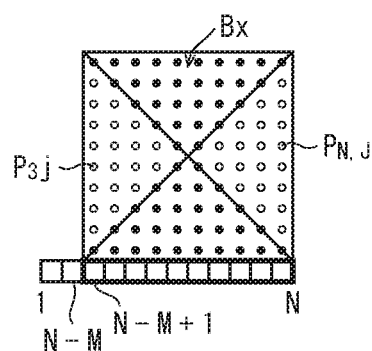
FIG. 14C1
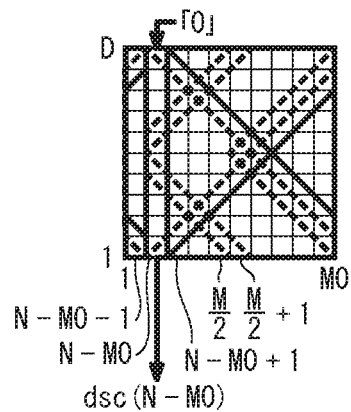
FIG. 14C2
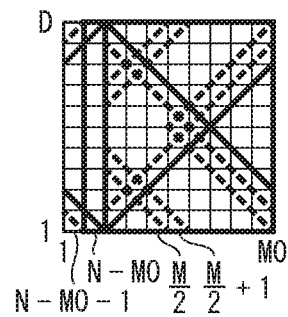

FIG. 18A1
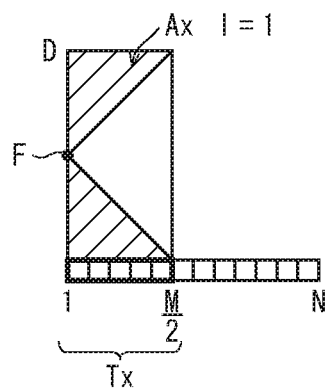
FIG. 18A2
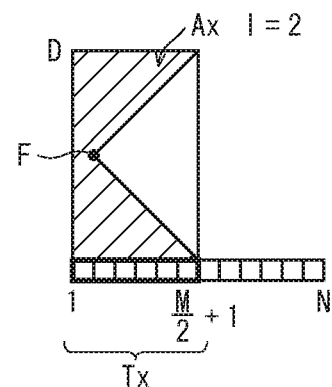
FIG. 18B1
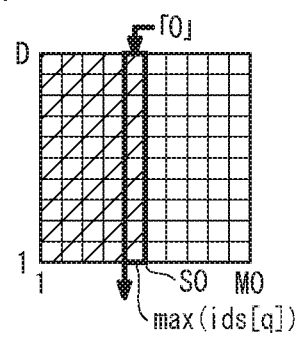
FIG. 18B2
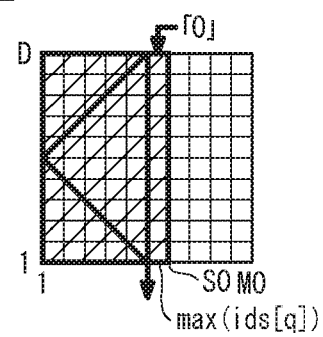
FIG. 18C1
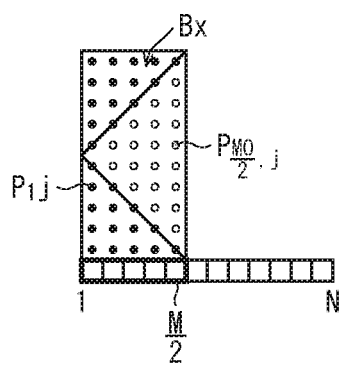
FIG. 18C2
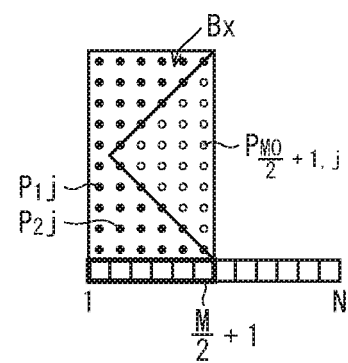
FIG. 18D1
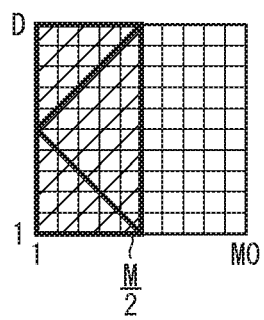
FIG. 18D2
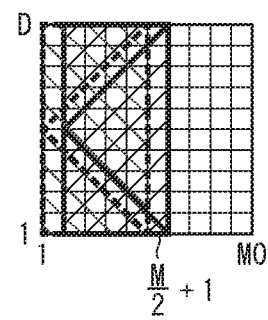

FIG. 19A1
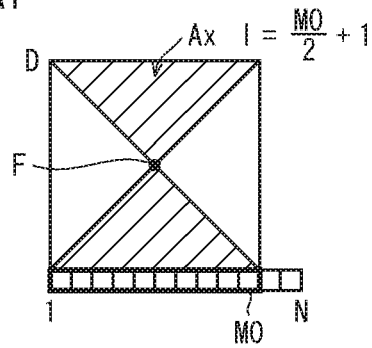
FIG. 19A2
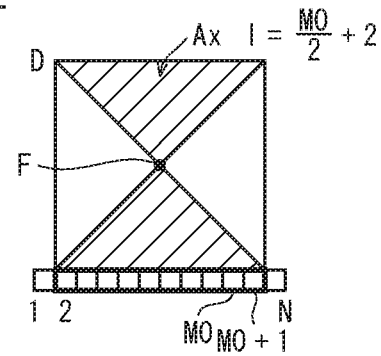
FIG. 19B1
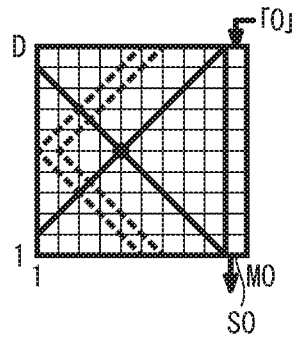
FIG. 19B2
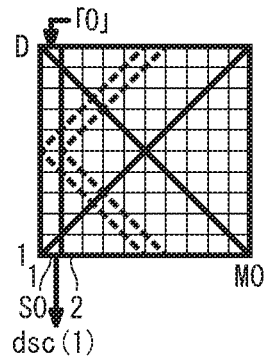
FIG. 19C1
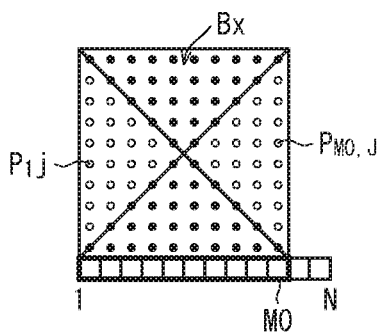
FIG. 19C2
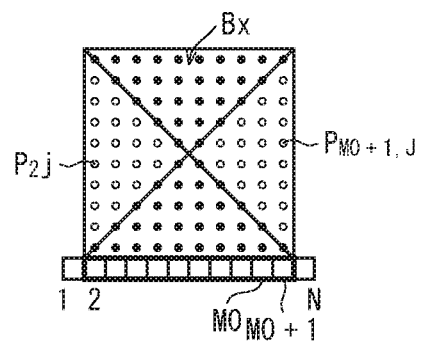
FIG. 19D1
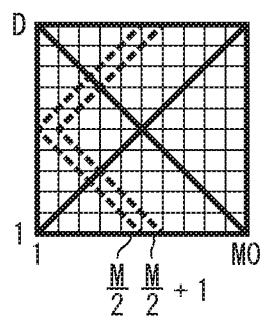
FIG. 19D2
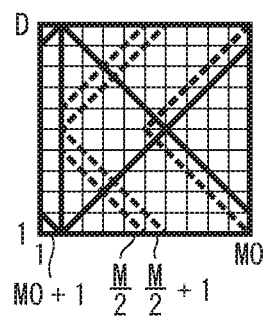

FIG. 24
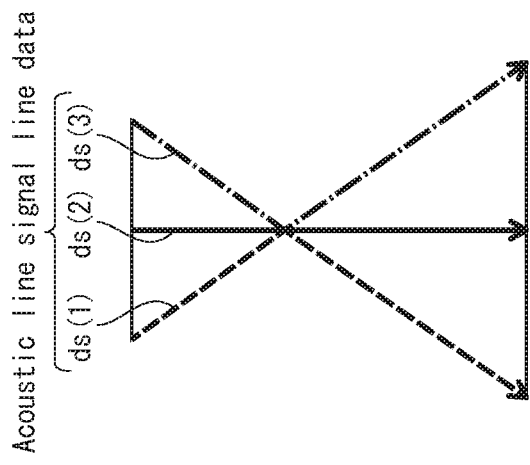
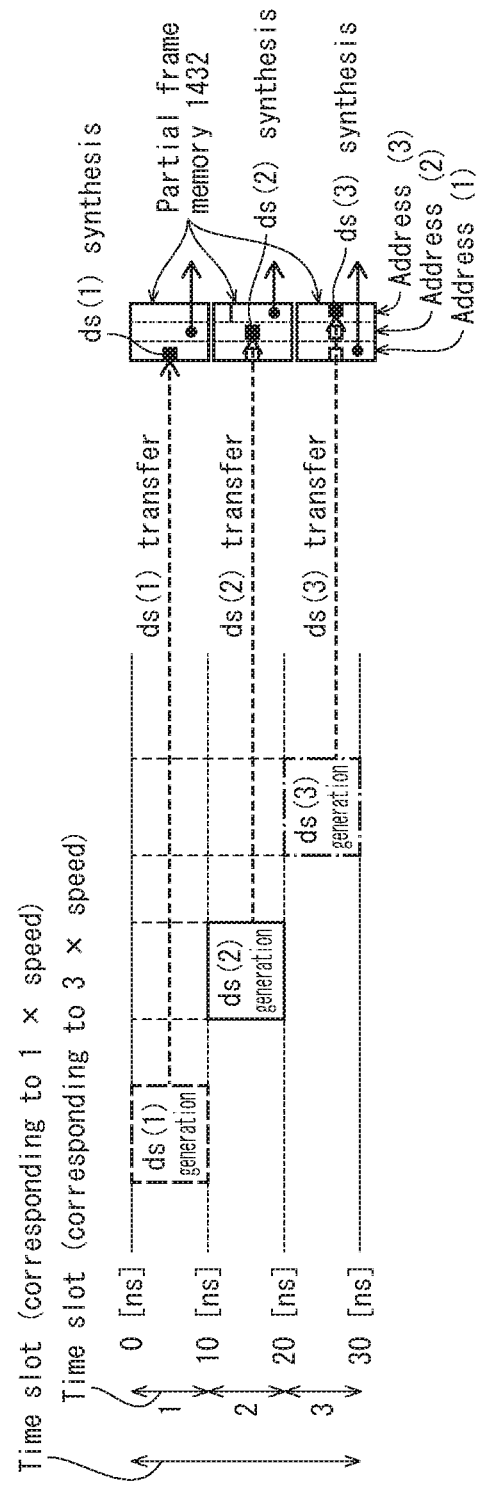

ULTRASOUND SIGNAL PROCESSING METHOD AND ULTRASOUND SIGNAL PROCESSING DEVICE

This application claims priority to Japanese Patent Application No. 2017-188491, filed Sep. 28, 2017, the contents of which are hereby incorporated by reference in their entirety.

BACKGROUND

Technical Field

The present disclosure relates to ultrasound signal processing methods and ultrasound diagnostic devices using ultrasound signal processing methods, and in particular to reception beamforming processing in ultrasound signal processing methods.

Description of the Related Art

An ultrasound diagnostic device transmits ultrasound to the inside of a subject from a ultrasound probe, receives reflected waves of ultrasound generated from differences in acoustic impedance of tissue in the subject, and generates and displays an ultrasound tomographic image indicating shapes of the tissue in the subject, based on obtained electric signals.

In conventional ultrasound diagnostic devices, delay-and-sum methods are used as reception beamforming methods based on received reflected waves (for example, see "Ultrasound Diagnostic Equipment", T. Ito and M. Tsuyoshi, Corona Publishing Co. Ltd, Aug. 26, 2002, pp 42-45). According to this method, an ultrasound beam is transmitted from a plurality of transducers to focus at a certain depth in a subject and generate an acoustic line signal on a central axis of the ultrasound beam.

Further, as a method for obtaining a high spatial resolution, high-quality image in a region other than in close vicinity to a transmission focus point, a reception beamforming method using a synthetic aperture method has been proposed (for example, see "Virtual Ultrasound Sources in High Resolution Ultrasound Imaging", S. I. Nikolov and J. A. Jensen, SPIE—Progress in Biomedical Optics and Imaging, vol. 3, 2002, P. 395-405). According to the synthetic aperture method it is possible to generate acoustic line signals for an entirety of an ultrasound primary irradiation region that includes the close vicinity of a transmission focus point for one ultrasound transmission, by performing a delay control that takes into account both ultrasound transmission propagation paths and arrival times of reflected waves to transducers via the propagation paths. Further, according to the synthetic aperture method, spatial resolution and signal-to-noise ratio can be improved by superimposing a plurality of acoustic line signals for the same observation point obtained from a plurality of ultrasound transmissions.

SUMMARY

However, according to the synthetic aperture method, a synthesizing process is performed to superimpose a plurality of acoustic line signals for the same observation point obtained from a plurality of times of ultrasound transmission and reception. As resolution increases, the number of observation points in a target region for which acoustic line signals are generated by one ultrasound transmission increases, and therefore, for the synthesizing process, frame memory capacity required to store acoustic line signal data after delay-and-sum increases, and data transmission capability required for transferring acoustic line signal data after delay-and-sum increases. Thus, expanding memory capacity for storing acoustic line signals and expanding data transmission capability results in an increase in costs for ultrasound diagnostic devices.

The present disclosure is made in view of the problems described above, and it is an object of the present disclosure to provide an ultrasound signal processing method and an ultrasound signal processing device that can reduce a memory capacity required for acoustic line signal synthesis processing in a reception beamformer used in a synthetic aperture method, while also suppressing a reduction in spatial resolution and signal-to-noise ratio.

An ultrasound signal processing device pertaining to one aspect of the present disclosure is an ultrasound signal processing device that transmits an ultrasound beam from an ultrasound probe provided with N transducers in an azimuth direction, where N is a natural number greater than 1, and generates N azimuth direction×Z depth direction acoustic line signal frame data from acoustic line signals based on reflected ultrasound, where Z is a natural number, the ultrasound signal processing device including ultrasound signal processing circuitry, the ultrasound signal processing circuitry including: a transmitter that repeats transmission events, in which an ultrasound beam is transmitted from an array of transmission transducers selected from the N transducers, the array of transmission transducers being shifted by Mp transducers in the azimuth direction per transmission event, where Mp is a natural number; a delay-and-sum unit that generates a radio frequency (RF) signal sequence based on reflected ultrasound received by all or a plurality of the N transducers corresponding to a transmission event, performs delay-and-sum processing on the RF signal sequences for each observation point corresponding to positions in an ultrasound beam irradiation region, and generates ML lines of acoustic line signal line data, where ML is a natural number less than N; a partial frame memory partitioned into M0 azimuth direction×D depth direction addresses, where M0 is a natural number such that ML≤M0≤N and D is a natural number; a synthesizer that makes a correlation between acoustic line signal line data corresponding to transmission events and addresses of the partial frame memory, using positions of observation points from which acoustic line signals are obtained as a reference, synthesizes acoustic line signal line data obtained from transmission events by summing acoustic line signals with data stored at corresponding addresses which have been correlated with the acoustic line signals, and generates the N azimuth direction×D depth direction acoustic line signal frame data; and an ultrasound image generator that generates an ultrasound image based on the acoustic line signal frame data, wherein the synthesizer makes the correlation between the acoustic line signal line data corresponding to transmission events and the addresses of the partial frame memory in an order along the azimuth direction, when acoustic line signal line data is correlated with an (M0)th address in the azimuth direction of the partial frame memory, remaining acoustic line signal line data in the azimuth direction is then correlated in the order along the azimuth direction to addresses starting from a first address in the azimuth direction of the partial frame memory, and an address in the azimuth direction of the partial frame memory to which acoustic line signal line data is correlated, counting back Mp lines in the azimuth direction starting at a latest acoustic line signal line data corresponding to the transmission event, is specified as an addition correlation address, values of acoustic line signals correlated with addresses from the first address to an address one before the addition correlation address in the azimuth direction of the partial frame memory are summed with data stored at the addresses, and results of summing are written to the addresses, and with respect to Mp addresses starting at and including the addition correlation address in the order along the azimuth direction of the partial frame memory, after outputting to the ultrasound image generator data stored at the Mp addresses, values of corresponding acoustic line signals are written to the Mp addresses.

BRIEF DESCRIPTION OF DRAWINGS

These and other objects, advantages, and features of the technology pertaining to the present disclosure will become apparent from the following description thereof taken in conjunction with the accompanying drawings, which illustrate at least one embodiment of the technology pertaining to the present disclosure.

FIG. 11A is a schematic diagram illustrating maximum number of superimpositions in synthesized acoustic line signals, and FIG. 11B is a schematic diagram illustrating amplification processing in an amplification processor 1435.

FIGS. 12A1, 12B1, 12C1, 12A2, 12B2, 12C2 are schematic diagrams illustrating synthesis of synthesized acoustic line signals by the synthesizer 143 pertaining to Embodiment 1; FIGS. 12A1, 12B1, 12C1 illustrate a first transmission event and FIGS. 12A2, 12B2, 12C2 illustrate a second transmission event.

FIGS. 13A1, 13B1, 13C1, 13A2, 13B2, 13C2, 13C3 are schematic diagrams illustrating synthesis of synthesized acoustic line signals by the synthesizer 143 pertaining to Embodiment 1; FIGS. 13A1, 13B1, 13C1 illustrate an Mth transmission event and FIGS. 13A2, 13B2, 13C2, 13C3 illustrate an (M+1)th transmission event.

FIGS. 14A1, 14B1, 14C1, 14C2 are schematic diagrams illustrating synthesis of synthesized acoustic line signals by the synthesizer 143 pertaining to Embodiment 1 for an Nth transmission event.

FIGS. 18A1, 18B1, 18C1, 18D1, 18A2, 18B2, 18C2, 18D2 are schematic diagrams illustrating synthesis of synthesized acoustic line signals by the synthesizer 143 pertaining to Embodiment 2; FIGS. 18A1, 18B1, 18C1, 18D1 illustrate a first transmission event and FIGS. 18A2, 18B2, 18C2, 18D2 illustrate a second transmission event.

FIGS. 19A1, 19B1, 19C1, 19D1, 19A2, 19B2, 19C2, 19D2 are schematic diagrams illustrating synthesis of synthesized acoustic line signals by the synthesizer 143 pertaining to Embodiment 2; FIGS. 19A1, 19B1, 19C1, 19D1 illustrate an Mth transmission event and FIGS. 19A2, 19B2, 19C2, 19D2 illustrate an (M+1)th transmission event.

FIG. 24 is a schematic diagram illustrating synthesis of synthesized acoustic line signals by the synthesizer 143 pertaining to Modification 1.

DETAILED DESCRIPTION

<<Developments Leading to Embodiments>>

Figure 1:
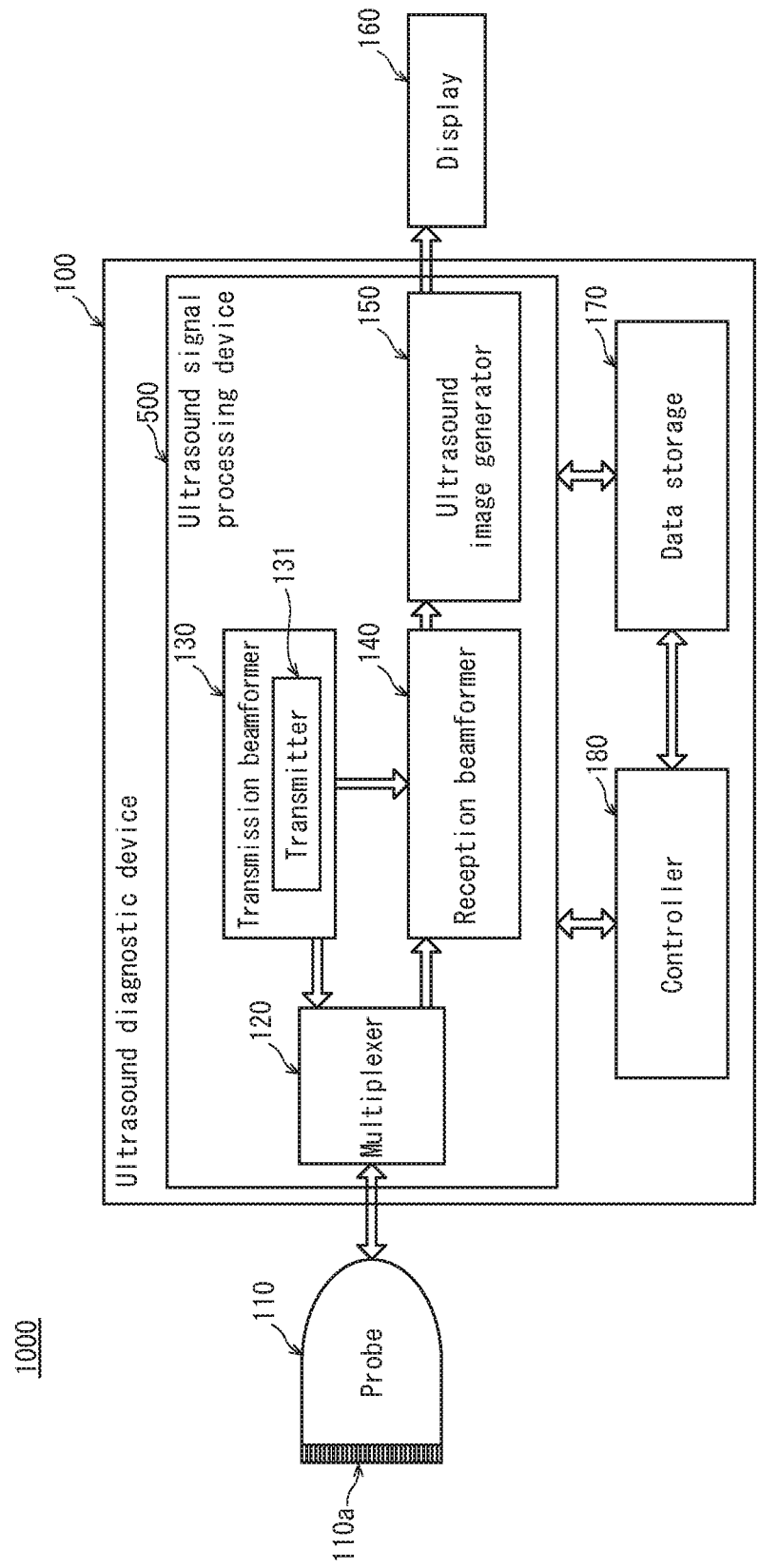
FIG. 1 is a function block diagram of an ultrasound diagnostic device 100 pertaining to Embodiment 1.

The inventors conducted various investigations in order to reduce memory capacity required in an ultrasound signal processing device that uses a synthetic aperture method while suppressing a decrease in acoustic line signal spatial resolution and signal-to-noise ratio.

Typically, in convergent transmission beamforming, an ultrasound primary irradiation region converges at or near a focus point at a depth of the focus point, and at other depths the farther the distance to the focus depth the greater the width in a transducer array direction. Thus, the ultrasound primary irradiation region is an hourglass-shaped region bounded by a transmission transducer array and two straight lines starting at ends of the transmission transducer array and passing through a transmission focus point where ultrasound beams converge.

According to a synthetic aperture method, observation points can be set for an entirety of an ultrasound primary irradiation region of one transmission event, and therefore the entirety of the ultrasound primary irradiation region is preferably a target region.

Further, when a region corresponding to all transducers of a probe for which an ultrasound image is generated is set as one frame, in order to generate an ultrasound image for one frame, multiple ultrasound transmission and reception steps (transmission events) are performed for different target regions, and multiple acoustic line signal line data obtained corresponding to a transmission event are synthesized with reference to a position of an observation point, and synthesized as one acoustic line signal frame data.

However, the number of observation points included in a target region is proportional to resolution of an image to be obtained, and therefore in order to achieve higher definitions both frame memory capacity for storing post-delay-and-sum acoustic line signals for synthesis processing and data transfer capability for transferring acoustic line signals for synthesis processing are increased. In order to suppress degradation in temporal resolution and usability, a processor including high speed/high capacity frame memory and a memory controller having a high processing capability that can quickly transfer post-delay-and-sum data is required, such as a high-performance field-programmable gate array (FPGA) or application-specific integrated circuit (ASIC), and this leads to an increase in cost of an ultrasound signal processing device.

A reduction in hardware cost through distributed processing may be considered. In this case, processing is distributed across a plurality of calculators, necessitating a decrease in calculation load per calculator. For example, delay-and-sum processing from transmission and reception corresponding to a plurality of transducers, reception beamforming up until synthesis according to a synthetic aperture method, envelope detection with respect to acoustic line signals with obtained acoustic line signal frame data as input, conversion into luminance signals via logarithmic compression, and ultrasound image generation processing after generating coordinate-transformed B mode image frame data can each be implemented by hardware using a plurality of small-scale FPGA, which can significantly reduce costs of computing units in hardware. In other words, an increase in costs caused by large scale calculations when functions are implemented by a central processor by using one FPGA or the like can be avoided. Hardware such as FPGAs that can perform large scale calculations is very expensive, and costs can be reduced by distributing the calculation load across a plurality of integrated circuits.

Conventionally, when using small scale FPGAs with respect to a synthetic aperture method, a large capacity frame memory for synthesis processing is provided external to the FPGAs for a synthetic aperture method. For this reason, in addition to providing high speed, high capacity double data rate (DDR) memory, a memory controller having a high processing capability that can perform high speed data transfer between FPGA and DDR memory is provided in the FPGA, leading to increases in hardware costs for both FPGA and DDR memory. On the other hand, when FPGA internal memory is used as a frame memory for synthesis processing, data transfer between FPGA and DDR memory does not occur. However, a large-scale static random-access (SRAM) is provided inside the FPGA, which is a factor in high hardware costs.

If beamforming processing up until synthesis processing can be realized by using only internal memory of small-scale FPGAs, it becomes possible to greatly reduce hardware costs. In view of this, the inventors conducted intensive study on synthesis processing methods for reducing frame memory capacity required for synthesis processing in reception beamforming processing used in a synthetic aperture method, and arrived at the embodiments described below.

The following is a description of an ultrasound processing method and an ultrasound signal processing device using the ultrasound processing method pertaining to an embodiment, described with reference to the drawings.

Embodiment 1

<Overall Configuration>

The following is a description of an ultrasound diagnostic device 100 pertaining to Embodiment 1, described with reference to the drawings.

FIG. 1 is a function block diagram of an ultrasound diagnostic system 1000 pertaining to Embodiment 1. In FIG. 1, the ultrasound diagnostic system 1000 includes a probe 110 that has transducers 110a that transmit ultrasound towards a subject and receive reflected waves, the ultrasound diagnostic device 100 that causes the probe 110 to transmit and receive ultrasound and generates ultrasound images based on output signals from the probe 110, and a display 160 that displays an ultrasound image on a screen. The probe 110 and the display 160 are each connectable to the ultrasound diagnostic device 100.

<Configuration of Ultrasound Diagnostic Device 100>

The ultrasound diagnostic device 100 includes a multiplexer 120 for securing input and output for each transducer used in transmission and reception among the transducers 110a of the probe 110, a transmission beamformer 130 that controls timing of high voltage application to the transducers 110a of the probe 110 for performing ultrasound transmission, and a reception beamformer 140 that amplifies, A/D converts, and performs reception beamforming on electric signals obtained by the transducers 110a based on reflected ultrasound received by the probe 110, in order to generate acoustic line signals (delay-and-sum data (DAS data)). Further, the ultrasound diagnostic device 100 includes an ultrasound image generator 150 that generates ultrasound images (B mode images) based on output signals from the reception beamformer 140, a data storage 170 that stores ultrasound images output by the ultrasound image generator 150, and a controller 180 that controls each element.

Among these elements, the multiplexer 120, the transmission beamformer 130, the reception beamformer 140, and the ultrasound image generator 150 constitute an ultrasound signal processing device 500, which includes ultrasound signal processing circuitry.

Elements of the ultrasound diagnostic device 100, for example the multiplexer 120, the transmission beamformer 130, the reception beamformer 140, the ultrasound image generator 150, and the controller 180 are each implemented as a hardware circuit such as a field programmable gate array (FPGA), an application specific integrated circuit (ASIC), or the like. Alternatively, these elements may be implemented through software and a programmable device such as a processor. As a processor, a central processing unit (CPU) or a graphics processing unit (GPU) can be used, and in the case of a GPU may be referred to as general-purpose computing on a graphics processing unit (GPGPU). These elements can each be a single circuit component or an assembly of circuit components. Further, a plurality of elements can be combined into a single circuit component or can be an aggregate of a plurality of circuit components.

The data storage 170 is a computer-readable storage medium, and may be a flexible disk, a hard disk, magneto-optical (MO), a digital versatile disc (DVD), digital versatile disc random access memory (DVD-RAM), a Blu-ray Disc (BD), semiconductor memory, or the like. Further, the data storage 170 may be a storage device that is external and connectable to the ultrasound diagnostic device 100.

<Configuration of Elements of Ultrasound Diagnostic Device 100>

The ultrasound diagnostic device 100 pertaining to Embodiment 1 is characterized by the transmission beamformer 130 that causes ultrasound beam transmission from the transducers 110a of the probe 110 and the reception beamformer 140 that performs operations on electric signals obtained from ultrasound reflections received by the probe 110 in order to generate acoustic line signals for generating an ultrasound image. Thus, the present description primarily describes configuration and function of the transmission beamformer 130 and the reception beamformer 140. Note that configuration of the ultrasound diagnostic device 100 other than that of the transmission beamformer 130 and the reception beamformer 140 may be the same as that used in a known ultrasound diagnostic device, and a beamformer of a known ultrasound diagnostic device may be replaced by a beamformer pertaining to the present embodiment.

The following is a description of the transmission beamformer 130 and the reception beamformer 140.

1. Transmission Beamformer 130

The transmission beamformer 130 is connected to the probe 110 via the multiplexer 120 and controls timing of high voltage application to each of a plurality of transducers included in a transmission aperture Tx made up of all or some of the N (where N is a natural number and 2 or more) transducers 110a of the probe 110 in order to perform ultrasound transmission from the probe 110. The transmission beamformer 130 includes a transmitter 131.

Based on a transmission control signal from the controller 180, the transmitter 131 performs transmission processing supplying a pulsed transmit signal to each transducer included in the transmission aperture Tx among the transducers 110a of the probe 110, in order to cause transmission of an ultrasound beam. More specifically, the transmitter 131 includes, for example, a clock generator circuit, a pulse generator circuit, and a delay circuit. A clock generator circuit is a circuit that generates a clock signal for determining transmission timing of an ultrasound beam. A pulse generator circuit is a circuit for generating a pulse signal that drives a transducer. A delay circuit is a circuit for setting a delay time for each transducer for ultrasound beam transmission timing, delaying ultrasound beam transmission by the delay time in order to perform ultrasound beamforming.

The transmitter 131 repeatedly transmits ultrasound while shifting the transmission aperture Tx in the array direction by a movement pitch Mp (where Mp is a natural number) for each ultrasound transmission, performing ultrasound transmission from all the transducers 110a of the probe 110. According to the present embodiment, the movement pitch Mp is equivalent to one transducer, and therefore the transmission aperture Tx shifts by one transducer every ultrasound transmission. The movement pitch Mp is not limited to being equivalent to one transducer, and may be equivalent to two or more transducers. Information indicating positions of transducers included in the transmission aperture Tx is outputted from the data storage 170 via the controller 180. For example, if the number N of the transducers 110a of the probe 110 is 192, a number of transducers that constitute the transmission aperture Tx may be selected from 20 to 100, for example, and may be shifted by one transducer per ultrasound transmission, for example. Hereinafter, ultrasound transmission performed from a given transmission aperture Tx by the transmitter 131 may be referred to as a "transmission event".

Figure 2:
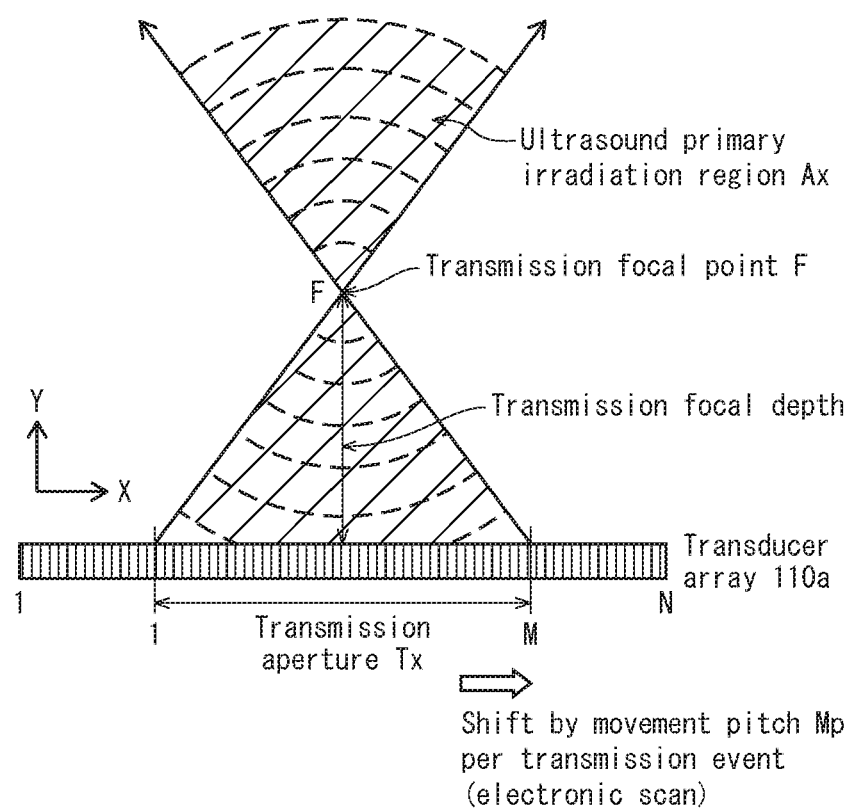
FIG. 2 is a diagram illustrating propagation paths of transmitted ultrasound beams according to a transmission beamformer 130 pertaining to Embodiment 1.

FIG. 2 is a schematic diagram illustrating propagation paths of ultrasound transmission according to the transmission beamformer 130. In a given transmission event, an array of M (where M is a natural number) transducers (transmission transducer array) included in the N transducers 110a arranged in an array contributing to ultrasound transmission is illustrated as the transmission aperture Tx. Further, array length of the transmission aperture Tx may be referred to as transmission aperture length. Further, the movement pitch Mp of the transmission transducer array each transmission event is less than the number M of the transducers included in the transmission transducer array.

In the transmission beamformer 130, transmission timing of each transducer is controlled so that the more central a transducer is in the transmission aperture Tx, the more transmission timing is delayed. As a result, a wavefront of an ultrasound transmission wave transmitted from the transducer array in the transmission aperture Tx is focused (converges) at a transmission focal point F at a focal depth in a subject. Focal depth of the transmission focus point F can be set arbitrarily. Here, the focal depth is the depth at which an ultrasound transmission wave reaches maximum convergence in an azimuth direction of the transducers (x direction in FIG. 2), that is, the depth at which the width of an ultrasound beam in the x direction is narrowest, and the transmission focal point F is a central position in the x direction of the ultrasound beam at the focal depth. However, the focal depth is constant during multiple transmission events pertaining to one frame. That is, a relationship between the transmission aperture Tx and the transmission focal point F relative to each other does not change in a plurality of transmission events pertaining to one frame. A wavefront converging at the transmission focal point F diffuses again and an ultrasound transmission wave propagates in an hourglass-shaped space bounded by two straight lines intersecting at the transmission focal point F with the transmission aperture Tx as a base. That is, an ultrasound wave radiated at the transmission aperture Tx propagates such that it gradually reduces in width in space (horizontal axis in the drawings) to a minimum width at the transmission focal point F, then as it progresses deeper (upwards in the drawings), it diffuses as the width increases. An area of this hourglass shape is an ultrasound primary irradiation region Ax.

2. Reception Beamformer 140 Configuration

Figure 3:
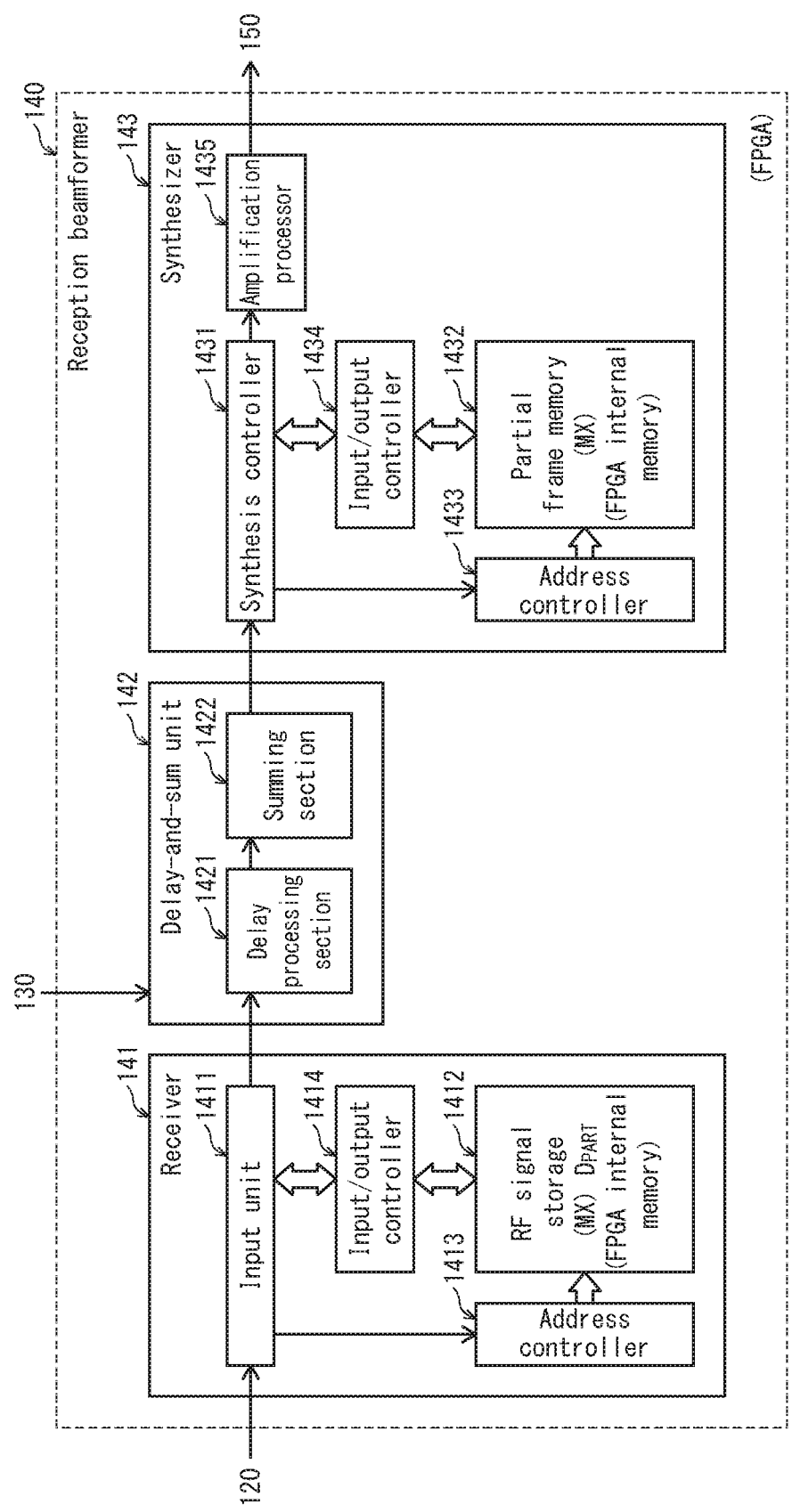
FIG. 3 is a function block diagram of a reception beamformer 140 pertaining to Embodiment 1.

The reception beamformer 140 generates acoustic line signals from electrical signals obtained by the transducers 110a, based on reflected ultrasound received by the probe 110. Here, "acoustic line signals" are signals after delay-and-sum processing with respect to a given observation point. Delay-and-sum processing is described in more detail later. FIG. 3 is a function block diagram illustrating configuration of the transmission beamformer 140. In FIG. 3, the transmission former 140 includes a receiver 141, a delay-and-sum unit 142, and a synthesizer 143.

The following describes configuration of elements of the reception beamformer 140.

(1) Receiver 141

The receiver 141 is connected to the probe 110 via the multiplexer 120, and is a circuit that generates radio frequency (RF) signals by amplifying and analogue-digital (AD) converting electrical signals obtained from reception of ultrasound by the probe 110 corresponding to a transmission event. The receiver 141 includes an input unit 1411, an RF signal storage 1412 that is a semiconductor memory, an address controller 1413, and an input/output controller 1414. The input unit 1411 generates RF signals in chronological order in an order of a transmission event and outputs the RF signals to the input/output controller 1414, and stores the RF signals at addresses of the RF signal storage 1412 specified by the address controller 1413.

Here, an RF signal is a digital signal obtained by AD conversion of an electrical signal converted from reflected ultrasound received by a transducer, and is composed of a series of signals that are continuous in a transmission direction (depth direction of subject) of ultrasound received by a transducer.

Figures 4A, 4B:
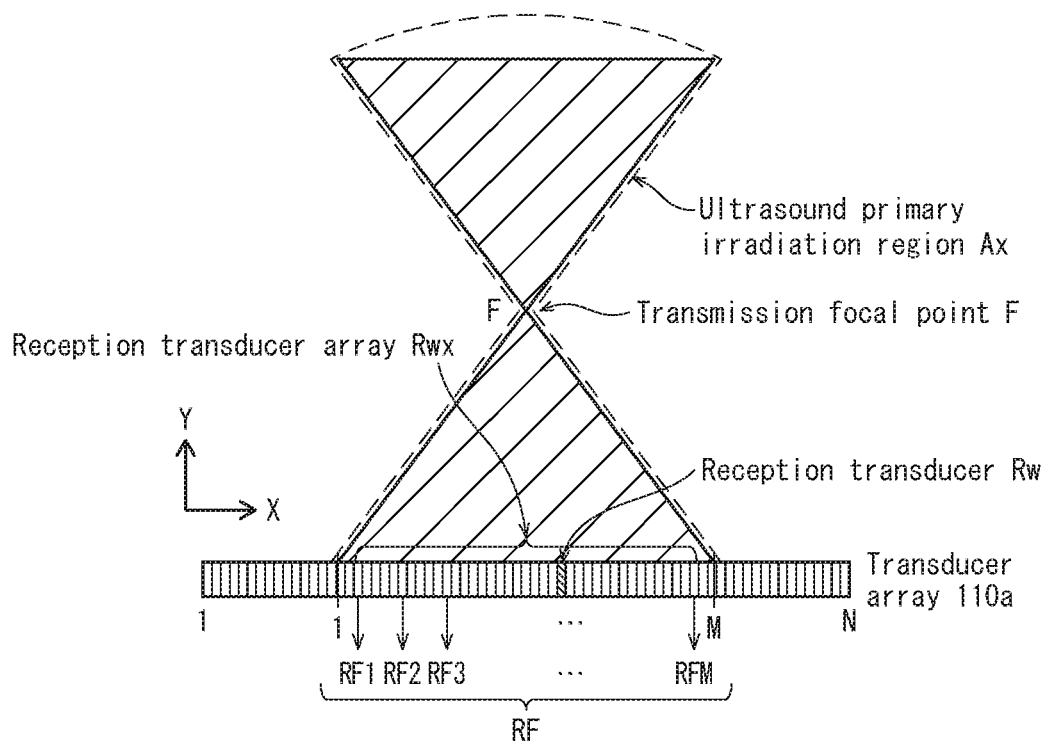
FIG. 4A is a schematic diagram illustrating generation of an RF signal sequence based on reflected ultrasound from an ultrasound primary irradiation region Ax.
FIG. 4B is a schematic diagram illustrating correspondence between RF signal sequences in a transmitter 141 and addresses of an RF signal storage 1412.

FIG. 4A is a schematic diagram illustrating RF signal sequence generation based on reflected ultrasound from the ultrasound primary irradiation region Ax. In a transmission event, as stated above, the transmitter 131 causes each transducer included in the transmission aperture Tx among the transducers 110a of the probe 110 to transmit an ultrasound beam. Further, the transmitter 131 repeatedly transmits ultrasound while shifting the transmission aperture Tx in the array direction by the movement pitch Mp, corresponding to transmission events, thereby performing ultrasound transmission from all the N transducers 110a of the probe 110.

The receiver 141, as illustrated in FIG. 4A, generates an RF signal sequence for each transducer, based on reflected ultrasound obtained from the ultrasound primary irradiation region Ax of the subject by each transducer corresponding to part or all of the transducers 110a of the probe 110, corresponding to a transmission event. A transducer receiving reflected ultrasound may be referred to as a reception transducer Rw, and an array of reception transducers Rw is a reception transducer array Rwx. A number of reception transducers in the reception transducer array Rwx is beneficially equal to or greater than a number of transducers included in the transmission aperture Tx. Further, the number of reception transducers may be a total number of the transducers 110a of the probe 110. According to the present embodiment, the number of the reception transducers Rw is M, and is equal to the number of transmission transducers.

The input unit 1411 generates a sequence of RF signals obtained by M reception transducers in each reception transducer array Rw, corresponding to transmission events, and stores generated RF signals for each transmission event in the RF signal storage 1412. According to the present embodiment, the RF signal storage 1412 is configured to use the internal semiconductor memory of the FPGA constituting the reception beamformer 140. However, the RF signal storage 1412 may be outside the FPGA. The input/output controller 1414 and the address controller 1413 control input and output of RF signal sequences to and from the RF signal storage 1412, based on instructions from the input unit 1411. FIG. 4B is a schematic diagram illustrating correspondence between RF signal sequences in the transmitter 141 and addresses of the RF signal storage 1412. The RF signal storage 1412 is a memory that holds a generated RF signal until delay-and-sum processing is performed in order to generate an acoustic line signal. As illustrated in FIG. 4B, the RF signal storage 1412 is partitioned into addresses composed of M, which is the same as a number reception transducers in the transducer array direction (azimuth direction) and Dpart (where Dpart is a natural number) in the subject depth direction. According to the present embodiment, when considering a maximum delay of a reflected wave in delay-and-sum processing, Dpart is set to 2,000 to 8,000 words, for example, and is smaller than a number of partitions for holding RF signals corresponding to a target region Bx (described later) in the subject depth direction (corresponding to about 16,000 to 20,000 words). Thus, the RF signal storage 1412 functions as a first in, first out (FIFO) memory, RF signals are generated on a time axis in an order reflected waves are obtained, and are held in the RF signal storage 1412 according to a first in, first out scheme starting from a shallow portion of the subject.

(2) Delay-and-Sum Unit 142

Figure 5:
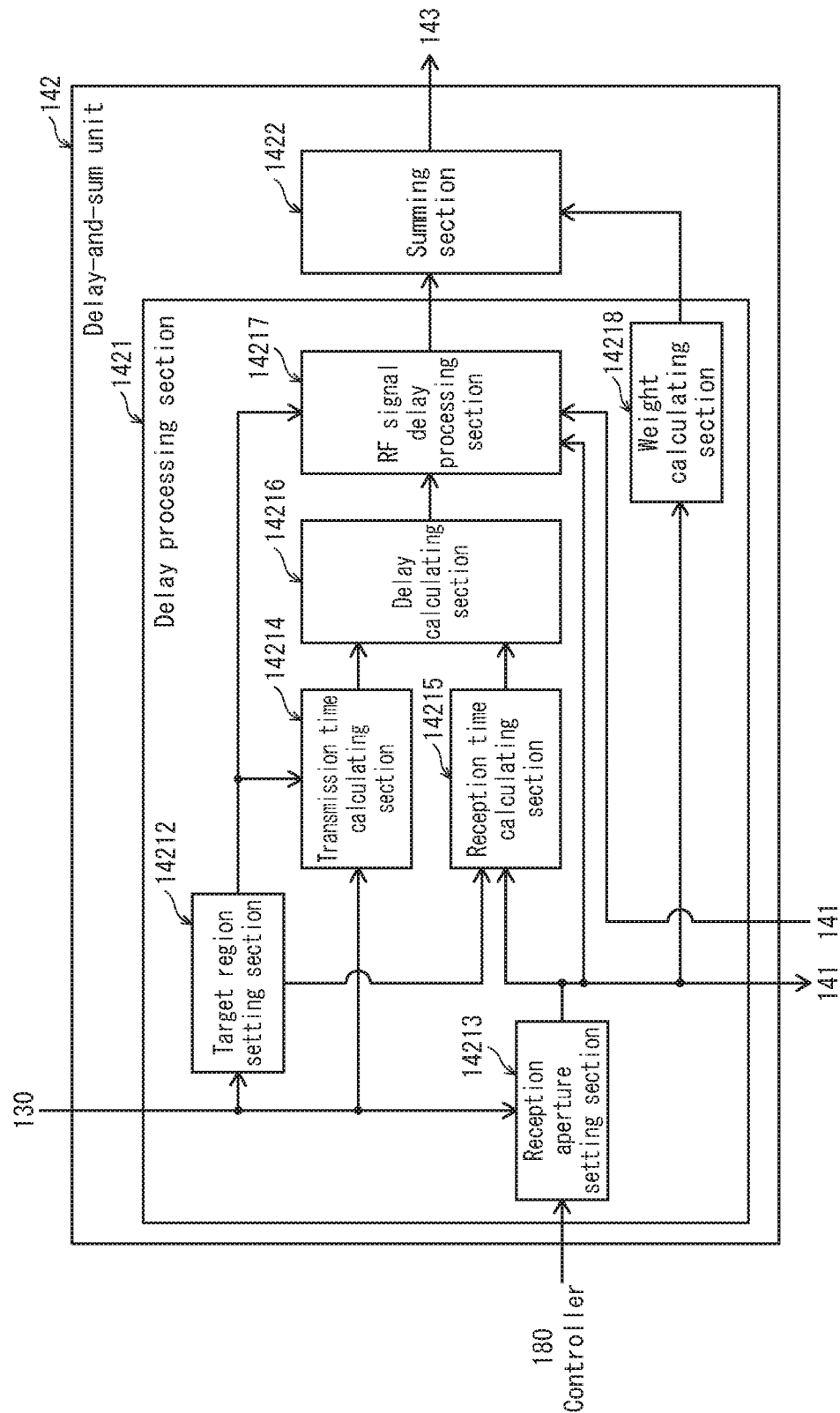
FIG. 5 is a function block diagram of a delay-and-sum unit 142 pertaining to Embodiment 1.

The delay-and-sum unit 142 is a circuit that, corresponding to a transmission event, (i) sets the target region Bx representing a position in the subject for which acoustic line signal line data is generated, and (ii) when an index corresponding to azimuth direction coordinates is i and an index corresponding to depth direction coordinates is j, for each of a plurality of observation points Pij (i=1 to N, j=1 to D) in the target region Bx, performs delay-and-sum calculations in a range of a reception aperture Rx for RF signal sequences received by reception transducers Rw from the observation point Pij, and (iii) generates acoustic line signal line data by calculating acoustic line signals dsij for each observation point Pij. FIG. 5 is a function block diagram illustrating configuration of the delay-and-sum unit 142. In FIG. 5, the delay-and-sum unit 142 includes a delay processing section 1421 and a summing section 1422, the delay processing section 1421 further including a target region setting section 14212, a reception aperture setting section 14213, a transmission time calculating section 14214, a reception time calculating section 14215, a delay calculating section 14216, an RF signal delay processing section 14217, and a weight calculating section 14218.

The following describes elements of the delay-and-sum unit 142.

i) Target Region Setting Section 14212

The target region setting section 14212 sets the target region Bx to generate acoustic line signal line data in the subject. The "target region" is a region of signals for which acoustic line signal line data generation occurs in correspondence with a transmission event, and acoustic line signals dsij are generated with respect to observation points Pij in the target region Bx. The target region Bx is set as a set of target observation points for which acoustic line signal generation is performed and calculation corresponds to one transmission event.

Here, "acoustic line signal line data" is defined as a data set from a set of acoustic line signals dsij with respect to all observation points Pij in the target region Bx generated from one transmission event classified into delay-and-sum results (acoustic line signals dsij) with respect to observation points on lines, such that delay-and-sum results (acoustic line signals dsij) for one line are combined into one sequence. Acoustic line signal line data from different transmission events acquired at different times synthesized with reference to position of an observation point Pij is referred to as acoustic line signal frame data.

The target region setting section 14212 sets the target region Bx, corresponding to a transmission event, based on information indicating position of the transmission aperture Tx acquired from the transmission beamformer 130.

Figure 6:
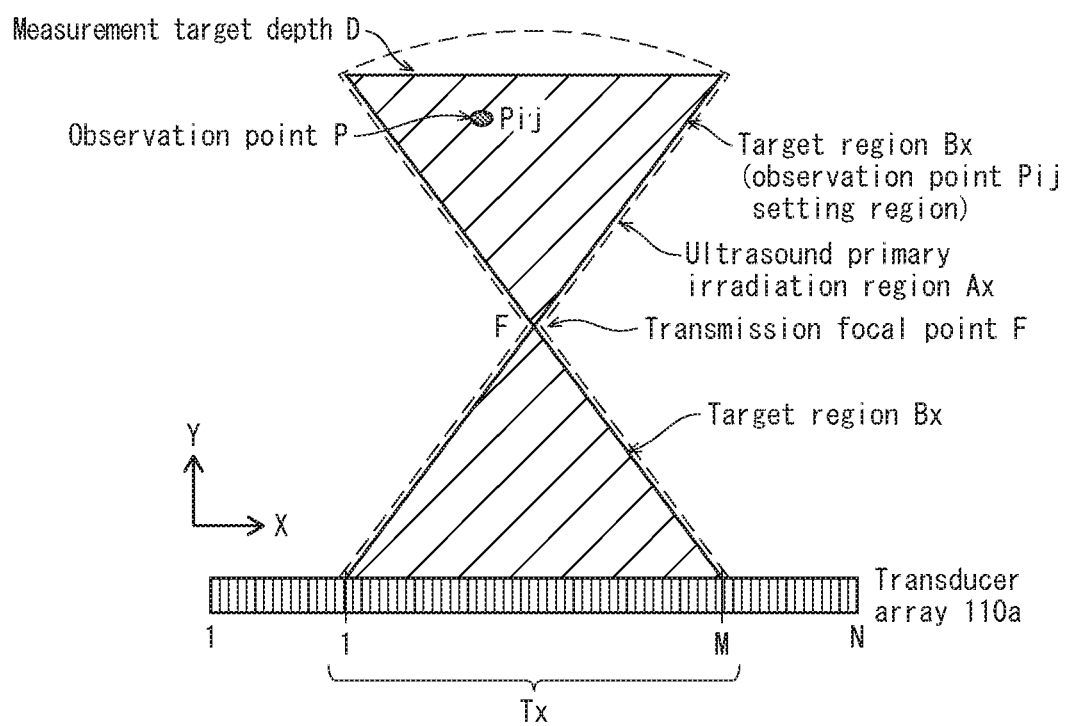
FIG. 6 is a diagram illustrating a range of a target region Bx set by the delay-and-sum unit 142.

FIG. 6 is a schematic diagram illustrating the target region Bx. As illustrated in FIG. 6, the target region Bx exists in the ultrasound primary irradiation region Ax. The target region Bx is, in the ultrasound primary irradiation region Ax, an entire region for which depth is equal or less than the focal depth, and a region for which depth is greater than the focal depth up to a measurement target depth D designated by an operator via the controller 180. Further, a central axis of the target region Bx matches a central axis of the ultrasound primary irradiation region. Note that the target region Bx may be only a portion of the ultrasound primary irradiation region Ax.

The target region Bx that is set is outputted to the transmission time calculating section 14214, the reception time calculating section 14215, and the RF signal delay processing section 14217.

ii) Reception Aperture Setting Section 14213

The reception aperture setting section 14213 is a circuit that sets the reception aperture Rx by selecting reception transducers (reception transducer array) as a portion of the transducers of the probe 110, based on a control signal from the controller 180 and information from the transmission beamformer 130 indicating position of the transmission aperture Tx.

Figure 7:
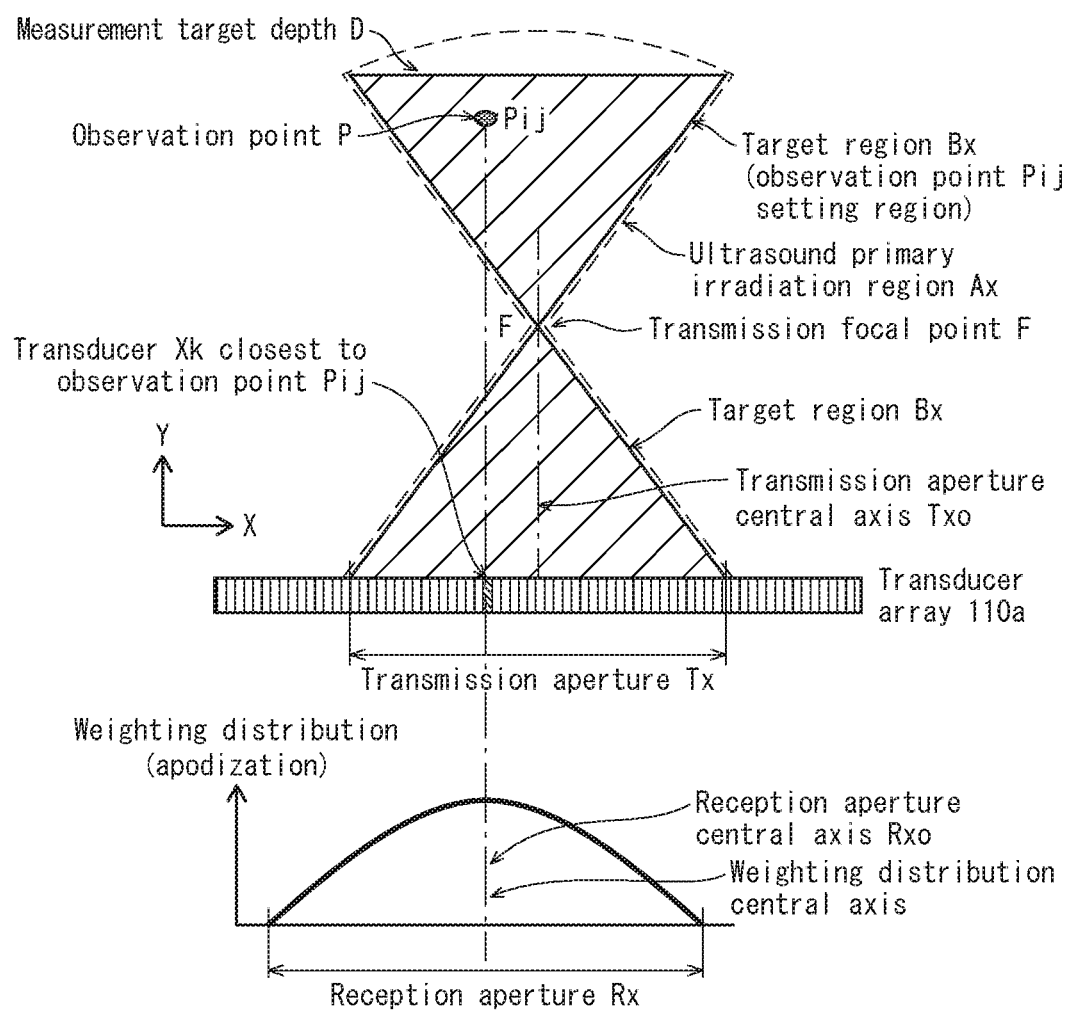
FIG. 7 is a schematic diagram illustrating a relationship between reception aperture Rx as set by reception aperture setter 14213 and transmission aperture Tx.

Here, the reception aperture setting section 14213 selects the reception aperture Rx transducer array such that an array center thereof coincides with a transducer Xk that is spatially closest to an observation point Pij. FIG. 7 is a schematic diagram illustrating a relationship between the transmission aperture Tx and the reception aperture Rx set by the reception aperture setting section 14213. As illustrated in FIG. 7, the reception aperture Rx transducer array is selected such that the array center of the reception aperture Rx transducer array coincides with the transducer Xk that is spatially closest to the observation point Pij. Therefore, even in different transmission events, when generating acoustic line signals for a given observation point Pij in the same position, delay-and-sum is performed based on RF signals obtained by the same reception transducers Rk in the same reception aperture Rx.

Further, a number of transducers included in the reception aperture Rx for receiving reflected waves from the ultrasound primary irradiation region is beneficially set to be at least the number of transducers included in the transmission aperture Tx of the corresponding transmission event. Setting of the reception aperture Rx is performed at least a number of times equal to a maximum number of observation points Pij in the array direction.

Information indicating position of the selected reception aperture Rx is outputted to the data storage 170 via the controller 180.

The data storage 170 outputs information indicating position of the reception aperture Rx and RF signals corresponding to reception transducers to the transmission time calculating section 14214, the reception time calculating section 14215, the RF signal delay processing section 14217, and the weight calculating section 14218.

iii) Transmission Time Calculating Section 14214

The transmission time calculating section 14214 is a circuit that calculates transmission time for a transmitted ultrasound wave to arrive at an observation point P in a subject. On the basis of information indicating the position of transducers included in the transmission aperture Tx acquired from the data storage 170 and information indicating position of the target region Bx acquired from the target region setting section 14212, the transmission time calculating section 14214 calculates time taken for a transmitted ultrasound wave to arrive at an observation point Pij in a subject, for each observation point Pij in the target region Bx.

Figure 8A:
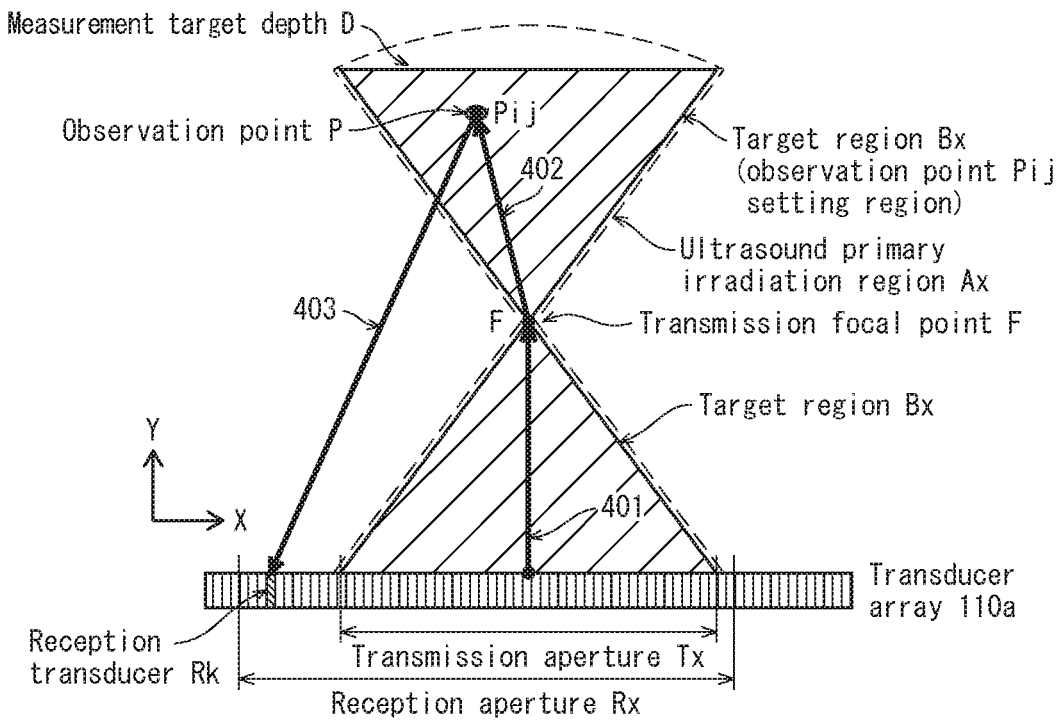
FIG. 8A and FIG. 8B are schematic diagrams illustrating propagation paths of ultrasound arriving at reception transducer Rk from transmission aperture Tx via observation point Pij.
Figure 8B:
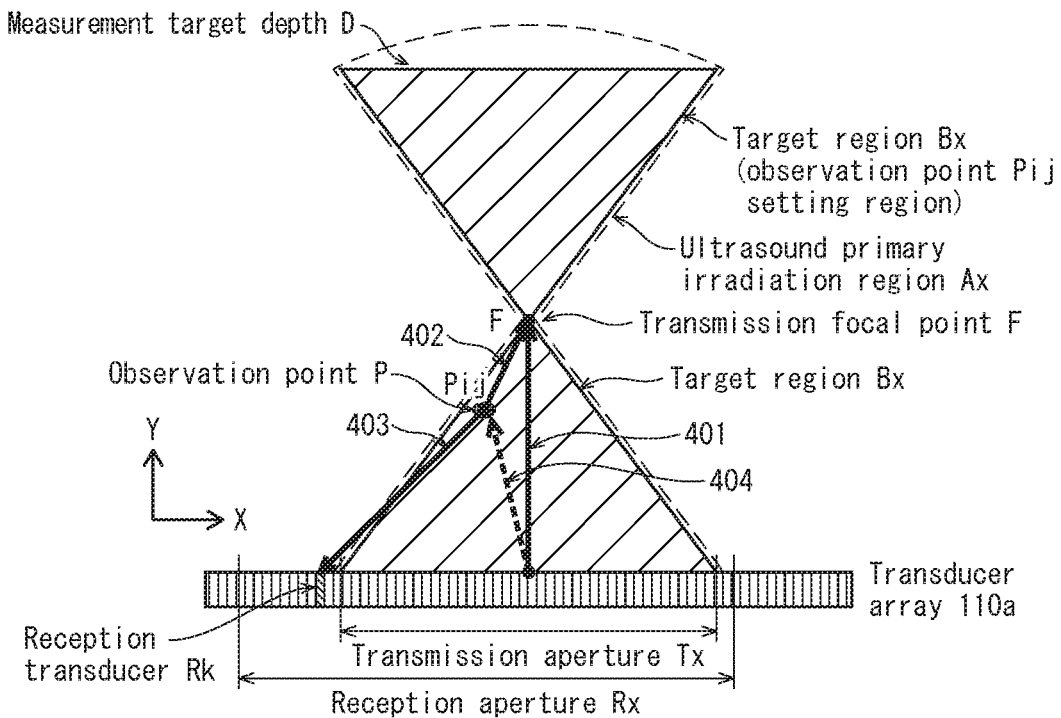

FIG. 8A and FIG. 8B are schematic diagrams illustrating propagation paths of ultrasound arriving at a reception transducer Rk in the reception aperture Rx, reflected from an observation point Pij at a position in the target region Bx and emitted from the transmission aperture Tx. FIG. 8A illustrates a case in which an observation point Pij is deeper than the focal depth, and FIG. 8B illustrates a case in which depth of an observation point Pij is less than the focal depth.

A wavefront of a transmitted wave emitted from the transmission aperture Tx converges at the transmission focal point F via a path 401 then diffuses. A transmitted wave arrives at an observation point Pij while converging or diffusing, and if there is a change in acoustic impedance at the observation point Pij a reflected wave is generated, the reflected wave returning to a reception transducer Rk in the reception aperture Rx of the probe 110. The transmission focal point F is defined as a design value of the transmission beamformer 130, and therefore length of a path 402 between the transmission focal point F and any observation point Pij can be geometrically calculated.

A method of calculating transmission time is described in more detail below.

First, as illustrated in FIG. 8A, when an observation point Pij is deeper than the focal depth, transmission time is calculated assuming that ultrasound emitted from the transmission aperture Tx arrives at the transmission focal point F via the path 401, then arrives at the observation point Pij via the path 402 from the transmission focal point F. Accordingly, a value obtained by summing a travel time along the path 401 and a travel time along the path 402 is the transmission time of a transmission wave. More specifically, for example, a total path length obtained by summing length of the path 401 and length of the path 402 can be divided by propagation speed of ultrasound in a subject in order to obtain the transmission time.

On the other hand, as illustrated in FIG. 8B, when an observation point Pij is shallower than or at an equal depth to the focal depth, transmission time is calculated assuming that, for ultrasound emitted from the transmission aperture Tx, time to arrive at the transmission focal point F via the path 401 and time to arrive at the transmission focal point F from the observation point Pij via a path 404 and the path 402 are equal. In other words, a value obtained by subtracting a travel time of a transmission wave along the path 402 from a travel time along the path 401 becomes the transmission time. More specifically, for example, a path length difference obtained by subtracting length of the path 402 from length of the path 401 can be divided by propagation speed of ultrasound in a subject in order to obtain the transmission time.

The transmission time calculating section 14214 calculates the transmission times for ultrasound to arrive at each observation point Pij in the target region Bx in a subject for one transmission event, and outputs the transmission times to the delay calculating section 14216.

iv) Reception Time Calculating Section 14215

The reception time calculating section 14215 is a circuit that calculates reception time for reflected waves to arrive at each of the reception transducers Rk included in the reception aperture Rx from an observation point P. On the basis of information indicating the position of reception transducers Rk included in the reception aperture Rx acquired from the data storage 170 and information indicating position of the target region Bx acquired from the target region setting section 14212, the reception time calculating section 14215 calculates reception time taken for a transmitted ultrasound wave reflected at observation points Pij in a subject to arrive at each reception transducer Rk of the reception aperture Rx.

As described above, a transmission wave arriving at an observation point Pij generates a reflected wave at the observation point Pij, and the reflected wave returns to reception transducers Rk in the reception aperture Rx of the probe 110. Position information of each reception transducer Rk in the reception aperture Rx is obtained from the data storage 170, and therefore length of a path 403 from any observation point Pij to each reception transducer Rk can be geometrically calculated.

The reception time calculating section 14215 calculates the reception times for transmitted ultrasound reflected at each observation point Pij in the target region Bx to arrive at each reception transducer Rk for one transmission event, and outputs the reception times to the delay calculating section 14216.

v) Delay Calculating Section 14216

The delay calculating section 14216 is a circuit that calculates total propagation time to each reception transducer Rk in the reception aperture Rx from transmission times and reception times, then based on the total propagation times, calculates delay to apply to RF signal sequences corresponding to the reception transducers Rk. The delay calculating section 14216 acquires transmission times for transmitted ultrasound to arrive at observation points Pij and reception times for ultrasound reflected at the observation points Pij to arrive at each reception transducer Rk. The delay calculating section 14216 then calculates total propagation times for transmitted ultrasound to arrive at reception transducers Rk and calculates delay for each of the reception transducers Rk based on differences in total propagation times of the reception transducers Rk. The delay calculating section 14216 calculates, for all observation points Pij in the target region Bx, delay to apply to RF signal sequences corresponding to each reception transducer Rk, and outputs to the RF signal delay processing section 14217.

vi) RF Signal Delay Processing Section 14217

The RF signal delay processing section 14217 is a circuit that identifies, from RF signal sequences with respect to reception transducers Rk of the reception aperture Rx, RF signals corresponding to delays with respect to reception transducers Rk as RF signals corresponding to reception transducers Rk, based on ultrasound reflected from observation points Pij.

In response to a transmission event, the RF signal delay processing section 14217 acquires as input (i) information indicating positions of reception transducers Rk from the reception aperture setting section 14213, (ii) RF signals corresponding to reception transducers Rk from the RF signal storage 1412, (iii) information indicating position of the target region Bx acquired from the target region setting section 14212, and (iv) delay applied to an RF signal sequence with respect to reception transducers Rk from the delay calculating section 14216. From RF signal sequences corresponding to reception transducers Rk, the RF signal delay processing section 14217 identifies RF signals corresponding to times from which delays of reception transducers Rk are subtracted as RF signals based on reflected waves from observation points Pij, and outputs to the summing section 1422.

vii) Weight Calculating Section 14218

The weight calculating section 14218 is a circuit that calculates a weighting sequence (reception apodization) with respect to each reception transducer Rk such that a weight of a transducer positioned at a center of the reception aperture Rx in the array direction is a maximum weight.

Figure 9:
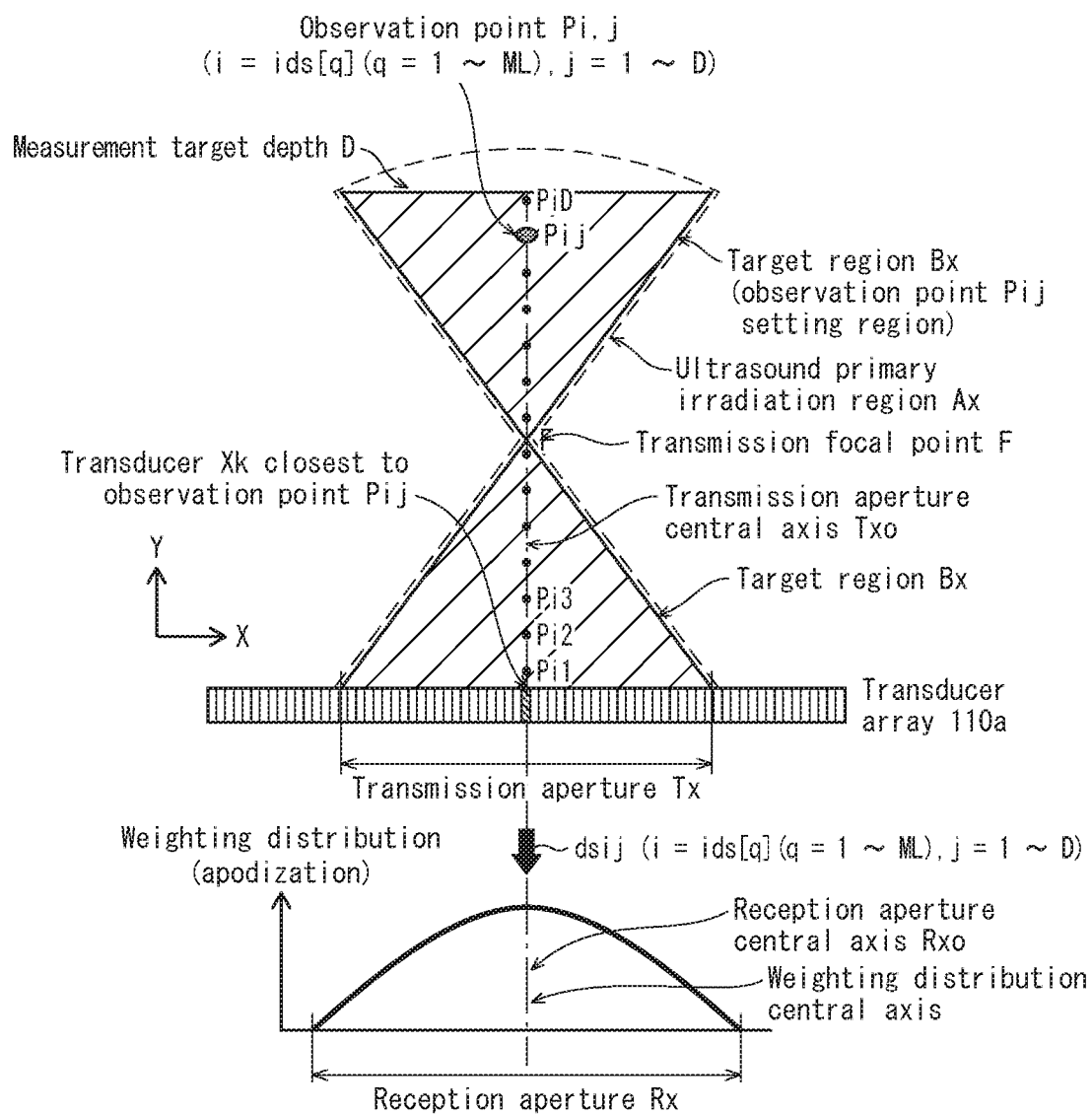
FIG. 9 is a schematic diagram illustrating generation of acoustic line signal line data dsij in a summing section 1422 pertaining to Embodiment 1.

As illustrated in FIG. 9, the weighting sequence is a sequence of weighting coefficients applied to RF signals corresponding to each transducer in the reception aperture Rx. The weighting sequence has a symmetric distribution with the transmission focal point F as a center. As a shape of distribution of the weighting sequence, a Hamming window, a Hann window, a rectangular window, or the like can be used, and the shape of distribution is not limited to any particular example. The weighting sequence is set so that weight for the transducer positioned at the center of the reception aperture Rx is a maximum, and a central axis of weight distribution coincides with a reception aperture central axis Rxo. The weight calculating section 14218 receives information indicating position of reception transducers Rk, outputted from the reception aperture setting section 14213, calculates the weighting sequence with respect to each reception transducer Rk, and outputs to the summing section 1422.

viii) Summing Section 1422

The summing section 1422 is a circuit that receives RF signals identified as corresponding to reception transducers Rk, outputted from the RF signal delay processing section 14217, sums the RF signals, and generates acoustic line signals incorporating delay-and-sum processing with respect to observation points Pij. Alternatively, the summing section 1422 may be configured to receive the weighting sequence with respect to each reception transducer Rk outputted from the weight calculating section 14218, multiply RF signals identified as corresponding to reception transducers Rk by weights corresponding to the reception transducers Rk, and generate acoustic line signals with respect to observation points Pij. The summing section 1422 arranges phases of RF signals detected by reception transducers Rk positioned in the reception aperture Rx by the RF signal delay processing section 14217 to perform summing processing, thereby superimposing RF signals received by reception transducers Rk based on reflected ultrasound from the observation points Pij, thereby increasing signal-to-noise ratio and enabling extraction of RF signals from observation points.

The summing section 1422 generates a set of acoustic line signals dsij for all observation points Pij in the target region Bx in correspondence with a transmission event, i.e., acoustic line signal line data. FIG. 9 is a schematic diagram illustrating generation of acoustic line signal line data dsij by the summing section 1422 (where i=ids[q], q=1 to ML, j=1 to D, ids is an array of coordinates in the azimuth direction, and q is an index identifying acoustic line signal line data). Generated acoustic line signal line data dsij undergoes summing processing, described later, along with stored data outputted to the partial frame memory 1432 in the synthesizer 143, for each transmission event.

Further, ultrasound transmission is repeated while shifting the transmission aperture Tx in the array direction by a movement pitch Mp corresponding to transmission events, and by performing ultrasound transmission from all N of the transducers 110a of the probe 110 a frame acoustic line signal is generated, which is one frame of synthesized acoustic line signals. Acoustic line signals synthesized for each observation point, which constitute frame acoustic line signals, are also referred to herein as "synthesized acoustic line signals".

(5) Synthesizer 143

The synthesizer 143 is a circuit that synthesizes frame acoustic line signals from acoustic line signal line data generated in correspondence with transmission events. The synthesizer 143 sums acoustic line signal line data by using positions of observation points Pij from which acoustic line signals included in acoustic line signal line data are acquired as references, thereby generating synthesized acoustic line signals with respect to each observation point to synthesize frame acoustic line signals. Thus, acoustic line signals with respect to an observation point at the same position in a plurality of acoustic line signal line data are summed to generate a synthesized acoustic line signal.

The synthesizer 143 in FIG. 3 includes a synthesis controller 1431, the partial frame memory 1432 (herein also referred to as "memory 1432"), an address controller 1433, an input/output controller 1434, and an amplification processor 1435.

The following describes elements of the synthesizer 143. In the embodiment below, an example is illustrated in which the movement pitch Mp of transmission transducers for each transmission event is set to one, but of course the movement pitch Mp is not limited to this example.

i) Synthesis Controller 1431, Input/Output Controller 1434, Address Controller 1433

The synthesis controller 1431 acquires acoustic line signal line data from the delay-and-sum unit 142 in a time sequence in an order of transmission events, and outputs to the output controller 1434. Further, the synthesis controller 1431 outputs acoustic line signals to addresses of the memory 1432 specified via the address controller 1433 and performs a summing operation with data stored in the memory 1432. Based on instructions from the synthesis controller 1431, the input/output controller 1434 and the address controller 1433 control input and output of acoustic line signals to and from the memory 1432.

Figure 10A:
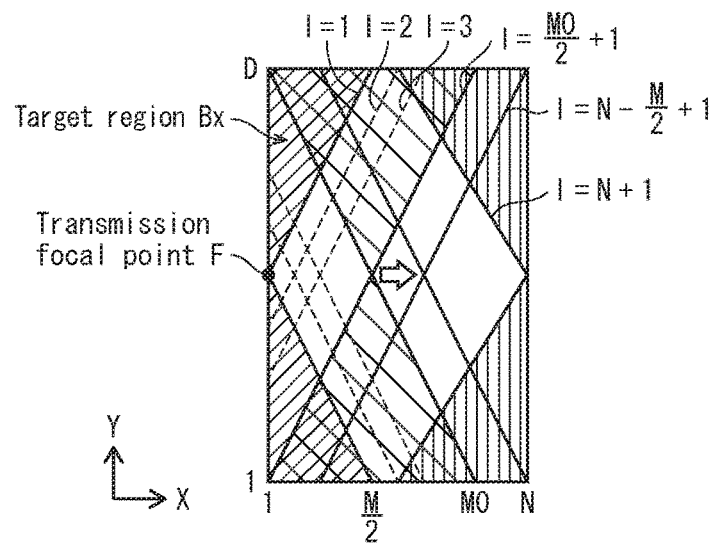
FIGS. 10A, 10B, 10C, 10D, 10E are schematic diagrams illustrating synthesizing of synthesized acoustic line signals in a synthesizer 143 pertaining to Embodiment 1.

FIG. 10A is a schematic diagram illustrating an example in which the target region Bx is shifted gradually in transmission events from 1 to N+1, when the total number of the transducers 110a is N and the number of transmission transducers in the transmission transducer array is M. As illustrated in FIG. 10A, transducers used in a transmission transducer array (transmission aperture Tx) corresponding to transmission events from 1 to N+1, for example, are changed one transducer at a time in the transducer array direction (azimuth direction) as ultrasound transmission is performed sequentially Thus, the target region Bx for different transmission events also changes position by one transducer at a time in the same direction for each transmission event.

Here, in transmission events from 1 to M/2, the number of transducers in a transmission transducer array gradually increases from M/2 to M, one transducer per transmission event. Thereafter, the number of transducers of the transmission transducer array is maintained at M until an (N−M/2+1)th transmission event that reaches the Nth transducer 110a at a far end in the azimuth direction of the transmission transducer array. Thereafter, the number of transducers of the transmission transducer array gradually decreases to M/2 at the (N+1)th transmission event, decreasing by one for each transmission event.

Acoustic line signal data obtained in each transmission event from a first to an (N+1)th transmission event, for example, is superimposed and summed by using positions of observation points Pij from which acoustic line signals included in the acoustic line signal line data are acquired as references, and thereby frame acoustic line signals covering the target region Bx corresponding to the N transducers 110a is synthesized.

The total number of transmission events required for synthesizing a frame acoustic line signal can be appropriately set based on the total number N of the transducers 101a, the number M of the transducers simultaneously driven in the transmission transducer array (transmission aperture Tx), etc. According to the present embodiment, the number of transmission events with respect to N transducers 101a is set as N+1 as one example, but may be N, for example.

FIG. 10B to FIG. 10E are schematic diagrams illustrating acoustic line signal line data generated in transmission events from 1 to (N−M/2+1), correlated with addresses in the azimuth direction of the memory 1432 (hereinafter also referred to as "azimuth address"). In FIG. 10A to FIG. 10E, as an example, the number M of transducers in the transmission transducer array (transmission aperture Tx) equals a maximum value M0 of the azimuth address of the memory 1432.

Figure 10B:
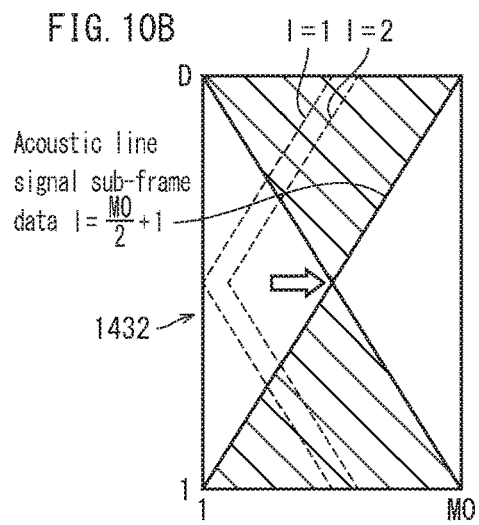

Acoustic line signal line data generated in a first transmission event is correlated with the first to (M/2)th azimuth addresses of the memory 1432, and written to those addresses. Similarly, acoustic line signal line data generated in the (M0/2+1)th transmission event is correlated with the first to (M0)th azimuth addresses of the memory 1432, and data at the addresses is replaced with summing results of summing the acoustic line signal line data with the data at the addresses (FIG. 10B). At this stage, data at all azimuth addresses of the memory 1432 is replaced.

In the (M0/2+2)th transmission event, aside from the last acoustic line signal line data, acoustic line signal line data is similarly summed with data of second through (M0)th azimuth addresses, and the data is replaced. Regarding the last acoustic line signal line data in the azimuth direction, the following processing is performed.

Figure 10D:
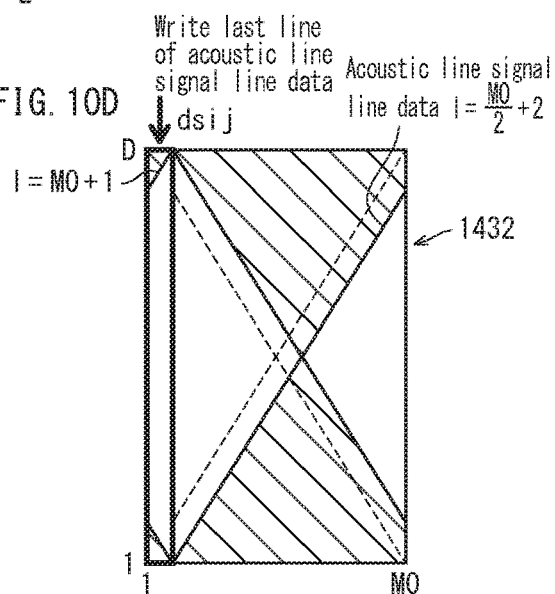
Figure 10C:
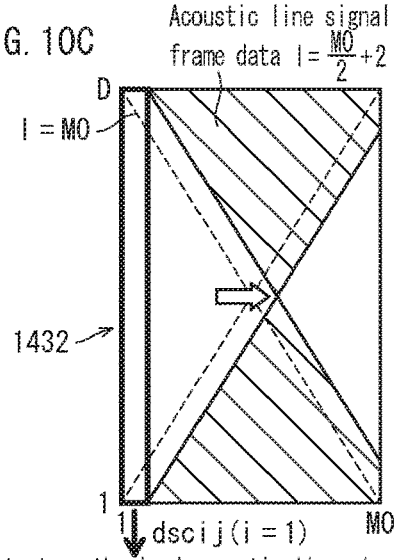

Synthesized acoustic line signal dscij (i=1) at the first azimuth address for which synthesis is already complete in the (M0/2+1)th transmission event is outputted to the ultrasound image generator 150, and data at the first azimuth address is replaced by a value of zero (FIG. 10C). Subsequently, the last acoustic line signal line data dsij in the azimuth direction of the (M0/2+2)th transmission event is correlated with the first azimuth address that has a value of zero, and a result of summing replaces the data (zero) at this address (FIG. 10D).

Figure 10E:
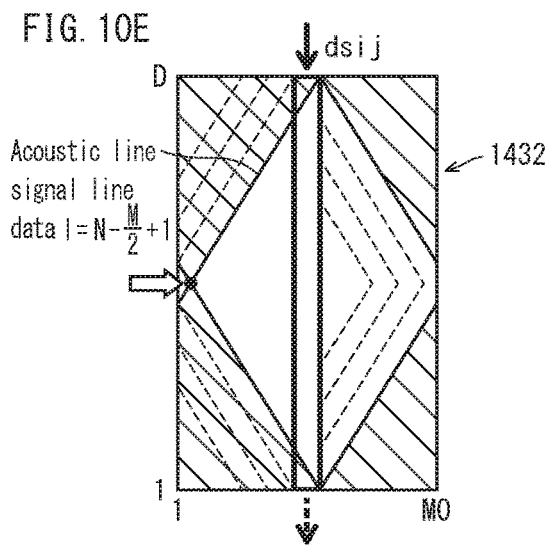

Similarly, in the (N−M/2+1)th transmission event in which an end of the transmission transducer array in the azimuth direction reaches the Nth transducer, synthesized acoustic line signal line data correlated with the same address as the last acoustic line signal line data in the azimuth direction of the (N−M/2)th transmission event for which synthesis is complete is outputted to the ultrasound image generator 150 and data at the address is replaced with zero. Subsequently, the last acoustic line signal line data dsij in the azimuth direction of the (N−M/2+1)th transmission event is correlated with the azimuth address that has a value of zero, and a result of summing replaces the data (zero) at this address (FIG. 10E).

ii) Memory 1432

The memory 1432 is a semiconductor memory. Acoustic line signal line data dsij acquired by different transmission events is added to addresses of the memory 1432 corresponding to positions of observation points Pij, thereby synthesizing synthesized acoustic line signals with respect to each observation point. According to the present embodiment, the RF signal storage 1412 is configured to use the internal semiconductor memory of the FPGA of the reception beamformer 140. The memory 1432 is partitioned into M0 addresses in the transducer array direction (azimuth direction) (where M0 is a natural number, ML≤M0≤N, and M0 is the number of instances of acoustic line signal line data generated in a transmission event) and D addresses in the subject depth direction (where D is a natural number).

For each transmission event, synthesized acoustic line signal line data dscij (j=1 to D) is output to the amplification processor 1435.

ii) Amplification Processor 1435

The amplification processor 1435 is a circuit that uses position of observation points Pij for which acoustic line signals included in acoustic line signal line data is acquired as a reference and performs weighting of synthesized acoustic line signal line data dscij (j=1 to D) outputted by the synthesis controller 1431. In calculating synthesized acoustic line signal line data dscij, values of acoustic line signals in acoustic line signal line data for observation points Pij included across different positions of target regions Bx are summed, and therefore synthesized acoustic line signals have larger values according to the extent of this inclusion. The number of times that a given observation point Pij is included in different target regions Bx is referred to as a "superimposition number" and a maximum value of the superimposition number in the transducer array direction is referred to as a "maximum superimposition number".

FIG. 11A is a schematic diagram indicating maximum superimposition number in synthesized acoustic line signals. As illustrated in FIG. 11A, in synthesized acoustic line signal line data dscij, the value of the superimposition number changes in the depth direction of a subject. The amplification processor 1435, to compensate for this, performs amplification processing multiplying each synthesized acoustic line signal by an amplification factor determined by the number of times summing has been performed in the process of generating the synthesized acoustic line signal.

FIG. 11B is a schematic diagram illustrating an outline of amplification processing in the amplification processor 1435. As illustrated in FIG. 11B, the maximum superimposition number changes in the depth direction of a subject, and therefore in order to compensate for this change, synthesized acoustic line signals are multiplied by amplification factors that change in the depth direction of a subject determined according to maximum superimposition numbers. As a result, a factor of variation of synthesized acoustic line signals due to changes in superimposition number in the depth direction is eliminated, and a value of synthesized acoustic line signals after amplification processing is made uniform in the depth direction.

Further, a process of multiplying synthesized acoustic line signals by an amplification factor that varies in the transducer array direction and is determined according to superimposition number may be performed. In a case in which superimposition numbers vary in the transducer array direction, this factor of variation can be eliminated, and values of synthesized acoustic line signals after amplification processing in the transducer array direction can be made uniform.

iii) Details of Synthesizer 143

The following describes details of processing for synthesizing synthesized acoustic line signal frame data. In the embodiment below, an example is illustrated in which the movement pitch Mp of transmission transducers for each transmission event is set to one, but of course the movement pitch Mp is not limited to this example.

FIG. 12A1 to FIG. 14C2 are schematic diagrams illustrating details of synthesis processing of synthesized acoustic line signals in the synthesizer 143. FIGS. 12A1, 12A2, 13A1, 13A2, 14A1 are schematic diagrams illustrating gradual shifting of the ultrasound primary irradiation region Ax in transmission events when the total number of the transducers 110a is N and a maximum number of transmission transducers in a transmission transducer array is M. FIGS. 12B1, 12B2, 13B1, 13B2, 14B1 are schematic diagrams illustrating gradual shifting of the target region Bx in which observation points Pij for which acoustic line signals are to be generated in transmission events. FIGS. 12C1, 12C2, 13C1, 13C2, 13C3, 14C1, 14C2 are schematic diagrams illustrating superimposition of acoustic line signal line data in the memory 1432 in transmission events.

Further, FIGS. 12A1, 12B1, 12C1 illustrate processing of a first transmission event, FIGS. 12A2, 12B2, 12C2 illustrate processing of a second transmission event, FIGS. 13A1, 13B1, 13C1 illustrate processing of an (M/2+1)th transmission event, FIGS. 13A2, 13B2, 13C2, 13C3 illustrate processing of an (M/2+2)th transmission event, and FIGS. 14A1, 14B1, 14C1, 14C2 illustrate processing of an (N−M/2+1)th transmission event arriving at an Nth transducer at an end in the azimuth direction of the transmission transducer array.

In FIG. 12A1 to FIG. 14C2, as an example, the number M of transducers in the transmission transducer array (transmission aperture Tx) and the maximum value M0 of azimuth addresses of the memory 1432 have a relationship such that M=M0.

First, in a first transmission event such as illustrated in FIGS. 12A1, 12B1, 12C1, the transmitter 131 sets transducers from 1 to M/2 as the transmission aperture Tx, positions the transmission focal point F above the first transducer, and sets a range of the ultrasound primary irradiation region Ax as the hatched area in FIG. 12A1 to a depth D above the transducers from 1 to M/2.

The delay-and-sum unit 142 generates acoustic line signals dsij for observation points Pij in the target region Bx, which is the same range as the ultrasound primary irradiation region Ax, and thereby generates acoustic line signal line data with respect to the target region Bx (FIG. 12B1). At this time, with respect to observation points Pij positioned on acoustic lines along ultrasound beams passing through the ultrasound primary irradiation region Ax, which has a half-hourglass shape through the transmission focal point F, acoustic line signals dsij (black circles "●" in FIG. 12B1) are generated according to intensity of reflected waves. On the other hand, outside the ultrasound primary irradiation region Ax where reflected waves are not obtained, there are no acoustic lines, and therefore observation points Pij are not set and delay-and-sum is not performed (empty circles "○" in FIG. 12B1).

The synthesizer 143 correlates acoustic line signal line data generated in the first transmission event with azimuth addresses from 1 to M/2 and depth direction addresses from 1 to D of the memory 1432, sums with initial values (zero) of the addresses, and replaces data with the results of summing (FIG. 12C1).

Next, as illustrated in FIGS. 12A2, 12B2, 12C2, in the second transmission event, the transmitter 131 sets transducers from 1 to (M/2+1) as the transmission aperture Tx, positions the transmission focal point F above a boundary between the first transducer and the second transducer, and sets a range of the ultrasound primary irradiation region Ax as the hatched area in FIG. 12A2 to the depth D above the transducers from 1 to (M/2+1).

The delay-and-sum unit 142 generates acoustic line signal line data with respect to a new target region Bx, which is the same range as the ultrasound primary irradiation region Ax (FIG. 12B2). For observation points Pij outside the target region Bx, a fixed value indicating zero intensity is set for acoustic line signals dsij.

The synthesizer 143 correlates a portion of acoustic line signal line data generated in the second transmission event excluding the last line with azimuth addresses from 1 to M/2 and depth direction addresses from 1 to D of the memory 1432, sums with data of the addresses of acoustic line signals dsij generated in the first transmission event, and replaces the data with the results of summing (FIG. 12C2). The last line in the azimuth direction of the acoustic line signal line data is correlated with the azimuth address (M/2+1) of the memory 1432, acoustic line signal line data is summed with an initial value (zero) of the address, and the data is replaced with the results of summing (FIG. 12C2).

As illustrated in FIGS. 13A1, 13B1, 13C1, in an (M0/2+1)th transmission event, the transmitter 131 sets transducers from 1 to M0 as the transmission aperture Tx, positions the transmission focal point F above a boundary between the (M0/2)th transducer and the (M0/2+1)th transducer, and sets a range of the ultrasound primary irradiation region Ax as the hatched area in FIG. 13A1 to the depth D above the transducers from 1 to M0.

The delay-and-sum unit 142 generates acoustic line signal line data with respect to the target region Bx, which is the same range as the ultrasound primary irradiation region Ax (FIG. 13B1).

The synthesizer 143 correlates a portion of acoustic line signal line data generated in the (M0/2+1)th transmission event excluding the last line with azimuth addresses from 1 to M0 and depth direction addresses from 1 to D of the memory 1432, sums with data of acoustic line signals dscij generated in the first to (M0/2)th transmission events and stored at the addresses, and replaces the data with the results of summing (FIG. 13C1). The last line in the azimuth direction of the acoustic line signal line data is correlated with the azimuth address M0 of the memory 1432, acoustic line signal line data is summed with an initial value (zero) of the address, and the data at the address is replaced with the result of summing (FIG. 13C1).

Next, as illustrated in FIGS. 13A2, 13B2, 13C2, 13C3, in an (M0/2+2)th transmission event, the transmitter 131 sets transducers from 2 to (M0+1) as the transmission aperture Tx, positions the transmission focal point F above a boundary between the (M0/2+1)th transducer and the (M0/2+2)th transducer, and sets a range of the ultrasound primary irradiation region Ax as the hatched area in FIG. 13A2 to the depth D above the transducers from 2 to (M0+1).

The delay-and-sum unit 142 generates acoustic line signal line data with respect to the target region Bx, which is the same range as the ultrasound primary irradiation region Ax (FIG. 13B1).

The synthesizer 143 correlates a portion of acoustic line signal line data generated in the (M0/2+2)th transmission event excluding the last line with azimuth addresses from 2 to M0 and depth direction addresses from 1 to D of the memory 1432, sums with data of acoustic line signals dscij generated in the first to (M0/2+1)th transmission events and stored at the addresses, and replaces the data with the results of summing (FIG. 13C2).

Next, a synthesized acoustic line signal at the first azimuth address, for which synthesis is already complete in the (M0/2+1)th transmission event, is outputted to the ultrasound image generator 150, and data at the first azimuth address is replaced by a value of zero (FIG. 13C2). Next, the last acoustic line signal line data in the azimuth direction in the (M0/2+2)th transmission event is correlated with the first azimuth address, which has been converted to a zero value (addition correlation address S0), and the result of summing the acoustic line signal line data with the data at the address (zero value) replaces the data at the address (FIG. 13C3).

Next, as illustrated in FIGS. 14A1, 14B1, 14C1, 14C2, in an (N−M/2+1)th transmission event an end in the azimuth direction of the transmission transducers reaches the Nth transducer. In this transmission event, the transmitter 131 sets transducers from (N−M+1) to N as the transmission aperture Tx, positions the transmission focal point F above a boundary between the (N−M/2)th transducer and the (N−M/2+1)th transducer, and sets a range of the ultrasound primary irradiation region Ax as the hatched area in FIG. 14A1 to the depth D above the transducers from (N−M+1) to N.

The delay-and-sum unit 142 generates acoustic line signal line data with respect to the target region Bx, which is the same range as the ultrasound primary irradiation region Ax (FIG. 14B1).

The synthesizer 143 correlates a portion of acoustic line signal line data generated in the (N−M/2+1)th transmission event excluding the last line with azimuth addresses from (N−M0+1) to M0 and (N−M0−1) and depth direction addresses from 1 to D of the memory 1432, sums with data of acoustic line signals dscij generated in the first to (N−M/2)th transmission events and stored at the addresses, and replaces the data with the results of summing (FIG. 14C1).

Next, a synthesized acoustic line signal at the (N−M0)th azimuth address, for which synthesis is already complete in the (N−M/2)th transmission event, is outputted to the ultrasound image generator 150, and data at the (N−M0)th azimuth address is replaced by a value of zero (FIG. 14C1).

Subsequently, the last acoustic line signal line data in the (N−M/2+1)th transmission event is correlated with the (N−M0)th address in the azimuth direction, which has been converted to a zero value (addition correlation address S0), summed with data at the (N−M0)th address, and the result of summing replaces the data at the address (zero value) (FIG. 14C2). Thus, using the probe 110 that has the total number N of the transducers 110a, where the maximum number of transducers in the transmission transducer array in the azimuth direction is M, acoustic line signal line data generated by the first to, for example, the (N+1)th transmission event is synthesized in the memory 1432 using position of observation points Pij as a reference, in order to synthesize synthesized acoustic line signal frame data dsc.

<Operations>

The following describes operations of the ultrasound diagnostic device 100 configured as described above.

Figure 15:
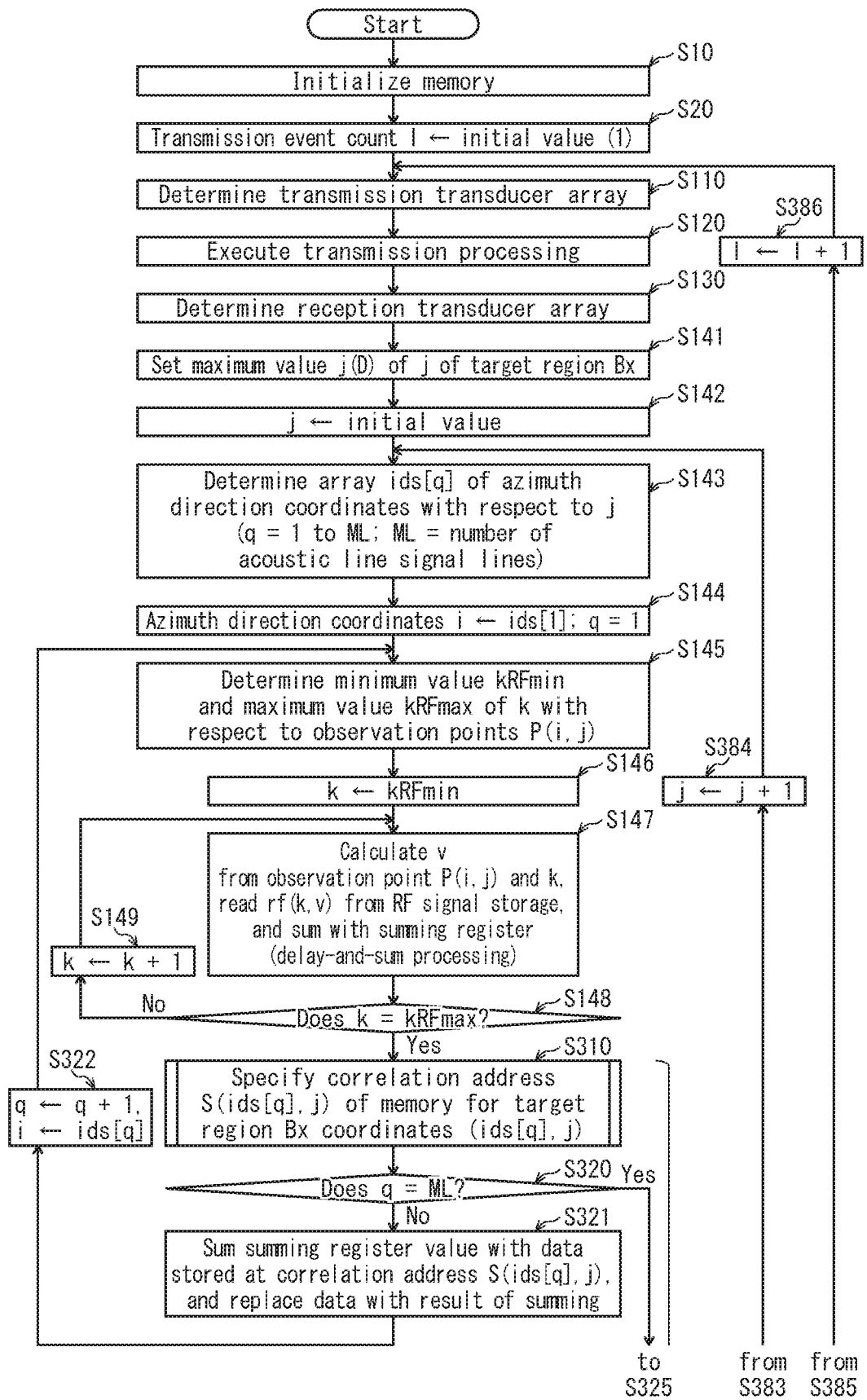
FIG. 15 is a flowchart illustrating beamforming processing of the reception beamformer 140 pertaining to Embodiment 1.
Figure 16:
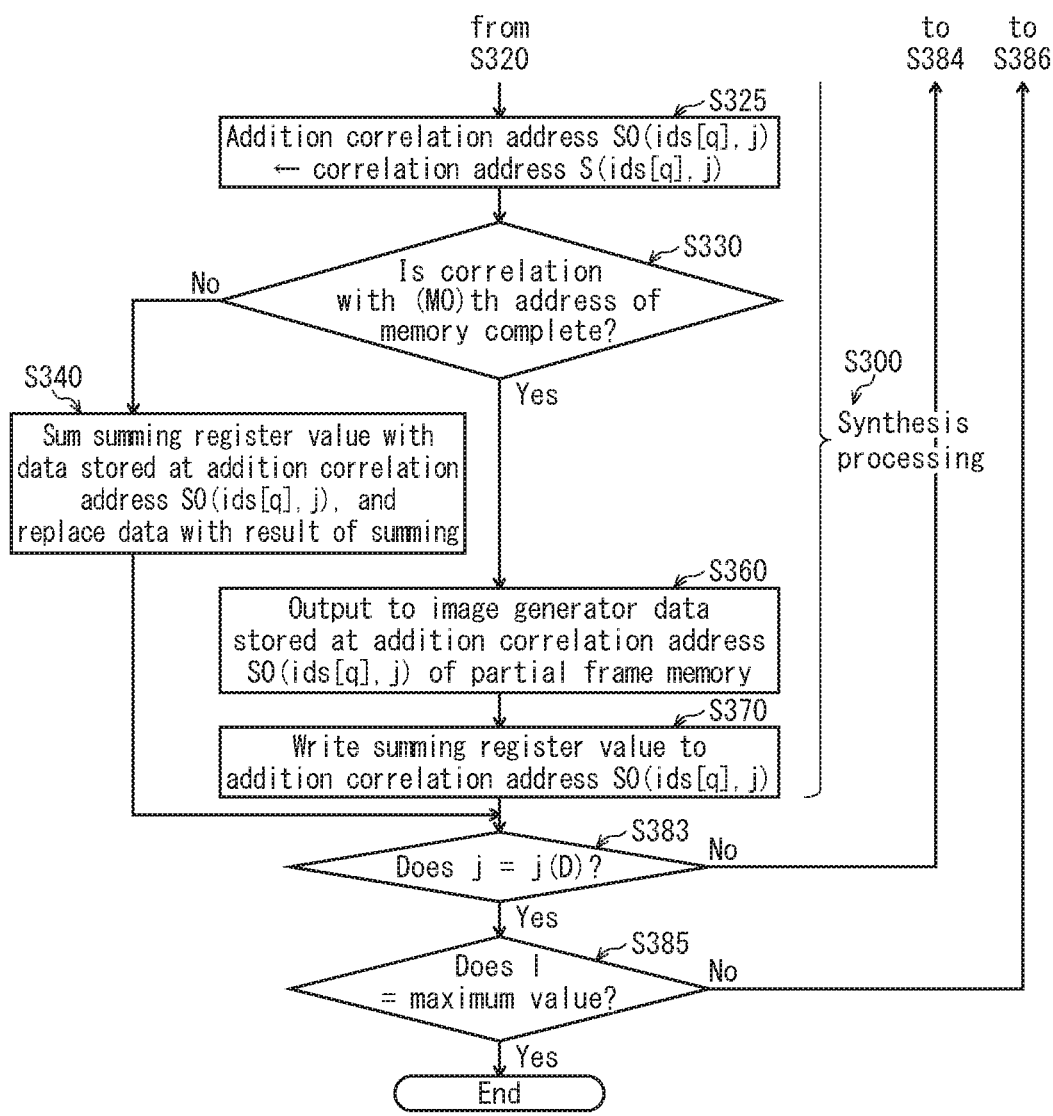
FIG. 16 is a flowchart illustrating beamforming processing of the reception beamformer 140 pertaining to Embodiment 1.

FIGS. 15 and 16 are flowcharts illustrating a beamforming operation of the reception beamformer 140.

First, the RF signal storage 1412 and the memory 1432 are initialized, converting data in all addresses to zero values (step S10), and a transmission event count 1 is initialized as 1 (step S20).

Next, the transmitter 131 determines the transmission aperture Tx from the transducers 110a of the probe 110 (step S110), and performs transmission processing (transmission event) supplying transmission signals for causing transmission of an ultrasound beam from transmission transducers included in the transmission aperture Tx (step S120).

Next, the receiver 141 determines the reception transducer array Rwx from the transducers 110a of the probe 110 (step S130).

Next, a maximum value j (D) is set for j in the target region Bx for which acoustic line signals are to be calculated (step S141) and j is set to an initial value (step S142).

Next, an array ids[q] is determined, each array ids[q] being azimuth direction coordinates of observation points Pij for which acoustic line signals are to be generated corresponding to the depth direction index j (where q=1 to ML, and ML is a number of acoustic line signal line data generated in a transmission event) (step S143), and an index i indicating azimuth direction coordinates corresponding to j is set to an initial value ids[1] (q=1) (step S144).

Next, in step S145, a minimum value kRFmin and a maximum value kRFmax of an index k of the azimuth direction corresponding to observation points P(ij) are determined, and k is set is to the minimum value kRFmin (step S146). Here, k is an index indicating position in the azimuth direction of transducers corresponding to RF signals referenced in delay-and-sum processing of observation points P(ij).

Next, in step S147, v, which corresponds to delay, is calculated from observation points P(ij) and k, and corresponding rf(k,v) is read from the RF signal storage 1412 and added to a summing register (delay-and-sum processing).

Next, it is determined whether k is the maximum value kRFmax (step S148). If less than the maximum value, k is incremented (step S149) and processing returns to step S147. If k is equal to or greater than the maximum value, processing proceeds to step S310. By performing step S147 (delay-and-sum processing) for values of k in the azimuth direction corresponding to observation points P(ij) from the minimum value kRFmin to the maximum value kRFmax, acoustic line signals (delay-and-sum (DAS) data) with respect to observation points P(ij) are added to the summing register.

Figure 17:
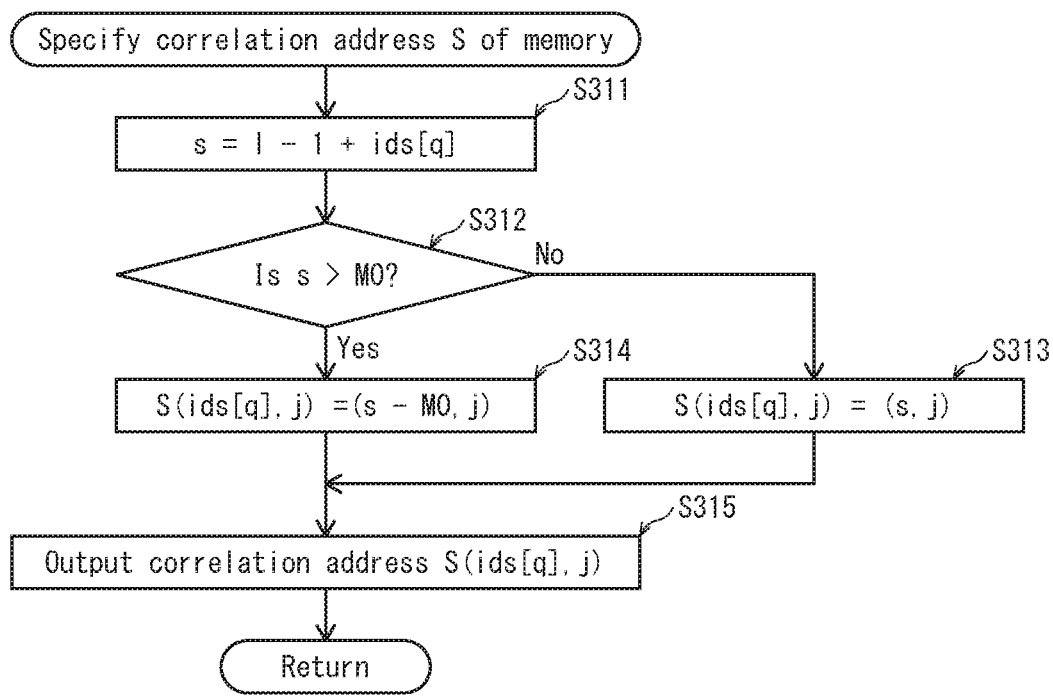
FIG. 17 is a flowchart illustrating details of step S310 in FIG. 15.

Next, in step S310, a correlation address S(ids[q],j) of the memory 1432 is specified for coordinates (ids[q],j) in the target region Bx. FIG. 17 is a flowchart illustrating details of step S310.

First, in step S311, the synthesis controller 1431 calculates a provisional correlation address number s in the azimuth direction from the sum of ids[q] and a value (1−1) obtained by subtracting 1 from the transmission event count 1. Next, whether or not the provisional correlation address number s is greater than the maximum value M0 of azimuth addresses of the memory 1432 is determined (step S312). If greater, that is, if the provisional correlation address number s calculated from ids[q] among the coordinates (ids[q],j) and the value (1−1) obtained by subtracting 1 from the transmission event count 1 is greater than the maximum value M0 of azimuth addresses of the memory 1432, a round-up is necessary to return addresses of the memory 1432 to initial values, and a value obtained by subtracting the maximum value M0 of the azimuth addresses from the provisional correlation address number s in the azimuth direction is newly set as the correlated address number S in the azimuth direction, and this address is set for the correlation address S(ids[q],j) (step S314). If not greater, that is, if the provisional correlation address number s is equal to or less than the maximum value M0 of azimuth addresses of the memory 1432, the value of the provisional correlation address number s becomes the correlation address number S and this address is set for the correlation address S(ids[q],j) (step S313). Finally, the synthesis controller 1431 outputs the correlation address S(ids[q],j) to the address controller 1433 (step S315).

Next, referring back to FIG. 15, whether or not q is the maximum value ML of the number of acoustic line signals in the target region Bx is determined (step S320). If less than the maximum value, the summing register value and data held at the correlation address S(ids[q],j) are summed, and after data is replaced with a summing result (step S321), q is incremented, a new ids[q] is set to i (step S322), and processing returns to step S145. If q is the maximum value M in the target region Bx, in FIG. 16, the correlation address S(ids[q],j) is recognized as the addition correlation address S0(ids[q],j) (step S325), and processing proceeds to step S330. In the following description, the addition correlation address number of the azimuth direction is also referred to as S0.

Next, in step S330, whether or not correlating with the Mth azimuth address of the memory 1432 is complete is determined. If not complete, the summing register value and the data held at the addition correlation address S0(ids[q],j) is summed, the result of summing replaces the data (step S340), and processing proceeds to step S383.

On the other hand, when correlating with the Mth azimuth address is complete, the synthesized acoustic line signal dsc(ids[q],j) held at the addition correlation address S0(ids[q],j) of the memory 1432 for which synthesis processing for prior transmission events is already complete is outputted to the ultrasound image generator 150 (step S360) and the data of the addition correlation address S0(ids[q],j) is converted to a zero value. In step S360, the amplification processor 1435 may perform processing multiplying each synthesized acoustic line signal by amplification factors that are different in the depth direction and determined according to the number of times acoustic line signals are summed in the synthesized acoustic line signal dsc(ids[q],j).

Next, in step S370, the summing register value is written to the addition correlation address S0(ids[q],j). At this stage, acoustic line signals ds(ids[q],j) of observation points P(ij) corresponding to the array ids[q] (q=1 to ML) of all azimuth direction coordinates corresponding to the index j are generated, and are outputted to the memory 1432 for summing with data of corresponding addresses.

Next, whether or not j is the maximum value j (D) in the target region Bx is determined (step S383). If j is less than the maximum value j (D), j is incremented (step S384) and processing returns to step S143 to calculate an acoustic line signal ds(ids[q],j) for an observation point P(ij) corresponding to a new array ids[q]. In this way, by incrementing j and repeating step S147, acoustic line signals ds(ids[q],j) are generated for observation points P(ij) corresponding to the array ids[q] of all azimuth direction coordinates positioned in the target region Bx. If j is the maximum value j(D) in step S383, processing proceeds to step S385.

Next, whether all transmission events have been performed is determined depending on whether or not 1, indicating the transmission event count, is a maximum value (step 385). If not complete, 1 is incremented (step S386), processing returns to step S100, a transmission event is performed, shifting the transmission aperture Tx in the array direction by the movement pitch Mp, the array ids [q] corresponding to j is determined based on a range of the target region Bx obtained from the transmission aperture Tx of the next transmission event (step S143), the reception aperture Rx is set (step S145), and generation of acoustic line signal ds(ids[q],j) (delay-and-sum processing) is performed (step S147). If complete, processing ends.

According to the description above, in step S143, for example, the array ids[q](q=1 to ML) is changed based on j, such that acoustic line signals ds(ids[i],j) are calculated for observation points Pij in a range indicated by black circles "●" in FIG. 13B1. In this case, the target region Bx for which acoustic line signals ds(ids[q],j) are calculated has an hourglass shape.

Alternatively, if a plane wave is used as a transmission wave, the array ids[q](q=1 to ML) may be constant, irrespective of j, such that acoustic line signals ds(ids[q],j) are calculated for observation points Pij in a range indicated by black circles "●" and empty circles "○" in FIG. 13B1. In this case, the target region Bx for which acoustic line signals ds(ids[q],j) are calculated has a rectangular shape.

Note that when a converging wave is used as a transmission wave and the target region Bx is rectangular, reflected waves cannot be obtained from observation points Pij positioned outside the ultrasound primary irradiation region Ax (empty circles "○" in the drawings), and therefore acoustic line signals ds(ids[q],j) for which reflected wave intensity is zero are calculated, and acoustic line signals ds(ids[q],j) having actual intensity values are calculated in a range that has an hourglass shape.

Further, an example has been described in which the movement pitch Mp is 1, but if the movement pitch Mp is two or more, the following processing is performed.

That is, first, in step S311, the synthesis controller 1431 calculates a provisional correlation address number s in the azimuth direction from the sum of ids[q] and a value (1−1) obtained by subtracting 1 from the transmission event count 1.

Next, in step S330, whether or not correlating with the (M0−Mp+1)th azimuth address of the memory 1432 is complete is determined. If not complete, the summing register value and the data held from the addition correlation address S0(ids[q],j) is summed, the result of summing replaces the data, and processing proceeds to step S383.

In step S330, when correlating with the (M0−Mp+1)th azimuth address is complete, in step S360 the synthesized acoustic line signal data dsc(ids[q],j) held at Mp addresses, including the addition correlation address S0(ids[q],j) of the memory 1432 for which synthesis processing for prior transmission events is already complete is outputted to the ultrasound image generator 150, and in step S370 processing writing the summing register value to the Mp addresses including the addition correlation address S0(ids[q],j) is performed.

<Partial Summary>

The reception beamformer 140 pertaining to Embodiment 1 as described above makes use of an ultrasound probe that includes N transducers in the azimuth direction, and includes: the memory 1432 partitioned into M0 azimuth direction×D depth direction addresses, where M0 is a natural number such that ML≤M0≤N and D is a natural number; and the synthesizer 143 that makes a correlation between acoustic line signal line data corresponding to transmission events having a transmission transducer movement pitch Mp and addresses of the memory 1432, using positions of observation points Pij in an ultrasound primary irradiation region Ax as a reference, synthesizes acoustic line signal line data obtained from transmission events by summing acoustic line signals with data stored at correlation addresses S which have been correlated with the acoustic line signals, and generates acoustic line signal frame data having N lines in the azimuth direction.

Further, the synthesizer 143 makes the correlation between the acoustic line signal line data corresponding to transmission events and the addresses of the memory 1432 in an order along the azimuth direction, and when acoustic line signal line data is correlated with an (M0)th address in the azimuth direction of the memory 1432, remaining acoustic line signal line data in the azimuth direction is then correlated in the order along the azimuth direction to addresses starting from a first address in the azimuth direction of the memory 1432, and an address in the azimuth direction of the partial frame memory to which acoustic line signal line data is correlated, counting back Mp lines in the azimuth direction starting at a latest acoustic line signal line data corresponding to the transmission event, is specified as an addition correlation address S0, and values of acoustic line signals correlated with addresses from the first address to an address one before the addition correlation address S0 in the azimuth direction of the memory 1432 are summed with data stored at the addresses, and results of summing are written to the addresses, and with respect to Mp addresses starting at and including the addition correlation address S0 in the order along the azimuth direction of the memory 1432, after outputting to the ultrasound image generator 150 data stored at the Mp addresses, writes values of corresponding acoustic line signals to the Mp addresses.

Further, the synthesizer 143 outputs to the ultrasound image generator 150 the data stored at the Mp addresses after writing to an address one before the addition correlation address S0 in the azimuth direction of the partial frame memory 1432 the results of summing a value of an acoustic line signal corresponding to the address with data stored at the address.

According to this configuration, in the ultrasound diagnostic device 100 including the reception beamformer 140, in the reception beamforming using the synthetic aperture method, acoustic line signal frame data of a total number of lines N of the azimuth direction can be synthesized by using the partial frame memory 1432 in which the azimuth direction address M0 is less than total channel number corresponding to the total number N of the transducers 110a. Thus, it is possible to reduce frame memory capacity required for synthesis processing in comparison to conventional art, while suppressing a reduction in spatial resolution and signal-to-noise ratio.

Further, the delay-and-sum unit 142 and the synthesizer 143 are included in the first integrated circuit 140, the memory 1432 is SRAM included in the first integrated circuit 140, the ultrasound image generator 150 is included in the second integrated circuit that is different from the first integrated circuit 140, and output of the acoustic line signal line data by the synthesizer 143 from the first integrated circuit 140 to the second integrated circuit corresponds to transmission events.

According to this configuration, there is no need to provide a large scale SRAM in an FPGA, and the hardware cost of the FPGA can be reduced. Further, internal memory of the FPGA is used as a frame memory for synthesis processing, and therefore it is not necessary to provide a large capacity DDR memory for synthesis processing. Accordingly, data transfer between FPGA and DDR memory does not occur, and it is not necessary to provide a memory controller in the FPGA that has a high processing capability that can perform high speed data transfer.

Further, data transfer from the first integrated circuit that includes the synthesizer 143 to the second circuit that includes the ultrasound image generator 150 is performed per transmission event in units of synthesized acoustic line signal line data dscij (j=1 to D), and therefore bus capacity required for data transfer between integrated circuits can be reduced.

As a result, delay-and-sum from reception of echo signals, and reception beamforming processing up until synthesis processing of acoustic line signal frame data can be realized by using only internal memory of small-scale FPGAs, and it becomes possible to reduce hardware costs in comparison to conventional art.

Embodiment 2

According to Embodiment 1, the synthesizer 143, with respect to a gradual transducer pitch Mp of the transmission transducer array of transmission events, when an azimuth direction address of the memory 1432 to which acoustic line signal line data one Mp pitch from a last transmission event is correlated is set as the addition correlation address S0, after summing and writing results of values of the acoustic line signals correlated with an address one prior to the addition correlation address S0 with data stored in the address one prior, outputs data stored at the Mp addresses including the addition correlation address S0 in the azimuth direction of the memory 1432 to the ultrasound image generator 150.

However, output of data stored at the Mp addresses from the addition correlation address S0 to the ultrasound image generator 150 may be performed before updating data at an address one before the addition correlation address S0. According to Embodiment 2, the synthesizer 143 is different from Embodiment 1 in that, after specifying the addition correlation address S0 corresponding to (Mp)th acoustic line signal line data from a last transmission event and before determining whether or not a result of summing a value of acoustic line signal correlated with an address one prior to the addition correlation address S0 and data stored at the address has been written, the synthesizer 143 outputs data stored at the Mp addresses from the addition correlation address S0 in the azimuth direction to the ultrasound image generator 150.

The following describes operations of the synthesizer 143 of the ultrasound diagnostic device pertaining to Embodiment 2.

According to Embodiment 2, configuration of a reception beamformer is the same as that of the reception beamformer 140 pertaining to Embodiment 1, illustrated in FIG. 3. In the ultrasound diagnostic device pertaining to Embodiment 2, in operation of the synthesizer 143, a processing method for determining output of data stored at an (S0)th address to the ultrasound image generator 150 and output timing are different to Embodiment 1. Thus, only differences in operation are described. Structure and other operations are the same as in Embodiment 1, and therefore the same reference symbols are used and redundant description is omitted.

<Processing of Synthesizer 143>

The following describes details of processing for synthesizing synthesized acoustic line signal frame data. In the embodiment below, an example is illustrated in which the movement pitch Mp of transmission transducers for each transmission event is set to one, but of course the movement pitch Mp is not limited to this example.

FIG. 18A1 to FIG. 20D are schematic diagrams illustrating details of synthesis processing of synthesized acoustic line signals in the synthesizer 143 according to Embodiment 2. FIGS. 18A1, 18A2, 19A1, 19A2, 20A are schematic diagrams illustrating gradual shifting of the ultrasound primary irradiation region Ax in transmission events when the total number of the transducers 110*a* is N and a maximum number of transmission transducers in a transmission transducer array is M. FIGS. 18B1, 18B2, 19B1, 19B2, 20B are schematic diagrams illustrating output to the ultrasound image generator 150 of data stored at an (S0)th address of the memory 1432 in each transmission event. FIGS. 18C1, 18C2, 19C1, 19C2, 20C are schematic diagrams illustrating gradual shifting of the target region Bx in which observation points Pij for which acoustic line signals are to be generated in transmission events. FIGS. 18D1, 18D2, 19D1, 19D2, 20D are schematic diagrams illustrating superimposition of acoustic line signal line data in the memory 1432 in transmission events.

Further, FIGS. 18A1, 18B1, 18C1, 18D1 illustrate processing of a first transmission event, FIGS. 18A2, 18B2, 18C2, 18D2 illustrate processing of a second transmission event, FIGS. 19A1, 19B1, 19C1, 19D1 illustrate processing of an (M/2+1)th transmission event, FIGS. 19A2, 19B2, 19C2, 19D2 illustrate processing of an (M/2+2)th transmission event, and FIGS. 20A, 20B, 20C, 20D illustrate processing of an (N−M/2+1)th transmission event arriving at an Nth transducer at an end in the azimuth direction of the transmission transducer array.

In FIG. 18A1 to FIG. 20D, as an example, the number M of transducers in the transmission transducer array (transmission aperture Tx) and the maximum value M0 of azimuth addresses of the memory 1432 have a relationship such that M=M0.

First, in a first transmission event such as illustrated in FIGS. 18A1, 18B1, 18C1, 18D1, as in Embodiment 1, the transmitter 131 sets transducers from 1 to M/2 as the transmission aperture Tx, positions the transmission focal point F above the first transducer, and sets a range of the ultrasound primary irradiation region Ax as the hatched area in FIG. 18A1 to a depth D above the transducers from 1 to M/2.

In the first transmission event, the last acoustic line signal line data in the azimuth direction of the target region Bx is correlated with addresses up to a max(ids[q])th address in the azimuth direction of memory 1432. Among these correlated azimuth addresses, a maximum azimuth address max(ids[q]) is specified as an addition correlation address S0, and data stored at the addition correlation address S0 is outputted to the ultrasound image generator 150 and a zero value is written to the addition correlation address S0 (FIG. 18B1). Note that in the first transmission event after a start of reception beamforming, the memory 1432 is initialized at the start of the reception beamforming, as described later, and therefore at this point a zero value is outputted to the ultrasound image generator 150.

As per Embodiment 1, the delay-and-sum unit 142 generates acoustic line signals dsij for observation points Pij in the target region Bx, which is the same range as the ultrasound primary irradiation region Ax, and thereby generates acoustic line signal line data with respect to the target region Bx (FIG. 18C1).

The synthesizer 143 correlates acoustic line signal line data generated in the first transmission event with azimuth addresses from 1 to M/2 and depth direction addresses from 1 to D of the memory 1432, sums with data (zero values) at the addresses, and replaces the data with the results of summing (FIG. 18D1).

Next, as illustrated in FIGS. 18A2, 18B2, 18C2, 18D2, in the second transmission event, as per Embodiment 1, the transmitter 131 sets transducers from 1 to (M/2+1) as the transmission aperture Tx, positions the transmission focal point F above a boundary between the first transducer and the second transducer, and sets a range of the ultrasound primary irradiation region Ax as the hatched area in FIG. 12A2 to the depth D above the transducers from 1 to (M/2+1).

Next, in the second transmission event, the last acoustic line signal line data in the azimuth direction of the target region Bx is correlated with addresses up to a max(ids[q])th address in the azimuth direction of memory 1432. Among these correlated azimuth addresses, a maximum azimuth address max(ids[q]) is specified as an addition correlation address S0, and when data stored at the addition correlation address S0 is outputted to the ultrasound image generator 150, a zero value is written to the addition correlation address S0 (FIG. 18B2).

Next, the delay-and-sum unit 142 generates acoustic line signal line data with respect to the target region Bx, which is the same range as the ultrasound primary irradiation region Ax (FIG. 18C2).

The synthesizer 143 correlates a portion of acoustic line signal line data generated in the second transmission event excluding a last line with azimuth addresses from 1 to (M/2) and depth direction addresses from 1 to D of the memory 1432, summing data of the addresses of acoustic line signals dsij generated in the first transmission event, and replaces the data with the results of summing (FIG. 18D2). The last line in the azimuth direction of the acoustic line signal line data is correlated with the azimuth address (M/2+1) of the memory 1432, summed with data (zero value) of the address, and the data is replaced with the result of summing Next, as illustrated in FIGS. 19A1, 19B1, 19C1, 19D1, in an (M0/2+1)th transmission event, the transmitter 131 sets transducers from 1 to M0 as the transmission aperture Tx, positions the transmission focal point F above a boundary between the (M0/2)th transducer and the (M0/2+1)th transducer, and sets a range of the ultrasound primary irradiation region Ax as the hatched area in FIG. 19A1 to the depth D above the transducers from 1 to M.

Next, the last acoustic line signal line data in the azimuth direction of the target region Bx is correlated with addresses up to M0 in the azimuth direction. Among these correlated azimuth addresses, a maximum azimuth address M0 is specified as an addition correlation address S0, data stored at the addition correlation address S0 is outputted to the ultrasound image generator 150, and a zero value is written to the addition correlation address S0 (FIG. 19B1).

The delay-and-sum unit 142 generates acoustic line signal line data with respect to the target region Bx, which is the same range as the ultrasound primary irradiation region Ax (FIG. 19C1).

The synthesizer 143 correlates a portion of acoustic line signal line data generated in the (M0/2)th transmission event excluding a last line with azimuth addresses from 1 to (M0−1) and depth direction addresses from 1 to D of the memory 1432, summing with data of acoustic line signals dscij generated in the first to (M0/2)th transmission events and stored in the addresses, and replaces the data with the results of summing (FIG. 19D1). The last acoustic line signal line data is correlated with the (M0) azimuth address of the memory 1432, summed with an initial value (zero) of the address, and the initial value is replaced with the result of summing Next, as illustrated in FIGS. 19A2, 19B2, 19C2, 19D2, in an (M0/2+2)th transmission event, the transmitter 131 sets transducers from 2 to (M0+1) as the transmission aperture Tx, positions the transmission focal point F above a boundary between the (M0/2+1)th transducer and the (M0/2+2)th transducer, and sets a range of the ultrasound primary irradiation region Ax as the hatched area in FIG. 19A2 to the depth D above the transducers from 2 to (M0+1).

The last acoustic line signal line data in the azimuth direction of the target region Bx in the (M0/2+2)th transmission event is correlated with addresses up to the (M0)th address and also the first address in the azimuth direction of the memory 1432. Among the correlated azimuth addresses, a greatest azimuth address "1" is specified as the addition correlation address S0. That is, in the (M0/2+1)th transmission event, the target region Bx is already correlated with the first to (M0)th azimuth addresses of the memory 1432. Thus, in this processing, correlation is performed up to the first azimuth address of the memory 1432, which was correlated earliest in the processing. Next, a synthesized acoustic line signal at the first azimuth address, for which synthesis is already complete in the (M0/2+1)th transmission event, is outputted to the ultrasound image generator 150, and a zero value is written to the first azimuth address (addition correlation address S0) (FIG. 19B1).

The delay-and-sum unit 142 generates acoustic line signal line data with respect to the target region Bx, which is the same range as the ultrasound primary irradiation region Ax (FIG. 19C2).

The synthesizer 143 correlates acoustic line signal line data generated in the (M0/2+2)th transmission event with azimuth addresses from 2 to M0 and depth direction addresses from 1 to D of the memory 1432. Acoustic line signal line data other than a last line is summed with data of synthesized acoustic line signals dscij generated in first to (M0/2+1)th transmission events stored at azimuth addresses from 2 to M0, and this data is replaced by the results of summing. The last line of acoustic line signal line data of the (M/2+2)th transmission event is correlated with the first azimuth address (addition correlation address S0) that has been converted to a zero value, summed with data at the address, and this data is replaced by the results of summing (FIG. 19D2).

Next, as illustrated in FIGS. 20A, 20B, 20C, 20D, in an (N−M/2+1)th transmission event an end in the azimuth direction of the transmission transducers reaches the Nth transducer. In this transmission event, the transmitter 131 sets transducers from (N−M+1) to N as the transmission aperture Tx, positions the transmission focal point F above a boundary between the (N−M/2)th transducer and the (N−M/2+1)th transducer, and sets a range of the ultrasound primary irradiation region Ax as the hatched area in FIG. 20A to the depth D above the transducers from (N−M+1) to N.

Figure 20A:
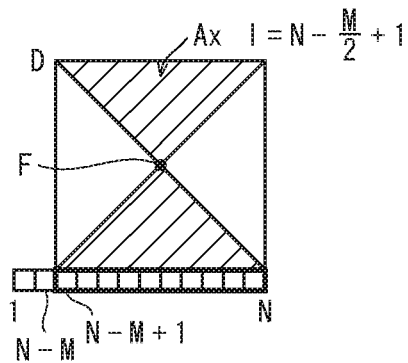
FIGS. 20A, 20B, 20C, 20D are schematic diagrams illustrating synthesizing of synthesized acoustic line signals by the synthesizer 143 pertaining to Embodiment 2 for an Nth transmission event.
Figure 20B:
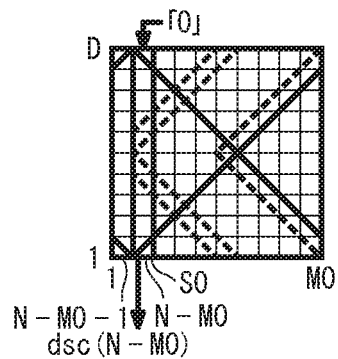

A last acoustic line signal line data in the azimuth direction of the target region Bx in the (N−M/2+1)th transmission event is correlated with addresses up to the (M0) the address of the memory 1432 in the azimuth direction and returning to the start, the first to (M−M0)th addresses. Among the correlated azimuth addresses, a latest azimuth address (M−M0) is specified as the addition correlation address S0. That is, in the (N−M/2)th transmission event, the target region Bx is already correlated with addresses of the memory 1432 from (N−M0+1) to M0, and from 1 to (N−M0−1). Thus, in this processing, new correlation is performed with respect to the (N−M0)th azimuth address of the memory 1432, which was correlated earliest in the processing. A synthesized acoustic line signal at the (N−M0) th azimuth address (addition correlation address S0) for which synthesis processing is already complete in the (N−M/2)th transmission event is outputted to the ultrasound image generator 150, and a zero value is written to the (N−M0) the azimuth address (FIG. 20B).

Figure 20C:
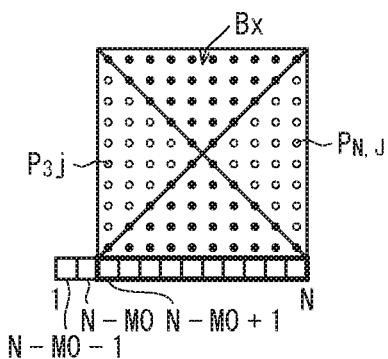

The delay-and-sum unit 142 generates acoustic line signal line data with respect to the target region Bx, which is the same range as the ultrasound primary irradiation region Ax (FIG. 20C).

The synthesizer 143 correlates acoustic line signal line data generated in the (N−M/2+1)th transmission event with azimuth addresses from (N−M0+1) to M0 and from 1 to (N−M0−1) and depth direction addresses from 1 to D of the memory 1432.

Figure 20D:
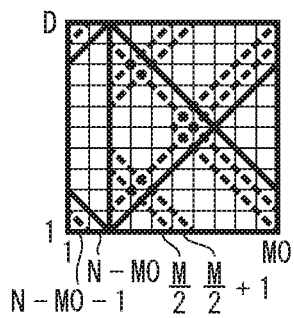

Acoustic line signal line data other than a last line is summed with data of synthesized acoustic line signals dscij generated in transmission events 1 to (N−M/2) stored at azimuth addresses (N−M0+1) to M0 and 1 to (N−M0−1), and the data is replaced by the results of summing (FIG. 20D).

The last acoustic line signal line data in the (N−M/2+1)th transmission event is correlated with the (N−M0)th address in the azimuth direction, which has been converted to a zero value (addition correlation address S0), summed with data at addresses correlated up to transmission event (N−M0), and the result of summing replaces the data at the address (FIG. 20D).

Thus, using the probe 110 that has the total number N of the transducers 110a, where the maximum number of transducers in the transmission transducer array in the azimuth direction is M, acoustic line signal line data generated by the first to the (N+1)th transmission events is synthesized in the memory 1432, which has M0 azimuth direction addresses, using position of observation points Pij as a reference, in order to synthesize synthesized acoustic line signal frame data dsc.

<Operations>

Figure 21:
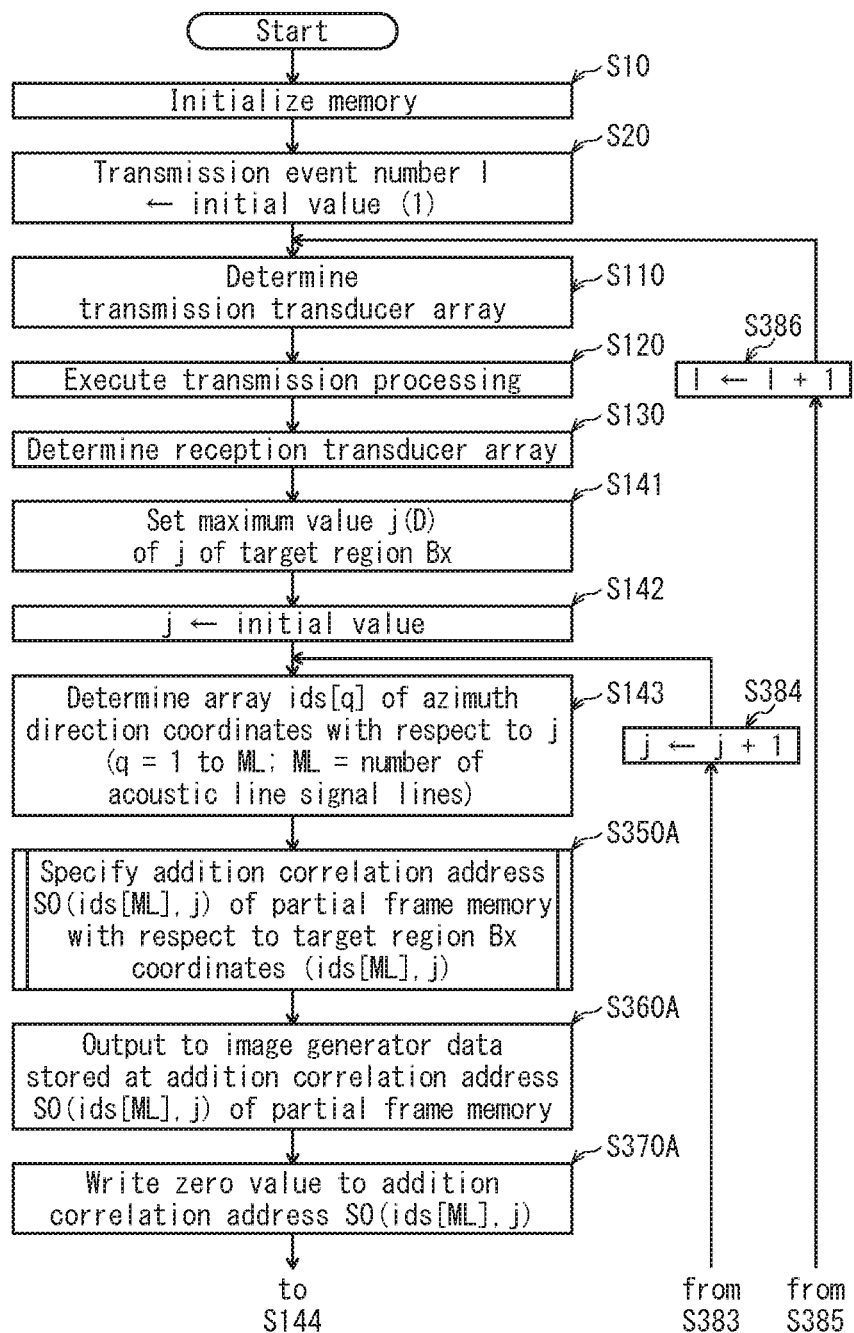
FIG. 21 is a flowchart illustrating beamforming processing of the reception beamformer 140 pertaining to Embodiment 2.
Figure 22:
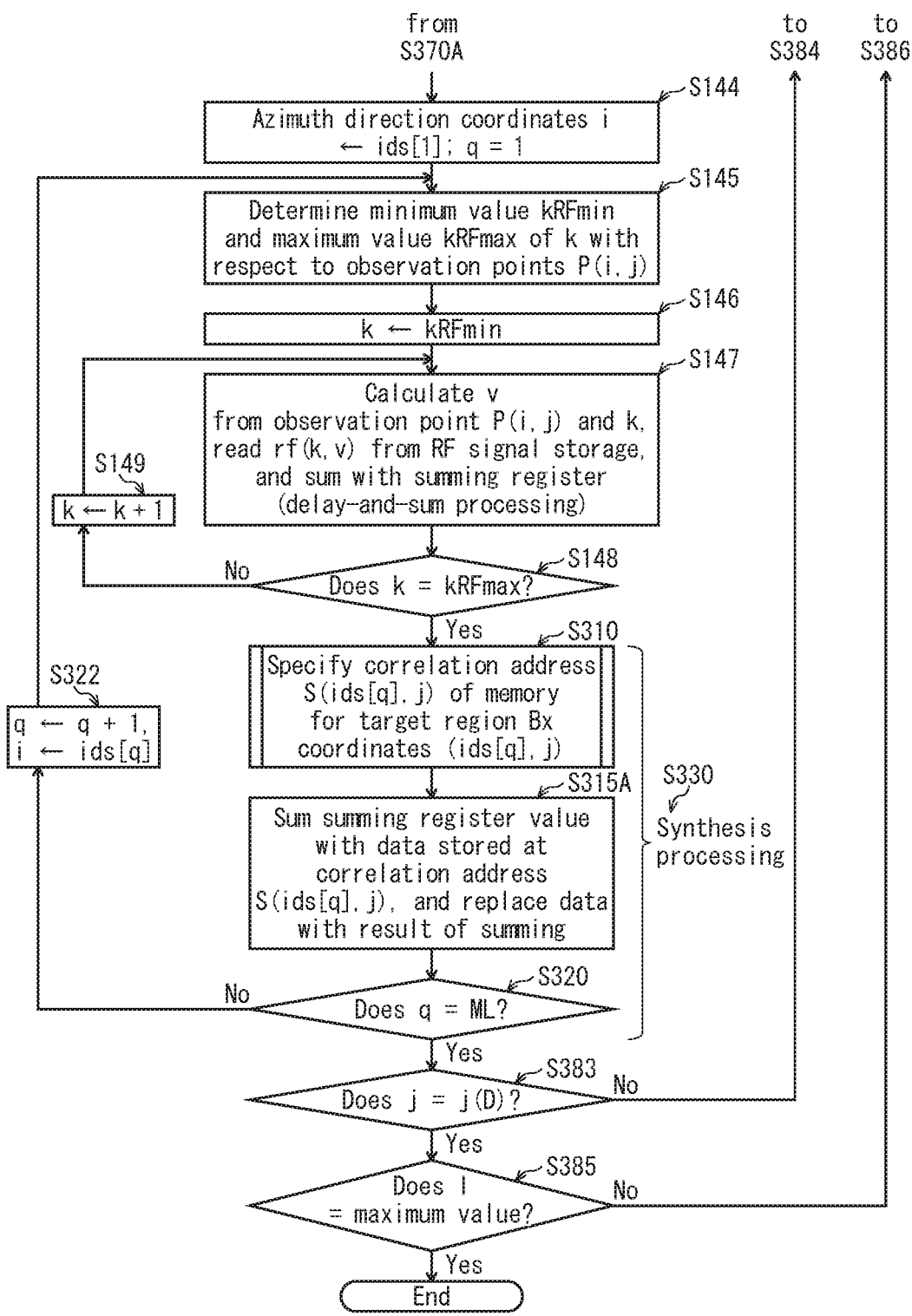
FIG. 22 is a flowchart illustrating beamforming processing of the reception beamformer 140 pertaining to Embodiment 2.

The following describes operations of the ultrasound diagnostic device 100 pertaining to Embodiment 2. FIGS. 21 and 22 are flowcharts illustrating beamforming processing of the reception beamformer 140 pertaining to Embodiment 2.

In the flowchart pertaining to Embodiment 2, steps S315A, S350A, S360A, S370A are different from operations of Embodiment 1 illustrated in FIGS. 15 and 16, while the processing of steps S10, S20, S110 to S149, and S310 to S386 is the same as the steps of Embodiment 1 illustrated in FIGS. 15 and 16 and description thereof is simplified or omitted here.

First, the RF signal storage 1412 and the memory 1432 are initialized, converting data at all addresses to zero values (step S10), and a transmission event count 1 is initialized as 1 (step S20).

Next, the transmitter 131 determines the transmission aperture Tx (step S110) and performs transmission processing with respect to each transmission transducer (transmission event) (step S120).

Next, the receiver 141 determines the reception transducer Rwx (step S130), sets a maximum value j(D) of j in the target region Bx for which acoustic line signals are to be calculated (step S141), and sets j to an initial value (step S142).

Next, an array ids[q] of azimuth direction coordinates of observation points Pij for which acoustic line signals are to be generated corresponding to the depth direction index j is determined (where q=1 to ML, and ML is a number of acoustic line signal line data) (step S143).

Next, in step S350A, an azimuth address (addition correlation address S0(ids[ML],j)) of the memory 1432 is specified for coordinates (ids[ML],j) in the target region Bx.

Figure 23:
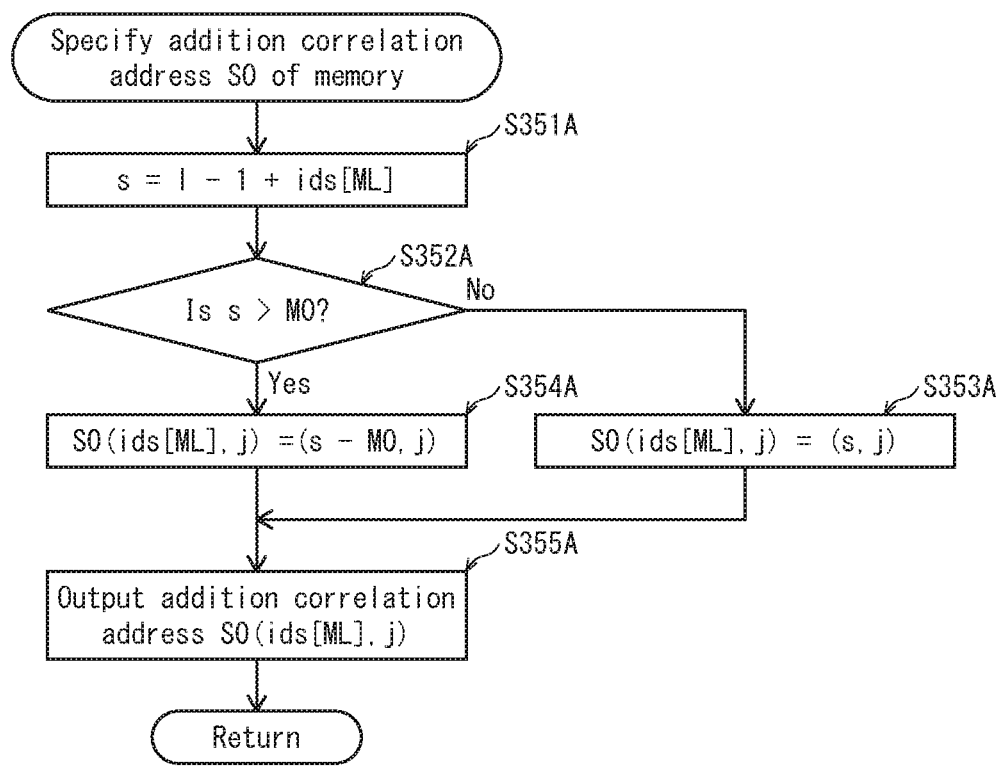
FIG. 23 is a flowchart illustrating details of step S350A in FIG. 21.

FIG. 23 is a flowchart illustrating details of step S350A. First, in step S351A, the synthesis controller 1431 calculates a provisional correlation address number s in the azimuth direction from the sum of the maximum value ids[ML] of ids[i] and a value (1−1) obtained by subtracting 1 from the transmission event count 1. Next, whether or not the provisional correlation address number s exceeds the maximum value M0 of azimuth addresses of the memory 1432 is determined (step S352A). If greater, that is, if the provisional correlation address numbers is greater than the maximum value M0 of azimuth addresses of the memory 1432, a round-up is necessary of the memory 1432, and a value obtained by subtracting the maximum value M0 of the azimuth addresses from the provisional correlation address number s in the azimuth direction is set as the addition correlation address number S0 in the azimuth direction, and this address is set for the addition correlation address S0(ids[ML],j) (step S354A). If not greater, that is, if the provisional correlation address number s is equal to or less than the maximum value M0 of azimuth addresses of the memory 1432, the value becomes the addition correlation address number S0 and this address is set as the addition correlation address S(ids[ML],j) (step S353A). Finally, the synthesis controller 1431 outputs the azimuth direction addition correlation address number S0(ids[ML],j) to the address controller 1433 (step S355A).

Next, the synthesizer 143 outputs to the ultrasound image generator 150 the synthesized acoustic line signal dsc(ij) held at the addition correlation address S0(ids[ML],j) of the memory 1432 for which synthesis processing is already complete from prior transmission events (step S360A), and zero value data is newly written to the addition correlation address S0(ids[ML],j) (step S370A).

Next, an index i indicating an azimuth direction coordinate corresponding to j is set to an initial value ids[1] (q=1) (step S144), beamforming processing is performed (steps S145 to S149), acoustic line signals are generated for observation points Pij, and processing proceeds to step S310.

Next, in step S310, a correlation address S(ids[q],j) of the memory 1432 is specified for coordinates (ids[q],j) in the target region Bx. Here, operations of step S310 are the same as operations of each step illustrated in FIG. 17, and are therefore not described again here.

Next, the summing register value and data stored at the correlation address S(ids[q],j) are summed, then the data is replaced by the results of summing (step S315A).

Next, it is determined whether or not q is the maximum value ML of acoustic line signals in the target region Bx (step S320). If less than the maximum value ML, q is incremented (step S322) and processing returns to step S145. If q is equal to the maximum value ML, processing proceeds to step S383.

Next, whether or not j is the maximum value j (D) in the target region Bx is determined (step S383). If j is less than the maximum value j (D), j is incremented (step S384) and processing returns to step S143, and an acoustic line signal ds(ids[q],j) for a new observation point Pij is generated (step S147). In this way, by incrementing j and repeating step S147, acoustic line signals ds(ids[q],j) are generated for observation points Pij corresponding to the array ids[q] of all azimuth direction coordinates positioned in the target region Bx. If j is the maximum value j (D) in step S383, processing proceeds to step S385.

Next, whether or not 1, indicating the transmission event count, is a maximum value is determined (step 385). If 1 is not the maximum value, processing returns to step S110, the transmission aperture Tx is shifted by the movement pitch Mp in the array direction, and a series of processes pertaining to the next transmission event is performed. If 1 is the maximum value, processing ends.

According to the description above, in step S143, as per Embodiment 1, for example, the array ids[q] (q=1 to ML) is changed based on j, such that acoustic line signals ds(ids[i],j) are calculated for observation points Pij in a range indicated by black circles "●" in FIG. 19C1. In this case, the target region Bx for which acoustic line signals ds(ids[q],j) are calculated has an hourglass shape.

Alternatively, if a plane wave is used as a transmission wave, the array ids[q] (q=1 to ML) may be constant, irrespective of j, such that acoustic line signals ds(ids[q],j)

are calculated for observation points Pij in a range indicated by black circles "●" and empty circles "○" in FIG. 19C1. In this case, the range for which acoustic line signals ds(ids [q],j) are calculated has a rectangular shape.

Further, an example has been described in which the movement pitch Mp is 1, but if the movement pitch Mp is two or more, the following processing is performed.

First, in step S351A, the synthesis controller 1431 calculates a provisional correlation address number s in the azimuth direction from the sum of the maximum value ids[ML] of ids[i] and a value (1−1) obtained by subtracting 1 from the transmission event count 1.

Next, in step S355A, a value (Mp−1) is subtracted from the addition correlation address number S0 in the azimuth direction calculated in step S354A or step S353A, and the synthesis controller 1431 outputs the results to the address controller 1433 as a new addition correlation address number S0. This is to make an address in the azimuth direction of the memory 1432 to which acoustic line signal line data Mp from a last line is correlated the addition correlation address S0(ids[ML],j).

In step S360A, the synthesizer 143 outputs to the ultrasound image generator 150 the synthesized acoustic line signals dsc(ids[ML],j) held at Mp addresses from the addition correlation address S0(ids[ML],j) in the azimuth direction of the memory 1432 for which synthesis processing is already complete from previous transmission events. In step S370A, the synthesizer 143 performs processing to write zero value data to the Mp addresses from the addition correlation address S0(ids[ML],j).

<Partial Summary>

According to the reception beamformer 140 pertaining to Embodiment 2 as described above, the synthesizer 143, prior to performing summing of a value of an acoustic line signal correlated with an address one before the addition correlation address S0 in the azimuth direction of the memory 1432 with data stored at that address, outputs to the ultrasound image generator 150 data stored at Mp addresses from the addition correlation address S0 in the azimuth direction of the memory 1432.

According to this configuration, in Embodiment 2, the synthesizer 143, with respect to a movement pitch Mp of transmission transducers per transmission event, after specifying an addition correlation address to which acoustic line signal line data an Mp pitch from a last line in a transmission event, does not perform a determination of whether or not a result of summing an acoustic line signal value correlated with an address one before the addition correlation address with data stored at the address has been written, and outputs to the ultrasound image generator 150 data stored at the Mp addresses from the addition correlation address S0 in the azimuth direction for all transmission events. Thus, in addition to the effects of the configuration of Embodiment 1, steps S330 and S340 of FIG. 16 can be eliminated, simplifying processing of summing data at addresses of the memory 1432 with acoustic line signal line data dsij when compared to the operations pertaining to Embodiment 1.

<<Modification 1>>

Although an ultrasound signal processing device pertaining to at least one embodiment has been described above, the present invention is not limited to the embodiments above, except for essential characteristic elements thereof. For example, embodiments obtained by various modifications conceivable by a person skilled in the art applied to any described embodiment, and any combination of elements and functions of any embodiment that does not depart from the spirit of the present invention are included in the present invention. The following describes ultrasound signal processing devices pertaining to modifications as examples of such embodiments.

The following describes a configuration of an ultrasound signal processing device pertaining to Modification 1. FIG. 24 is a schematic diagram illustrating synthesis of synthesized acoustic line signals by the synthesizer 143 pertaining to Modification 1.

According to Embodiments 1 and 2, the synthesizer 143 correlates each acoustic line signal line data of acoustic line signal data obtained in correspondence with transmission events with addresses of the memory 1432 with positions of observation points Pij in the irradiation region Ax as a reference, summing acoustic line signals with data at a correlated correlation address S, and thereby synthesizing acoustic line signal line data obtained for each transmission event.

According to the ultrasound signal processing device pertaining to Modification 1, as illustrated in FIG. 24, the synthesizer 143 sums acoustic line signal line data in units of acoustic line signal line data ds(1), ds(2), ds(3) with data at correlation addresses of the memory 1432. Further, generation of acoustic line signal line data ds(1), ds(2), ds(3) in the delay-and-sum unit 142, and summing of acoustic line signal line data ds(1), ds(2), ds(3) with data at correlation addresses S of the memory 1432 by the synthesizer 143 are performed within 10 ns, which is one time slot obtained by dividing one sample period by the number (3) of acoustic line signal line data included in acoustic line signal line data obtained in the one sample period, and the acoustic line signal line data ds(1), ds(2), ds(3) are time-divisionally processed in three time slots in a transmission event. More specifically, as illustrated in FIG. 22, in time slot 3, acoustic line signal line data ds(3) is summed and written to address (3), and at the same time address (1) is reserved, acoustic signal line data ds(1) is read, and output to a subsequent stage. Further, in time slot 1, acoustic line signal line data ds(1) is summed and written to address (1), and at the same time address (2) is reserved, acoustic line signal line data ds(2) is read, and output to a subsequent stage. Further, in time slot 2, acoustic line signal line data ds(2) is summed and written to address (2), and at the same time address (3) is reserved, acoustic line signal line data ds(3) is read, and output to a subsequent stage.

By using this configuration, simultaneous access to the memory 1432 does not occur with respect to summing processing related to acoustic line signal line data ds(1), ds(2), ds(3), and therefore 1R1W type single port SRAM can be used, and hardware cost of the memory 1432 can be further reduced. Further, for example, a mounting area can be further reduced when compared to a case in which the memory 1432 is configured with a multiport memory such as a 2R1W type, a 2R2W type, or the like.

<<Modification 2>>

Figure 25:
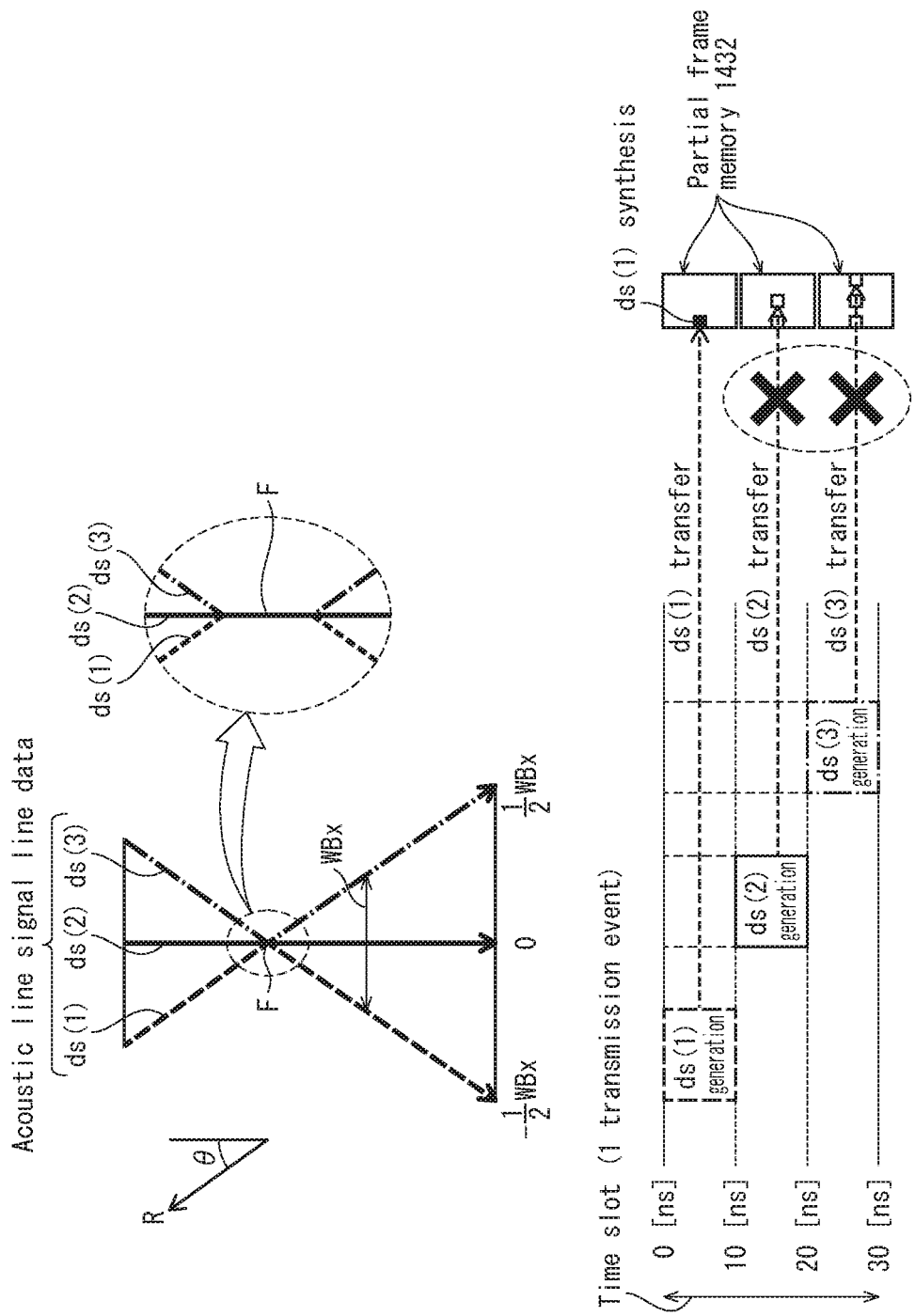
FIG. 25 is a schematic diagram illustrating synthesis of synthesized acoustic line signals by the synthesizer 143 pertaining to Modification 2.

The following describes a configuration of an ultrasound signal processing device pertaining to Modification 2. FIG. 25 is a schematic diagram illustrating synthesis of synthesized acoustic line signals by the synthesizer 143 pertaining to Modification 2.

According to Embodiments 1 and 2, the synthesizer 143 correlates acoustic line signal line data obtained in correspondence with transmission events with addresses of the memory 1432, using positions of observation points Pij plotted using orthogonal coordinates in the target region Bx as a reference, and by summing acoustic line signals with data at correlated addresses with reference to each observation point Pij, acoustic line signal line data obtained in each transmission event is synthesized.

According to an ultrasound signal processing device pertaining to Modification 2, as illustrated in FIG. 25, observation points are plotted following a travel direction of ultrasound beams, for example using polar coordinates (R,θ) in the target region. In this case, in the vicinity of the transmission focal point F, positions of observation points for calculating acoustic line signal line data ds(1), ds(2), ds(3) overlap and observation points related to a plurality of acoustic line signal line data may be plotted at the same coordinates. For example, when a width WBx of the azimuth direction of the target region Bx, which is a region in which observation points Pij are set, is a value obtained by multiplying distance in the depth direction from the focal point F by a constant, observation points will be plotted on the same coordinates.

More specifically, as illustrated in FIG. 25, when positions in the azimuth direction relative to the focal point F of acoustic line signal line data ds(1), ds(2), and ds(C3) are defined as −WBx/2 for ds(1), 0 for ds(2), and +WBx/2 for ds(3), and WBx is equal to or less than 1 in the vicinity of the focal point F, a situation occurs in which acoustic line signal line data ds(1), ds(2), and ds(3) are superimposed. In such a case, in processing related to different acoustic line signal data ds(1), ds(2), ds(3), correlation and input/output may occur with respect to the same memory of the memory 1432. In attempting to avoid this through logical processing in the synthesis controller 1431, complicated conditional branching or calculation may become necessary, leading to an increase in circuit scale.

Thus, according to the ultrasound signal processing device pertaining to Embodiment 2, the synthesizer 143 includes the address controller 1433 and the input/output controller 1434 that control input to and output from the memory 1432, and the address controller 1433 and the input/output controller 1434 prohibit input and output to the correlation address S to which a result of summing has already been written in the same transmission event.

According to this configuration, in comparison to a case in which the synthesis controller 1431 is controlled by control of memory controllers, preventing input to and output from the same memory of the memory 1432 in processing related to different acoustic line signals in the same transmission event is easier to implement. As a result, it is possible to reduce the number of accesses of the memory 1432, which can contribute to faster processing.

<<Modification 3>>

According to Modification 1, in a transmission event, the synthesizer 143 specifies a correlation address S(ids[q],j) of the memory 1432 for a coordinate of the target region Bx (step S310), sums acoustic line signal line data dsij with data at the corresponding address, and updates the data with the results of summing (step S321). Thus, a condition in which no acoustic line signals generated and stored in the memory 1432 in a previous transmission event are present is provided, and in the first transmission event after a start of a reception beamforming operation, it is necessary to initialize the memory 1432 to convert data at all addresses to zero (step S10).

Reception beamforming pertaining to Modification 3 is different from Embodiment 1 in that initialization of the memory 1432 in the first transmission event after a start of reception beamforming is not performed, and in terms of a condition that no acoustic line signals are generated and stored in the memory 1432 in a previous transmission event, summing acoustic line signal line data dsij with data at a corresponding address after converting data at the corresponding address to a zero value, and updating the data with the result of summing <Operations>

The following describes operations of the synthesizer 143 of the ultrasound diagnostic device pertaining to Modification 3.

According to Modification 3, configuration of a reception beamformer is the same as that of the reception beamformer 140 pertaining to Embodiment 1, illustrated in FIG. 3. According to the ultrasound diagnostic device pertaining to Modification 3, in operation of the synthesizer 143, processing related to the condition that no acoustic line signals generated and stored in the memory 1432 in a previous transmission event are present is different from Embodiment 1. Thus, only differences in operation are described. Structure and other operations are the same as in Embodiment 1, and therefore the same reference symbols are used and redundant description is omitted.

Figure 26:
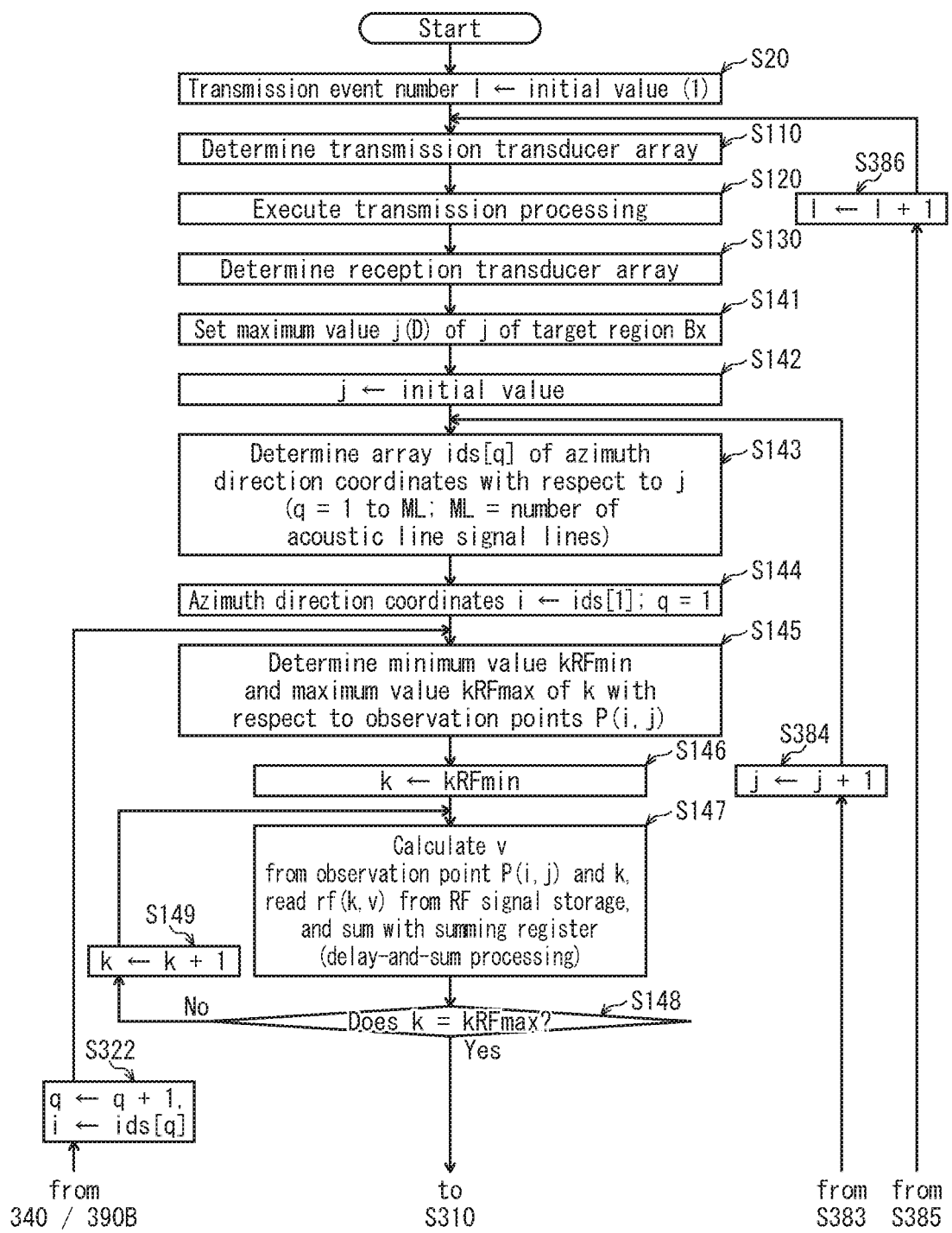
FIG. 26 is a flowchart illustrating beamforming processing of the reception beamformer 140 pertaining to Modification 3.
Figure 27:
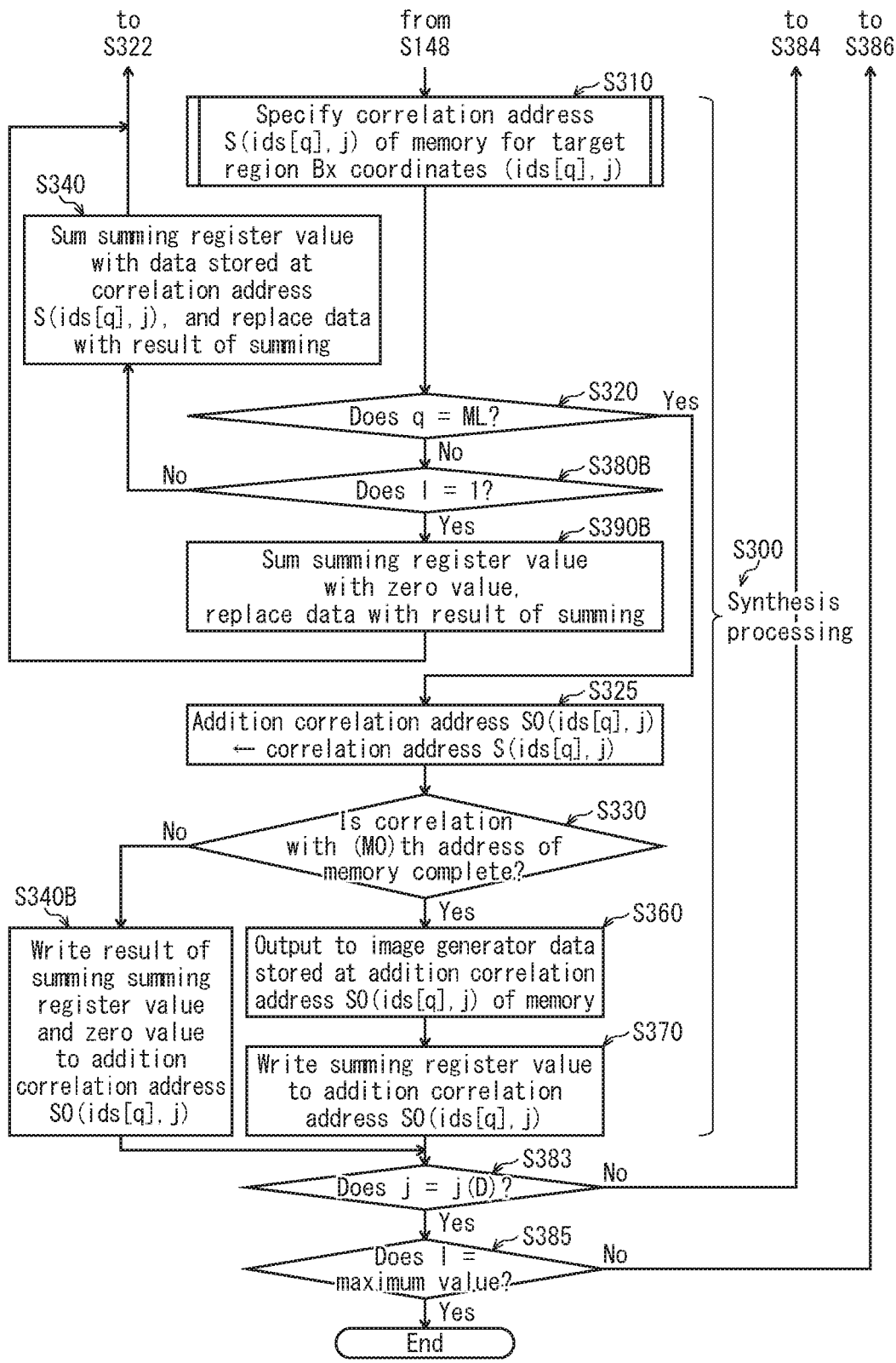
FIG. 27 is a flowchart illustrating beamforming processing of the reception beamformer 140 pertaining to Modification 3.

The following describes operations of an ultrasound diagnostic device pertaining to Modification 3. FIGS. 26 and 27 are flowcharts illustrating beamforming processing of the reception beamformer 140 pertaining to Modification 3.

Processing in FIGS. 26 and 27 is different from operation of Embodiment 1 illustrated in FIG. 15 in steps S340B, S380B, and S390B, and in that step S10 of FIG. 15 for initializing the memory 1432 is not present. Other processing, that is, processing of steps S20, S110 to S149, S310, S320, S325, S330, S360, S370, and S381 to S386 is the same as Embodiment 1 in FIGS. 15 and 16, and redundant description is omitted.

First, as per Embodiment 1, in FIG. 27, in step S310, a correlation address S(ids[q],j) of the memory 1432 is specified with respect to coordinates (ids[q],j) in the target region Bx, and whether or not q is a maximum value ML of acoustic line signal lines in the target region Bx is determined (step S320). When less than the maximum value ML, it is determined whether or not the current transmission event is a first transmission event (step S380B). If not the first transmission event, as per Embodiment 1, a summing register value is summed with data stored at the correlation address S(ids[q],j), and after the data is replaced with a result of summing (step S340), q is incremented (step S322), and processing returns to step S223. In the determination of step S380B, when it is the first transmission event, this corresponds to a condition that acoustic line signals generated and stored in the memory 1432 in a previous transmission event are not present. Thus, a summing register value and a zero value ("0") are summed, and after data at the correlation address S(ids[q],j) is replaced with a result of summing (step S390B), q is incremented (step S322), and processing returns to step S223.

On the other hand, in the determination of step S320, if q is the maximum value ML of acoustic line signal lines in the target region Bx, the correlation address S(ids[q],j) is recognized as the addition correlation address S0(ids[q],j) (step S325), and processing proceeds to step S330. Here it is determined whether or not correlation with the (M0)th azimuth address of the memory 1432 is complete (step S330), and if correlation with the (M0)th azimuth address is complete, processing proceeds to step S360, as per Embodiment 1.

In the determination of step S330, when not complete, this corresponds to a condition that acoustic line signals generated and stored in the memory 1432 in a previous transmission event are not present. Thus, after writing a result of summing a summing register value and a zero value ("0") to the addition correlation address S0(ids[q],j) (step S340B), and processing proceeds to step S383.

Next, whether or not j is the maximum value j (D) in the target region Bx is determined (step S383). If j is less than the maximum value j (D), j is incremented (step S384) and processing returns to step S143. If j is the maximum value j(D), it is determined whether or not the transmission event count indicated by 1 is a maximum value (step S385). If 1 is not the maximum value, processing returns to step S110, 1 is incremented (step S386), the transmission aperture Tx is shifted by the movement pitch Mp in the array direction, and a series of processes pertaining to the next transmission event is performed. If 1 is the maximum value, processing ends.

<Partial Summary>

According to the reception beamformer 140 pertaining to Modification 3, the synthesizer 143, before correlating with the (M0)th address in the azimuth direction of the memory 1432, outputs to the ultrasound image generator 150 data stored at addresses in the azimuth direction of the memory 1432 corresponding to acoustic line signal line data up to Mp lines from a last acoustic line signal line data in the azimuth direction among acoustic line signal line data, and converts the data to zero values.

According to this configuration, in reception beamforming pertaining to Modification 3, it is determined whether acoustic line signals generated and stored in the memory 1432 from a previous transmission event exist, and after converting data at corresponding addresses to zero values, acoustic line signal line data dsij is summed with data at corresponding addresses, and the data is updated with results of summing. As a result, in addition to achieving the effects of Embodiments 1 and 2, after starting reception beamforming, in a first transmission event, a process of initializing the memory 1432 to convert data at all addresses to zero values (step S10) can be eliminated.

<<Other Modifications>>

(1) According to the ultrasound diagnostic device 100 pertaining to Embodiment 1, the reception aperture setting section 14213 selects the reception aperture Rx such that an array center coincides with the transducer having closest spatial proximity to an observation point Pij. However, configuration of the reception aperture Rx can be appropriately modified.

For example, a transmission-correlated reception aperture setting section may be provided that selects a reception aperture Rx transducer array that has an array center that coincides with an array center of a transmission aperture Tx transducer array. According to this configuration, a reception aperture Rx transducer array is selected so that an array center of a reception aperture Rx transducer array coincides with an array center of a transmission aperture Tx transducer array. Position of a center axis of a reception aperture Rx coincides with position of a center axis of a transmission aperture Tx, and the reception aperture Rx is an aperture symmetrical about the transmission focal point F. Accordingly, position of the reception aperture Rx also shifts in correspondence with position changes of the transmission aperture Tx shifting in the array direction per transmission event.

(2) A weighting number sequence (reception apodization) with respect to each reception transducer Rk of a reception aperture Rx may be calculated so that weight of a transducer positioned on a central axis of the reception aperture Rx and a central axis of the transmission aperture Tx is a maximum. A weighting sequence has a symmetric distribution about the center transducer Rx. As a shape of a weighting sequence distribution, a Hamming window, a Hann window, a rectangular window, or the like can be used, and the shape of distribution is not limited to any particular example.

(3) The ultrasound diagnostic device 100 pertaining to any embodiment is not limited to the ultrasound diagnostic device configuration illustrated in FIG. 1. For example, the transmission beamformer 130 and the reception beamformer 140 may be directly connected to the transducers 110a of the probe 110 without the multiplexer 120. Further, the transmission beamformer 130, the reception beamformer 140, or a portion thereof may be inside the probe 110. This is not limited only to the ultrasound diagnostic device 100 pertaining to embodiments described above, and the same applies to other ultrasound diagnostic devices pertaining to embodiments described below and modifications.

(4) The present invention is described based on the embodiments above, but the present invention is not limited to these embodiments, and the following examples are also included in the scope of the present invention.

For example, the present invention may be a computer system including a microprocessor and a memory, the memory storing a computer program and the microprocessor operating according to the computer program. For example, the present invention may be a computer system that operates (or instructs operation of connected elements) according to a computer program of a diagnostic method of an ultrasound diagnostic device of the present invention.

Further, examples in which all or part of the ultrasound diagnostic device, or all or part of a beamforming section are constituted by a computer system including a microprocessor, a storage medium such as ROM, RAM, etc., a hard disk unit, and the like, are included in the present invention. A computer program for achieving the same operations as the devices described above may be stored in RAM or a hard disk unit. The microprocessor operating according to the computer program, thereby realizing the functions of each device.

Further, all or part of the elements of each device may be configured as one system large scale integration (LSI). A system LSI is an ultra-multifunctional LSI manufactured by integrating a plurality of elements on one chip, and more specifically is a computer system including a microprocessor, ROM, RAM, and the like. The plurality of elements can be integrated on one chip, or a portion may be integrated on one chip. Here, LSI may refer to an integrated circuit, a system LSI, a super LSI, or an ultra LSI, depending on the level of integration. A computer program for achieving the same operation as the devices described above may be stored in the RAM. The microprocessor operates according to the computer program, the system LSI thereby realizing the functions. For example, a case of the beamforming method of the present invention stored as a program of an LSI, the LSI inserted into a computer, and a defined program (beamforming method) being executed is also included in the present invention.

Note that methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the function blocks.

Further, all or part of the functions of an ultrasonic diagnostic device pertaining to at least one embodiment may be implemented by execution of a program by a processor such as a CPU. All or part of the functions of an ultrasound diagnostic device pertaining to at least one embodiment may be implemented by a non-transitory computer-readable storage medium on which a program is stored that causes execution of a diagnostic method or beamforming method of an ultrasound diagnostic device described above. A program and signals may be recorded and transferred on a storage medium so that the program may be executed by another independent computer system, or the program may of course be distributed via a transmission medium such as the Internet.

Alternatively, such elements may be implemented by a programmable device such as a central processing unit (CPU), general-purpose computing on a graphics processing unit (GPGPU), a processor, or the like, and software. These elements can each be a single circuit component or an assembly of circuit components. Further, a plurality of elements can be combined into a single circuit component or can be an aggregate of a plurality of circuit components.

According to an ultrasound diagnostic device pertaining to at least one embodiment, the ultrasound diagnostic device includes a data storage as a storage device. However, the storage device is not limited to this example and a semiconductor memory, hard disk drive, optical disk drive, magnetic storage device, or the like may be externally connectable to the ultrasound diagnostic device.

Further, the division of function blocks in the block diagrams is merely an example, and a plurality of function blocks may be implemented as one function block, one function block may be divided into a plurality, and a portion of a function may be transferred to another function block. Further, a single hardware or software element may process the functions of a plurality of function blocks having similar functions in parallel or by time division.

Further, the order in which steps described above are executed is for illustrative purposes, and the steps may be in an order other than described above. Further, a portion of the steps described above may be executed simultaneously (in parallel) with another step.

Further, the ultrasound diagnostic device is described as having an externally connected probe and display, but may be configured with an integral probe and/or display.

Further, a portion of functions of transmitters and receivers may be included in the probe. For example, a transmission electrical signal may be generated and converted to ultrasound in the probe, based on a control signal for generating a transmission electrical signal outputted from the transmitter. It is possible to use a configuration that converts received reflected ultrasound into a reception electrical signal and generates a reception signal based on the reception electrical signal in the probe.

Further, at least a portion of functions of each ultrasound diagnostic device pertaining to an embodiment, and each modification thereof, may be combined. Further, the numbers used above are all illustrative, for the purpose of explaining the present invention in detail, and the present invention is not limited to the example numbers used above.

Further, the present invention includes various modifications that are within the scope of conceivable ideas by a person skilled in the art.

<<Review>>

An ultrasound signal processing device pertaining to the present disclosure is an ultrasound signal processing device that transmits an ultrasound beam from an ultrasound probe provided with N transducers in an azimuth direction, where N is a natural number greater than 1, and generates N azimuth direction×Z depth direction acoustic line signal frame data from acoustic line signals based on reflected ultrasound, where Z is a natural number, the ultrasound signal processing device including ultrasound signal processing circuitry, the ultrasound signal processing circuitry including: a transmitter that repeats transmission events, in which an ultrasound beam is transmitted from an array of transmission transducers selected from the N transducers, the array of transmission transducers being shifted by Mp transducers in the azimuth direction per transmission event, where Mp is a natural number; a delay-and-sum unit that generates a radio frequency (RF) signal sequence based on reflected ultrasound received by all or a plurality of the N transducers corresponding to a transmission event, performs delay-and-sum processing on the RF signal sequences for each observation point corresponding to positions in an ultrasound beam irradiation region, and generates ML lines of acoustic line signal line data, where ML is a natural number less than N; a partial frame memory partitioned into M0 azimuth direction×D depth direction addresses, where M0 is a natural number such that ML≤M0≤N and D is a natural number; a synthesizer that makes a correlation between acoustic line signal line data corresponding to transmission events and addresses of the partial frame memory, using positions of observation points from which acoustic line signals are obtained as a reference, synthesizes acoustic line signal line data obtained from transmission events by summing acoustic line signals with data stored at corresponding addresses which have been correlated with the acoustic line signals, and generates the N azimuth direction×D depth direction acoustic line signal frame data; and an ultrasound image generator that generates an ultrasound image based on the acoustic line signal frame data, wherein the synthesizer makes the correlation between the acoustic line signal line data corresponding to transmission events and the addresses of the partial frame memory in an order along the azimuth direction, when acoustic line signal line data is correlated with an (M0)th address in the azimuth direction of the partial frame memory, remaining acoustic line signal line data in the azimuth direction is then correlated in the order along the azimuth direction to addresses starting from a first address in the azimuth direction of the partial frame memory, and an address in the azimuth direction of the partial frame memory to which acoustic line signal line data is correlated, counting back Mp lines in the azimuth direction starting at a latest acoustic line signal line data corresponding to the transmission event, is specified as an addition correlation address, values of acoustic line signals correlated with addresses from the first address to an address one before the addition correlation address in the azimuth direction of the partial frame memory are summed with data stored at the addresses, and results of summing are written to the addresses, and with respect to Mp addresses starting at and including the addition correlation address in the order along the azimuth direction of the partial frame memory, after outputting to the ultrasound image generator data stored at the Mp addresses, values of corresponding acoustic line signals are written to the Mp addresses.

According to this configuration, using the partial frame memory 1432 in which the address number M0 in the azimuth direction is less than the total channel number corresponding to the total number N of the transducers 110*a*, it is possible to synthesize acoustic line signal frame data for the total line number N in the azimuth direction and to reduce memory capacity required for acoustic line signal synthesis in reception beamforming using a synthetic aperture method while suppressing a decrease in spatial resolution and signal-to-noise ratio.

According to at least one embodiment, the synthesizer outputs to the ultrasound image generator the data stored at the Mp addresses after writing to an address one before the addition correlation address in the azimuth direction of the partial frame memory the results of summing a value of an acoustic line signal corresponding to the address with data stored at the address.

According to this configuration, as a condition of writing results of summing a value of an acoustic line signal correlated with an address one before the addition correlation address S0 with data stored at the address, the synthesizer 143 outputs to the ultrasound image generator 150 data stored at addresses including the addition correlation address S0 in the azimuth direction.

According to at least one embodiment, the synthesizer outputs to the ultrasound image generator the data stored at the Mp addresses before summing a value of an acoustic line signal corresponding to an address one before the addition correlation address in the azimuth direction of the partial frame memory with data stored at the address.

According to at least one embodiment, prior to correlating with the (M0)th address in the azimuth direction of the partial frame memory, with respect to acoustic line signal line data corresponding to the transmission event, the synthesizer converts to zero then outputs to the ultrasound image generator data stored at addresses of the partial frame memory to which Mp lines of acoustic line signal data are correlated, counting back in the azimuth direction starting at a latest acoustic line signal line data.

According to this configuration, after specifying the addition correlation address, there is no need to determine whether or not writing results of summing a value of an acoustic line signal correlated with an address one before the addition correlation address S0 with data stored at the address has occurred, and for all transmission events the synthesizer 143 outputs to the ultrasound image generator 150 data stored at addresses including the addition correlation address S0 in the azimuth direction. Thus, synthesis of acoustic line signal line data and data at corresponding addresses of the memory 1432 can be simplified.

According to at least one embodiment, the delay-and-sum unit and the synthesizer are included in a first integrated circuit, the partial frame memory is SRAM included in the first integrated circuit, the ultrasound image generator is included in a second integrated circuit that is different from the first integrated circuit, and output of the acoustic line signal line data by the synthesizer from the first integrated circuit to the second integrated circuit corresponds to transmission events.

According to this configuration, there is no need to provide a large scale SRAM in an FPGA, and the hardware cost of the FPGA can be reduced. Further, there is no need to provide a large capacity DDR memory outside the FPGA for synthesizing, no need to provide a memory controller with high processing capability in the FPGA for high speed data transfer between FPGA and DDR memory, and therefore hardware costs can be reduced.

Further, bus capacity required for data transfer between integrated circuits can be reduced. As a result, reception beamforming processing from echo signal reception up until synthesis processing can be realized by using only internal memory of small-scale FPGAs, and it becomes possible to reduce hardware costs in comparison to conventional art.

According to at least one embodiment, the synthesizer sums acoustic line signal line data with data stored at corresponding addresses of the partial frame memory in units of acoustic line signal line data. According to at least one embodiment, the synthesizer sums acoustic line signal line data with data stored at corresponding addresses of the partial frame memory in units of acoustic line signals included in the acoustic line signal line data.

According to at least one embodiment, generation of acoustic line signal line data by the delay-and-sum unit and summing acoustic line signal line data with data stored at the corresponding addresses of the partial frame memory are performed in one time slot, which is one sample period divided by a number of lines of acoustic line signal line data obtained in the one sample period, and acoustic line signal line data is time-divisionally processed in a transmission event.

According to this configuration, simultaneous access to the memory 1432 does not occur with respect to summing related to acoustic line signal line data, and therefore 1R1W type single port SRAM can be used, meaning hardware cost can be reduced. Further, if the memory 1432 is provided with multiport memory, a mounting surface area can be reduced.

According to at least one embodiment, the synthesizer includes an input/output controller and an address controller that control input to and output from the partial frame memory, and the input/output controller and the address controller prohibit input and output of data to corresponding addresses to which results of summing have already been written in a given transmission event.

According to this configuration, preventing input to and output from the same memory of the memory 1432 in processing related to different acoustic line signals in the same transmission event can be easily implemented.

According to at least one embodiment, the synthesizer, in a first transmission event, performs summing after converting data stored at all addresses of the partial frame memory into zero values, and in second and subsequent transmission events, performs summing related to corresponding addresses after converting to zero values data stored at addresses in the azimuth direction of the partial frame memory that correspond to acoustic line signal line data from a latest acoustic line signal line data to an (Mp)th acoustic line signal line data in the azimuth direction among acoustic line signal line data obtained in a transmission event.

According to this configuration, with respect to a first transmission event after reception beamforming starts, processing to initialize the memory 1432, converting data at all address to zero values (step S10), can be eliminated.

According to at least one embodiment, the transmitter sets a focal point defining a point of convergence of an ultrasound beam in a subject, and repeatedly performs transmission events transmitting ultrasound beams converging on the focal point from the array of the transmission transducers selected from the N transducers while gradually shifting the focal point in the azimuth direction.

According to this configuration, it is possible to obtain a high-quality image having a high spatial resolution even in close vicinity to a transmission focal point, and to generate acoustic line signals for an entirety of an ultrasound primary irradiation region including areas other than close vicinity of the transmission focal point from one ultrasound transmission, and to improve spatial resolution and signal-to-noise ratio.

<<Supplement>>

The embodiments described above each indicate one preferred specific example of the present invention. Numerical values, shapes, materials, constituent elements, arrangement positions and connections of constituent elements, steps, order of steps, and the like indicated as embodiments are merely examples and are not intended to limit the present invention. Further, among constituent elements in the embodiments, elements not described in independent claims representing top level concepts of the present invention are described as any constituent element constituting a more beneficial embodiment.

Further, the order in which steps described above are executed is for illustrative purposes, and the steps may be in an order other than described above. Further, a portion of the steps described above may be executed simultaneously (in parallel) with another step.

Further, in order to facilitate understanding of the invention, constituent elements in each drawing referenced by description of an embodiment are not necessarily to scale. Further, the present invention is not limited by the description of each embodiment, and can be appropriately changed without departing from the scope of the present invention.

Although the technology pertaining to the present disclosure has been fully described by way of examples with reference to the accompanying drawings, various changes and modifications will be apparent to those skilled in the art. Therefore, unless such changes and modifications depart from the scope of the present disclosure, they should be construed as being included therein.

What is claimed is:

1. An ultrasound signal processing device that transmits an ultrasound beam from an ultrasound probe provided with N transducers in an azimuth direction, where N is a natural number greater than 1, and generates N azimuth direction×Z depth direction acoustic line signal frame data from acoustic line signals based on reflected ultrasound, where Z is a natural number, the ultrasound signal processing device including ultrasound signal processing circuitry, the ultrasound signal processing circuitry comprising:
a transmitter that repeats transmission events, in which an ultrasound beam is transmitted from an array of transmission transducers selected from the N transducers, the array of transmission transducers being shifted by Mp transducers in the azimuth direction per transmission event, where Mp is a natural number;
a delay-and-sum unit that generates a radio frequency (RF) signal sequence based on reflected ultrasound received by all or a plurality of the N transducers corresponding to a transmission event, performs delay-and-sum processing on the RF signal sequences for each observation point corresponding to positions in an ultrasound beam irradiation region, and generates ML lines of acoustic line signal line data, where ML is a natural number less than N;
a partial frame memory partitioned into M0 azimuth direction×D depth direction addresses, where M0 is a natural number such that ML≤M0≤N and D is a natural number;
a synthesizer that makes a correlation between acoustic line signal line data corresponding to transmission events and addresses of the partial frame memory, using positions of observation points from which acoustic line signals are obtained as a reference, synthesizes acoustic line signal line data obtained from transmission events by summing acoustic line signals with data stored at corresponding addresses which have been correlated with the acoustic line signals, and generates the N azimuth direction×D depth direction acoustic line signal frame data; and
an ultrasound image generator that generates an ultrasound image based on the acoustic line signal frame data, wherein
the synthesizer makes the correlation between the acoustic line signal line data corresponding to transmission events and the addresses of the partial frame memory in an order along the azimuth direction,
when acoustic line signal line data is correlated with an (M0)th address in the azimuth direction of the partial frame memory, remaining acoustic line signal line data in the azimuth direction is then correlated in the order along the azimuth direction to addresses starting from a first address in the azimuth direction of the partial frame memory, and an address in the azimuth direction of the partial frame memory to which acoustic line signal line data is correlated, counting back Mp lines in the azimuth direction starting at a latest acoustic line signal line data corresponding to the transmission event, is specified as an addition correlation address,
values of acoustic line signals correlated with addresses from the first address to an address one before the addition correlation address in the azimuth direction of the partial frame memory are summed with data stored at the addresses, and results of summing are written to the addresses, and
with respect to Mp addresses starting at and including the addition correlation address in the order along the azimuth direction of the partial frame memory, after outputting to the ultrasound image generator data stored at the Mp addresses, values of corresponding acoustic line signals are written to the Mp addresses.

2. The ultrasound signal processing device of claim 1, wherein
the synthesizer outputs to the ultrasound image generator the data stored at the Mp addresses after writing to an address one before the addition correlation address in the azimuth direction of the partial frame memory the results of summing a value of an acoustic line signal corresponding to the address with data stored at the address.

3. The ultrasound signal processing device of claim 1, wherein
the synthesizer outputs to the ultrasound image generator the data stored at the Mp addresses before summing a value of an acoustic line signal corresponding to an address one before the addition correlation address in the azimuth direction of the partial frame memory with data stored at the address.

4. The ultrasound signal processing device of claim 3, wherein
prior to correlating with the (M0)th address in the azimuth direction of the partial frame memory, with respect to acoustic line signal line data corresponding to the transmission event, the synthesizer converts to zero then outputs to the ultrasound image generator data stored at addresses of the partial frame memory to which Mp lines of acoustic line signal data are correlated, counting back in the azimuth direction starting at a latest acoustic line signal line data.

5. The ultrasound signal processing device of claim 1, wherein
the delay-and-sum unit and the synthesizer are included in a first integrated circuit,
the partial frame memory is SRAM included in the first integrated circuit, the ultrasound image generator is included in a second integrated circuit that is different from the first integrated circuit, and output of the acoustic line signal line data by the synthesizer from the first integrated circuit to the second integrated circuit corresponds to transmission events.

6. The ultrasound signal processing device of claim 1, wherein
the synthesizer sums acoustic line signal line data with data stored at corresponding addresses of the partial frame memory in units of acoustic line signal line data.

7. The ultrasound signal processing device of claim 6, wherein
generation of acoustic line signal line data by the delay-and-sum unit and
summing acoustic line signal line data with data stored at the corresponding addresses of the partial frame memory
are performed in one time slot, which is one sample period divided by a number of lines of acoustic line signal line data obtained in the one sample period, and
acoustic line signal line data is time-divisionally processed in a transmission event.

8. The ultrasound signal processing device of claim 1, wherein
the synthesizer includes an input/output controller and an address controller that control input to and output from the partial frame memory, and
the input/output controller and the address controller prohibit input and output of data to corresponding addresses to which results of summing have already been written in a given transmission event.

9. The ultrasound signal processing device of claim 1, wherein
the synthesizer,
in a first transmission event, performs summing after converting data stored at all addresses of the partial frame memory into zero values, and
in second and subsequent transmission events, performs summing related to corresponding addresses after converting to zero values data stored at addresses in the azimuth direction of the partial frame memory that correspond to acoustic line signal line data from a latest acoustic line signal line data to an (Mp)th acoustic line signal line data in the azimuth direction among acoustic line signal line data obtained in a transmission event.

10. The ultrasound signal processing device of claim 1, wherein
the transmitter sets a focal point defining a point of convergence of an ultrasound beam in a subject, and repeatedly performs transmission events transmitting ultrasound beams converging on the focal point from the array of the transmission transducers selected from the N transducers while gradually shifting the focal point in the azimuth direction.

11. An ultrasound signal processing method according to which an ultrasound beam is transmitted from an ultrasound probe provided with N transducers in an azimuth direction, where N is a natural number greater than 1, and generates N azimuth direction×Z depth direction acoustic line signal frame data from acoustic line signals based on reflected ultrasound, where Z is a natural number, the ultrasound signal processing method comprising:
a transmission step of repeating transmission events, in which an ultrasound beam is transmitted from an array of transmission transducers selected from the N transducers, the array of transmission transducers being shifted by Mp transducers in the azimuth direction per transmission event, where Mp is a natural number;
a delay-and-sum step of generating a radio frequency (RF) signal sequence based on reflected ultrasound received by all or a plurality of the N transducers corresponding to a transmission event, performs delay-and-sum processing on the RF signal sequences for each observation point corresponding to positions in an ultrasound beam irradiation region, and generates ML lines of acoustic line signal line data, where ML is a natural number less than N; and
using a partial frame memory partitioned into M0 azimuth direction×D depth direction addresses, where M0 is a natural number such that ML≤M0≤N and D is a natural number,
a synthesis step of making a correlation between acoustic line signal line data corresponding to transmission events and addresses of the partial frame memory, using positions of observation points from which acoustic line signals are obtained as a reference, synthesizing acoustic line signal line data obtained from transmission events by summing acoustic line signals with data stored at corresponding addresses which have been correlated with the acoustic line signals, and generating the N azimuth direction×D depth direction acoustic line signal frame data; and
an image generation step of generating an ultrasound image based on the acoustic line signal frame data, wherein
in the synthesis step, the correlation between the acoustic line signal line data corresponding to transmission events and the addresses of the partial frame memory is made in an order along the azimuth direction,
when acoustic line signal line data is correlated with an (M0)th address in the azimuth direction of the partial frame memory, remaining acoustic line signal line data in the azimuth direction is then correlated in the order along the azimuth direction to addresses starting from a first address in the azimuth direction of the partial frame memory, and an address in the azimuth direction of the partial frame memory to which acoustic line signal line data is correlated, counting back Mp lines in the azimuth direction starting at a latest acoustic line signal line data corresponding to the transmission event, is specified as an addition correlation address,
values of acoustic line signals correlated with addresses from the first address to an address one before the addition correlation address in the azimuth direction of the partial frame memory are summed with data stored at the addresses, and results of summing are written to the addresses, and
with respect to Mp addresses starting at and including the addition correlation address in the order along the azimuth direction of the partial frame memory, after outputting to the ultrasound image generator data stored at the Mp addresses, values of corresponding acoustic line signals are written to the Mp addresses.

12. The ultrasound signal processing method of claim 11, wherein
in the synthesis step, the data stored at the Mp addresses is supplied to the image generation step after writing to an address one before the addition correlation address in the azimuth direction of the partial frame memory the results of summing a value of an acoustic line signal corresponding to the address with data stored at the address.

13. The ultrasound signal processing method of claim 11, wherein
in the synthesis step, the data stored at the Mp addresses is supplied to the image generation step before summing a value of an acoustic line signal corresponding to an address one before the addition correlation address in the azimuth direction of the partial frame memory with data stored at the address.

14. The ultrasound signal processing method of claim 13, wherein
prior to correlating with the (M0)th address in the azimuth direction of the partial frame memory, with respect to acoustic line signal line data corresponding to the transmission event, in the synthesis step, data stored at addresses of the partial frame memory to which Mp lines of acoustic line signal data are correlated, counting back in the azimuth direction starting at a latest acoustic line signal line data, is converted to zero then supplied to the image generation step.

* * * * *